US009468433B2

(12) United States Patent
Denham et al.

(10) Patent No.: US 9,468,433 B2
(45) Date of Patent: Oct. 18, 2016

(54) METHOD AND APPARATUS FOR FORMING A SELF-LOCKING ADJUSTABLE LOOP

(75) Inventors: Gregory J. Denham, Warsaw, IN (US); Kevin T. Stone, Winona Lake, IN (US); Zachary Wagner, Lafayette, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 1019 days.

(21) Appl. No.: 13/288,459

(22) Filed: Nov. 3, 2011

(65) Prior Publication Data

US 2012/0053630 A1 Mar. 1, 2012

Related U.S. Application Data

(60) Continuation-in-part of application No. 13/111,564, filed on May 19, 2011, now Pat. No. 8,574,235, which (Continued)

(51) Int. Cl.
*A61B 17/04* (2006.01)
*A61B 17/84* (2006.01)
(Continued)

(52) U.S. Cl.
CPC ......... *A61B 17/0401* (2013.01); *A61B 17/842* (2013.01); *A61F 2/0811* (2013.01); *A61B 17/06004* (2013.01); *A61B 17/82* (2013.01); *A61B 2017/0406* (2013.01); *A61B 2017/0417* (2013.01); *A61B 2017/0419* (2013.01);
(Continued)

(58) Field of Classification Search
CPC ................ A61B 2017/06185; A61B 17/0401; A61B 17/0487; A61B 17/06; A61B 17/06166; A61B 2017/00663; A61B 2017/0414; A61B 2017/0446; A61B 2017/0464; A61B 2017/06052; A61B 2017/06057
See application file for complete search history.

(56) References Cited

U.S. PATENT DOCUMENTS

| 26,501 | A | 12/1859 | Kendrick et al. |
| 64,499 | A | 5/1867 | Daubert |

(Continued)

FOREIGN PATENT DOCUMENTS

| AU | 4957264 | 3/1966 |
| AU | 440266 | 10/1967 |

(Continued)

OTHER PUBLICATIONS

US 6,238,418, 05/2001, Schwartz et al. (withdrawn)

(Continued)

*Primary Examiner* — Todd J Scherbel
(74) *Attorney, Agent, or Firm* — Schwegman Lundberg & Woessner, P.A.

(57) ABSTRACT

An apparatus can include a first flexible member having first and second ends and a first body extending therebetween that defines a first passage portion. A second flexible member can include first and second ends and a second body extending therebetween that defines a second passage portion. The first end of the first flexible member can pass into and through the second passage portion in a first direction such that the first end extends outside of the second passage portion. The first end of the second flexible member can pass into and through the first passage portion in a second direction such that the first end of the second flexible member extends outside of the first passage portion to form a self-locking adjustable flexible member construct. Applying tension to the first ends can draw the passage portions and corresponding second ends toward each other.

21 Claims, 23 Drawing Sheets

Related U.S. Application Data is a continuation-in-part of application No. 12/938,902, filed on Nov. 3, 2010, now Pat. No. 8,597,327, which is a continuation-in-part of application No. 12/915,962, filed on Oct. 29, 2010, now Pat. No. 8,562,647, which is a continuation-in-part of application No. 12/719,337, filed on Mar. 8, 2010, now Pat. No. 9,078,644, which is a continuation-in-part of application No. 12/489,168, filed on Jun. 22, 2009, now Pat. No. 8,361,113, which is a continuation-in-part of application No. 12/474,802, filed on May 29, 2009, now Pat. No. 8,088,130, which is a continuation-in-part of application No. 12/196,405, filed on Aug. 22, 2008, now Pat. No. 8,128,658, and a continuation-in-part of application No. 12/196,407, filed on Aug. 22, 2008, now Pat. No. 8,137,382, and a continuation-in-part of application No. 12/196,410, filed on Aug. 22, 2008, now Pat. No. 8,118,836, and a continuation-in-part of application No. 11/541,506, filed on Sep. 29, 2006, now Pat. No. 7,601,165, application No. 13/288,459, filed on Nov. 3, 2011, which is a continuation-in-part of application No. 12/570,854, filed on Sep. 30, 2009, now Pat. No. 8,303,604, which is a continuation-in-part of application No. 12/014,399, filed on Jan. 15, 2008, now Pat. No. 7,909,851, which is a continuation-in-part of application No. 11/347,661, filed on Feb. 3, 2006, now Pat. No. 7,749,250, application No. 13/288,459, which is a continuation-in-part of application No. 12/702,067, filed on Feb. 8, 2010, now Pat. No. 8,672,968, which is a continuation of application No. 11/541,505, filed on Sep. 29, 2006, now Pat. No. 7,658,751, application No. 13/288,459, filed on Nov. 3, 2011, which is a continuation-in-part of application No. 13/102,182, filed on May 6, 2011, now Pat. No. 8,231,654, which is a division of application No. 12/196,398, filed on Aug. 22, 2008, now Pat. No. 7,959,650, which is a continuation-in-part of application No. 11/784,821, filed on Apr. 10, 2007, now Pat. No. 9,017,381.

(51) Int. Cl.
*A61F 2/08* (2006.01)
*A61B 17/06* (2006.01)
*A61B 17/82* (2006.01)

(52) U.S. Cl.
CPC .............. *A61B2017/06057* (2013.01); *A61B 2017/06185* (2013.01); *A61F 2002/087* (2013.01); *A61F 2002/0852* (2013.01); *A61F 2002/0882* (2013.01)

(56) References Cited

U.S. PATENT DOCUMENTS

| | | |
|---|---|---|
| 65,499 A | 6/1867 | Miller |
| 126,366 A | 4/1872 | Wills |
| 233,475 A | 10/1880 | Cook et al. |
| 261,501 A | 7/1882 | Vandermark |
| 268,407 A | 12/1882 | Hughes |
| 330,087 A | 11/1885 | Binns |
| 394,739 A | 12/1888 | Toulmin |
| 417,805 A | 12/1889 | Beaman |
| 487,304 A | 12/1892 | Todd |
| 862,710 A | 6/1901 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,635,066 A | 7/1927 | Wells |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| 2,379,629 A | 7/1945 | Eweson |
| 2,397,216 A | 3/1946 | Stellin |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrle |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,081,781 A | 3/1963 | Stermer |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et at |
| 3,209,422 A | 10/1965 | Dritz |
| 3,223,083 A | 12/1965 | Cobey |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,650,274 A | 3/1972 | Edwards et al. |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |

(56) References Cited

U.S. PATENT DOCUMENTS

| | | |
|---|---|---|
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,786,801 A | 1/1974 | Sartorius |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,896,810 A | 7/1975 | Akiyama |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,446 A | 3/1976 | Schofield |
| 3,946,728 A | 3/1976 | Bettex et al. |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,036,101 A | 7/1977 | Burnett |
| 4,050,100 A | 9/1977 | Barry |
| 4,054,954 A | 10/1977 | Nakayama et al. |
| 4,084,478 A | 4/1978 | Simmons |
| 4,085,466 A | 4/1978 | Goodfellow et al. |
| 4,094,313 A | 6/1978 | Komamura et al. |
| 4,099,750 A | 7/1978 | McGrew |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,146,022 A | 3/1979 | Johnson et al. |
| 4,149,277 A | 4/1979 | Bokros |
| 4,157,714 A | 6/1979 | Foltz et al. |
| 4,158,250 A | 6/1979 | Ringwald |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,207,627 A | 6/1980 | Cloutier |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,490 A | 6/1981 | Bivins |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,302,397 A | 11/1981 | Frainier et al. |
| 4,307,723 A | 12/1981 | Finney |
| 4,312,337 A | 1/1982 | Donohue |
| 4,316,469 A | 2/1982 | Kapitanov et al. |
| 4,326,531 A | 4/1982 | Shimonaka et al. |
| 4,344,193 A | 8/1982 | Kenny |
| 4,345,601 A | 8/1982 | Fukuda |
| 4,349,027 A | 9/1982 | DiFrancesco |
| 4,388,921 A | 6/1983 | Sutter et al. |
| 4,400,833 A | 8/1983 | Kurland |
| 4,402,445 A | 9/1983 | Green |
| 4,402,662 A | 9/1983 | Pfefferle |
| 4,409,974 A | 10/1983 | Freedland |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,489,464 A | 12/1984 | Massari et al. |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'Holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs et al. |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,587,963 A | 5/1986 | Leibinger et al. |
| 4,590,928 A | 5/1986 | Hunt et al. |
| 4,595,007 A | 6/1986 | Mericle |
| 4,596,249 A | 6/1986 | Freda et al. |
| 4,597,766 A | 7/1986 | Hilal et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,640,271 A | 2/1987 | Lower |
| 4,641,652 A | 2/1987 | Hutterer et al. |
| 4,649,916 A | 3/1987 | Frimberger |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn et al. |
| 4,662,068 A | 5/1987 | Polonsky |

(56) References Cited

U.S. PATENT DOCUMENTS

| | | |
|---|---|---|
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,696,300 A | 9/1987 | Anderson |
| 4,705,040 A | 11/1987 | Mueller et al. |
| 4,708,132 A | 11/1987 | Silvestrini |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson |
| 4,736,746 A | 4/1988 | Anderson |
| 4,738,255 A | 4/1988 | Goble et al. |
| 4,739,751 A | 4/1988 | Sapega et al. |
| 4,741,330 A | 5/1988 | Hayhurst |
| 4,741,336 A | 5/1988 | Failla et al. |
| 4,744,353 A | 5/1988 | McFarland |
| 4,744,793 A | 5/1988 | Parr et al. |
| 4,750,492 A | 6/1988 | Jacobs |
| 4,751,922 A | 6/1988 | DiPietropolo |
| 4,760,843 A | 8/1988 | Fischer et al. |
| 4,760,844 A | 8/1988 | Kyle |
| 4,760,848 A | 8/1988 | Hasson |
| 4,770,663 A | 9/1988 | Hanslik et al. |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee et al. |
| 4,784,126 A | 11/1988 | Hourahane et al. |
| 4,787,882 A | 11/1988 | Claren et al. |
| 4,790,297 A | 12/1988 | Luque et al. |
| 4,790,850 A | 12/1988 | Dunn et al. |
| 4,793,363 A | 12/1988 | Ausherman et al. |
| 4,809,695 A | 3/1989 | Gwathmey et al. |
| 4,813,406 A | 3/1989 | Ogle, II |
| 4,823,780 A | 4/1989 | Odensten et al. |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,838,282 A | 6/1989 | Strasser et al. |
| 4,841,960 A | 6/1989 | Garner |
| 4,846,835 A | 7/1989 | Grande |
| 4,851,005 A | 7/1989 | Hunt et al. |
| 4,858,601 A | 8/1989 | Glisson |
| 4,858,603 A | 8/1989 | Clemow et al. |
| 4,858,608 A | 8/1989 | McQuilkin et al. |
| 4,860,513 A | 8/1989 | Whitman |
| 4,863,383 A | 9/1989 | Grafelmann et al. |
| 4,870,957 A | 10/1989 | Goble et al. |
| 4,872,450 A | 10/1989 | Austad |
| 4,873,976 A | 10/1989 | Schreiber |
| 4,884,572 A | 12/1989 | Bays et al. |
| 4,887,601 A | 12/1989 | Richards |
| 4,889,110 A | 12/1989 | Galline et al. |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,919,667 A | 4/1990 | Richmond |
| 4,922,897 A | 5/1990 | Sapega et al. |
| 4,923,461 A | 5/1990 | Caspari et al. |
| 4,927,421 A | 5/1990 | Goble et al. |
| 4,946,377 A | 8/1990 | Kovach |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,974,488 A | 12/1990 | Spralja |
| 4,976,736 A | 12/1990 | White et al. |
| 4,978,350 A | 12/1990 | Wagenknecht et al. |
| 4,979,956 A | 12/1990 | Silvestrini |
| 4,983,176 A | 1/1991 | Cushman et al. |
| 4,988,351 A | 1/1991 | Paulos et al. |
| 4,994,074 A | 2/1991 | Bezwada et al. |
| 4,997,433 A | 3/1991 | Goble et al. |
| 5,002,545 A | 3/1991 | Whiteside et al. |
| 5,002,550 A | 3/1991 | Li |
| 5,002,562 A | 3/1991 | Oberlander |
| 5,002,574 A | 3/1991 | May et al. |
| 5,007,921 A | 4/1991 | Brown |
| 5,020,713 A | 6/1991 | Kunreuther |
| 5,028,569 A | 7/1991 | Cihon |
| 5,030,224 A | 7/1991 | Wright et al. |
| 5,030,235 A | 7/1991 | Campbell, Jr. |
| 5,035,701 A | 7/1991 | Kabbara |
| 5,037,422 A | 8/1991 | Hayhurst et al. |
| 5,037,426 A | 8/1991 | Goble et al. |
| 5,041,129 A | 8/1991 | Hayhurst et al. |
| 5,046,513 A | 9/1991 | Gatturna et al. |
| 5,047,030 A | 9/1991 | Draenert et al. |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A | 11/1991 | Gilbertson et al. |
| 5,067,962 A | 11/1991 | Campbell et al. |
| 5,071,420 A | 12/1991 | Paulos et al. |
| 5,074,874 A | 12/1991 | Yoon et al. |
| 5,078,731 A | 1/1992 | Hayhurst |
| 5,078,843 A | 1/1992 | Pratt |
| 5,080,050 A | 1/1992 | Dale |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,087,309 A | 2/1992 | Melton, Jr. |
| 5,089,012 A | 2/1992 | Prou |
| 5,092,866 A | 3/1992 | Breard et al. |
| 5,098,433 A | 3/1992 | Freedland |
| 5,098,435 A | 3/1992 | Stednitz et al. |
| 5,100,415 A | 3/1992 | Hayhurst |
| 5,100,417 A | 3/1992 | Cerier et al. |
| 5,108,433 A | 4/1992 | May et al. |
| 5,112,335 A | 5/1992 | Laboureau et al. |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |
| 5,123,914 A | 6/1992 | Cope |
| 5,127,785 A | 7/1992 | Faucher et al. |
| 5,129,901 A | 7/1992 | Decoste |
| 5,129,902 A | 7/1992 | Goble et al. |
| 5,129,904 A | 7/1992 | Illi et al. |
| 5,129,906 A | 7/1992 | Ross et al. |
| 5,139,498 A | 8/1992 | Astudillo Ley |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,151,104 A | 9/1992 | Kenna |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |

(56) References Cited

U.S. PATENT DOCUMENTS

| | | |
|---|---|---|
| D331,626 S | 12/1992 | Hayhurst et al. |
| 5,169,400 A | 12/1992 | Muhling et al. |
| 5,171,274 A | 12/1992 | Fluckiger et al. |
| 5,176,682 A | 1/1993 | Chow |
| 5,178,629 A | 1/1993 | Kammerer |
| 5,183,458 A | 2/1993 | Marx |
| 5,190,545 A | 3/1993 | Corsi et al. |
| 5,192,282 A | 3/1993 | Draenert et al. |
| 5,197,987 A | 3/1993 | Koch et al. |
| 5,199,135 A | 4/1993 | Gold |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,219,359 A | 6/1993 | McQuilkin et al. |
| 5,222,976 A | 6/1993 | Yoon |
| 5,224,940 A | 7/1993 | Dann et al. |
| 5,224,946 A | 7/1993 | Hayhurst et al. |
| 5,226,914 A | 7/1993 | Caplan et al. |
| 5,230,699 A | 7/1993 | Grasinger |
| 5,232,436 A | 8/1993 | Janevski |
| 5,234,435 A | 8/1993 | Seagrave, Jr. |
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |
| 5,246,441 A | 9/1993 | Ross et al. |
| 5,249,899 A | 10/1993 | Wilson |
| 5,250,053 A | 10/1993 | Snyder |
| 5,258,015 A | 11/1993 | Li et al. |
| 5,258,016 A | 11/1993 | DiPoto et al. |
| 5,258,040 A | 11/1993 | Bruchman et al. |
| 5,261,908 A | 11/1993 | Campbell, Jr. |
| 5,268,001 A | 12/1993 | Nicholson et al. |
| 5,269,160 A | 12/1993 | Wood |
| 5,269,783 A | 12/1993 | Sander |
| 5,269,806 A | 12/1993 | Sardelis et al. |
| 5,269,809 A | 12/1993 | Hayhurst et al. |
| 5,279,311 A | 1/1994 | Snyder |
| 5,281,422 A | 1/1994 | Badylak et al. |
| 5,282,809 A | 2/1994 | Kammerer et al. |
| 5,282,832 A | 2/1994 | Toso et al. |
| 5,282,867 A | 2/1994 | Mikhail |
| 5,282,868 A | 2/1994 | Bahler |
| 5,285,040 A | 2/1994 | Brandberg et al. |
| 5,290,217 A | 3/1994 | Campos |
| 5,290,243 A | 3/1994 | Chodorow et al. |
| 5,306,301 A | 4/1994 | Graf et al. |
| 5,312,410 A | 5/1994 | Miller et al. |
| 5,312,422 A | 5/1994 | Trott |
| 5,312,438 A | 5/1994 | Johnson |
| 5,314,429 A | 5/1994 | Goble |
| 5,318,566 A | 6/1994 | Miller |
| 5,318,575 A | 6/1994 | Chesterfield et al. |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,308 A | 6/1994 | Pierce |
| 5,330,489 A | 7/1994 | Green et al. |
| 5,333,625 A | 8/1994 | Klein |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,339,870 A | 8/1994 | Green et al. |
| 5,342,369 A | 8/1994 | Harryman, II |
| 5,346,462 A | 9/1994 | Barber |
| 5,350,380 A | 9/1994 | Goble et al. |
| RE34,762 E | 10/1994 | Goble et al. |
| 5,354,292 A | 10/1994 | Braeuer et al. |
| 5,354,298 A | 10/1994 | Lee et al. |
| 5,354,299 A | 10/1994 | Coleman |
| 5,356,412 A | 10/1994 | Golds et al. |
| 5,356,413 A | 10/1994 | Martins et al. |
| 5,356,417 A | 10/1994 | Golds |
| 5,358,511 A | 10/1994 | Gatturna et al. |
| 5,360,431 A | 11/1994 | Puno et al. |
| 5,362,294 A | 11/1994 | Seitzinger |
| 5,362,911 A | 11/1994 | Cevasco |
| 5,364,400 A | 11/1994 | Rego, Jr. et al. |
| 5,366,461 A | 11/1994 | Blasnik |
| 5,368,599 A | 11/1994 | Hirsch et al. |
| 5,370,646 A | 12/1994 | Reese et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,374,269 A | 12/1994 | Rosenberg |
| 5,379,492 A | 1/1995 | Glesser |
| 5,383,878 A | 1/1995 | Roger et al. |
| 5,383,904 A | 1/1995 | Totakura et al. |
| 5,385,567 A | 1/1995 | Goble |
| 5,391,171 A | 2/1995 | Schmieding |
| 5,391,176 A | 2/1995 | de la Torre |
| 5,391,182 A | 2/1995 | Chin |
| 5,393,302 A | 2/1995 | Clark et al. |
| RE34,871 E | 3/1995 | McGuire et al. |
| 5,395,374 A | 3/1995 | Miller et al. |
| 5,397,356 A | 3/1995 | Goble et al. |
| 5,403,328 A | 4/1995 | Shallman |
| 5,403,329 A | 4/1995 | Hinchcliffe |
| 5,403,348 A | 4/1995 | Bonutti |
| 5,405,359 A | 4/1995 | Pierce |
| 5,411,550 A | 5/1995 | Herweck et al. |
| 5,415,658 A | 5/1995 | Kilpela et al. |
| 5,417,690 A | 5/1995 | Sennett et al. |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,824 A | 6/1995 | Akerfeldt et al. |
| 5,423,860 A | 6/1995 | Lizardi et al. |
| 5,425,733 A | 6/1995 | Schmieding |
| 5,425,766 A | 6/1995 | Bowald et al. |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,721 A | 10/1995 | Legrand |
| 5,456,722 A | 10/1995 | McLeod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson et al. |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |

(56) References Cited

U.S. PATENT DOCUMENTS

| | | |
|---|---|---|
| 5,472,452 A | 12/1995 | Trott |
| 5,474,565 A | 12/1995 | Trott |
| 5,474,568 A | 12/1995 | Scott |
| 5,474,572 A | 12/1995 | Hayhurst |
| 5,476,465 A | 12/1995 | Preissman |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,484,442 A | 1/1996 | Melker et al. |
| 5,486,197 A | 1/1996 | Le et al. |
| 5,486,359 A | 1/1996 | Caplan et al. |
| 5,489,210 A | 2/1996 | Hanosh |
| 5,490,750 A | 2/1996 | Gundy |
| 5,495,974 A | 3/1996 | Deschenes et al. |
| 5,496,290 A | 3/1996 | Ackerman |
| 5,496,331 A | 3/1996 | Xu et al. |
| 5,496,348 A | 3/1996 | Bonutti |
| 5,498,302 A | 3/1996 | Davidson |
| 5,500,000 A | 3/1996 | Feagin et al. |
| 5,505,735 A | 4/1996 | Li |
| 5,505,736 A | 4/1996 | Reimels et al. |
| 5,507,754 A | 4/1996 | Green et al. |
| 5,520,691 A | 5/1996 | Branch |
| 5,520,694 A | 5/1996 | Dance et al. |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,843 A | 6/1996 | Zang |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,531,759 A | 7/1996 | Kensey et al. |
| 5,534,012 A | 7/1996 | Bonutti |
| 5,534,033 A | 7/1996 | Simpson |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A | 8/1996 | Kensey et al. |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,664 A | 10/1996 | Durlacher et al. |
| 5,562,668 A | 10/1996 | Johnson |
| 5,562,669 A | 10/1996 | McGuire |
| 5,562,683 A | 10/1996 | Chan |
| 5,562,685 A | 10/1996 | Mollenauer et al. |
| 5,562,686 A | 10/1996 | Sauer et al. |
| 5,569,269 A | 10/1996 | Hart et al. |
| 5,569,305 A | 10/1996 | Bonutti |
| 5,569,306 A | 10/1996 | Thal |
| 5,570,706 A | 11/1996 | Howell |
| 5,571,090 A | 11/1996 | Sherts |
| 5,571,104 A | 11/1996 | Li |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,547 A | 11/1996 | LeVeen et al. |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis et al. |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,607,430 A | 3/1997 | Bailey |
| 5,613,971 A | 3/1997 | Lower et al. |
| 5,618,290 A | 4/1997 | Toy et al. |
| 5,626,611 A | 5/1997 | Liu et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,745 A | 5/1997 | Schwartz |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle et al. |
| 5,643,273 A | 7/1997 | Clark |
| 5,643,295 A | 7/1997 | Yoon |
| 5,643,319 A | 7/1997 | Green et al. |
| 5,643,320 A | 7/1997 | Lower et al. |
| 5,643,321 A | 7/1997 | McDevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,959 A | 7/1997 | Hannam et al. |
| 5,649,960 A | 7/1997 | Pavletic |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,662,677 A | 9/1997 | Wimmer |
| 5,662,681 A | 9/1997 | Nash et al. |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper et al. |
| 5,681,334 A | 10/1997 | Evans et al. |
| 5,681,352 A | 10/1997 | Clancy, III et al. |
| 5,683,404 A | 11/1997 | Johnson |
| 5,683,419 A | 11/1997 | Thal |
| 5,688,284 A | 11/1997 | Chervitz et al. |
| 5,688,285 A | 11/1997 | Yamada et al. |
| 5,690,655 A | 11/1997 | Hart et al. |
| 5,690,676 A | 11/1997 | DiPoto et al. |
| 5,690,678 A | 11/1997 | Johnson |
| 5,693,046 A | 12/1997 | Songer et al. |
| 5,695,497 A | 12/1997 | Stahelin et al. |
| 5,697,929 A | 12/1997 | Mellinger |
| 5,699,657 A | 12/1997 | Paulson |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,709,708 A | 1/1998 | Thal |
| 5,711,969 A | 1/1998 | Patel et al. |
| 5,713,005 A | 1/1998 | Proebsting |
| 5,713,897 A | 2/1998 | Goble et al. |
| 5,713,904 A | 2/1998 | Errico et al. |
| 5,713,905 A | 2/1998 | Goble et al. |
| 5,713,921 A | 2/1998 | Bonutti |
| 5,715,578 A | 2/1998 | Knudson |
| 5,716,359 A | 2/1998 | Ojima et al. |
| 5,716,397 A | 2/1998 | Myers |

(56) References Cited

U.S. PATENT DOCUMENTS

| | | |
|---|---|---|
| 5,716,616 A | 2/1998 | Prockop et al. |
| 5,718,717 A | 2/1998 | Bonutti |
| 5,720,747 A | 2/1998 | Burke |
| 5,720,765 A | 2/1998 | Thal |
| 5,720,766 A | 2/1998 | Zang et al. |
| 5,722,976 A | 3/1998 | Brown |
| 5,723,331 A | 3/1998 | Tubo et al. |
| 5,725,529 A | 3/1998 | Nicholson et al. |
| 5,725,549 A | 3/1998 | Lam |
| 5,725,556 A | 3/1998 | Moser et al. |
| 5,725,557 A | 3/1998 | Gatturna et al. |
| 5,725,581 A | 3/1998 | Brånemark |
| 5,725,582 A | 3/1998 | Bevan et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,260 A | 4/1998 | Songer et al. |
| 5,741,281 A | 4/1998 | Martin et al. |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | de la Torre et al. |
| 5,755,791 A | 5/1998 | Whitson et al. |
| 5,766,176 A | 6/1998 | Duncan |
| 5,766,218 A | 6/1998 | Arnott |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,776,200 A | 7/1998 | Johnson et al. |
| 5,782,845 A | 7/1998 | Shewchuk |
| 5,782,862 A | 7/1998 | Bonutti |
| 5,782,864 A | 7/1998 | Lizardi |
| 5,782,866 A | 7/1998 | Wenstrom, Jr. |
| 5,782,925 A | 7/1998 | Collazo et al. |
| 5,785,714 A | 7/1998 | Morgan et al. |
| 5,786,217 A | 7/1998 | Tubo et al. |
| 5,792,142 A | 8/1998 | Galitzer |
| 5,792,149 A | 8/1998 | Sherts et al. |
| 5,796,127 A | 8/1998 | Hayafuji et al. |
| 5,797,913 A | 8/1998 | Dambreville et al. |
| 5,797,915 A | 8/1998 | Pierson, III et al. |
| 5,797,916 A | 8/1998 | McDowell |
| 5,797,928 A | 8/1998 | Kogasaka |
| 5,800,407 A | 9/1998 | Eldor et al. |
| 5,810,824 A | 9/1998 | Chan |
| 5,810,848 A | 9/1998 | Hayhurst |
| 5,811,094 A | 9/1998 | Caplan et al. |
| 5,814,056 A | 9/1998 | Prosst et al. |
| 5,814,069 A | 9/1998 | Schulze et al. |
| 5,814,070 A | 9/1998 | Borzone et al. |
| 5,814,071 A | 9/1998 | Mcdevitt et al. |
| 5,814,072 A | 9/1998 | Bonutti |
| 5,814,073 A | 9/1998 | Bonutti |
| 5,817,095 A | 10/1998 | Smith |
| 5,823,980 A | 10/1998 | Kopfer |
| 5,824,011 A | 10/1998 | Stone et al. |
| 5,824,066 A | 10/1998 | Gross |
| 5,830,234 A | 11/1998 | Wojciechowicz et al. |
| 5,836,955 A | 11/1998 | Buelna et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,849,012 A | 12/1998 | Abboudi |
| 5,860,947 A | 1/1999 | Stamler |
| 5,860,973 A | 1/1999 | Michelson |
| 5,860,978 A | 1/1999 | McDevitt et al. |
| 5,868,740 A | 2/1999 | LeVeen et al. |
| 5,868,748 A | 2/1999 | Burke |
| 5,868,789 A | 2/1999 | Huebner |
| 5,871,456 A | 2/1999 | Armstrong et al. |
| 5,871,484 A | 2/1999 | Spievack et al. |
| 5,871,486 A | 2/1999 | Huebner et al. |
| 5,871,490 A | 2/1999 | Schulze et al. |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,938 A | 5/1999 | Sklar et al. |
| 5,906,934 A | 5/1999 | Grande et al. |
| 5,908,421 A | 6/1999 | Beger et al. |
| 5,908,436 A | 6/1999 | Cuschieri et al. |
| 5,910,148 A | 6/1999 | Reimels et al. |
| 5,911,721 A | 6/1999 | Nicholson et al. |
| 5,916,557 A | 6/1999 | Berlowitz-tarrant et al. |
| 5,918,604 A | 7/1999 | Whelan |
| 5,921,986 A | 7/1999 | Bonutti |
| 5,925,008 A | 7/1999 | Douglas |
| 5,928,231 A | 7/1999 | Klein et al. |
| 5,928,267 A | 7/1999 | Bonutti et al. |
| 5,928,286 A | 7/1999 | Ashby et al. |
| RE36,289 E | 8/1999 | Le et al. |
| 5,931,838 A | 8/1999 | Vito |
| 5,931,844 A | 8/1999 | Thompson et al. |
| 5,931,869 A | 8/1999 | Boucher et al. |
| 5,935,119 A | 8/1999 | Guy et al. |
| 5,935,133 A | 8/1999 | Wagner et al. |
| 5,935,134 A | 8/1999 | Pedlick et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,947,999 A | 9/1999 | Groiso |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | DiPoto et al. |
| 5,961,520 A | 10/1999 | Beck, Jr. et al. |
| 5,961,521 A | 10/1999 | Roger et al. |
| 5,961,524 A | 10/1999 | Crombie |
| 5,963,869 A | 10/1999 | Fehnel |
| 5,964,764 A | 10/1999 | West, Jr. et al. |
| 5,964,767 A | 10/1999 | Tapia et al. |
| 5,964,769 A | 10/1999 | Wagner et al. |
| 5,964,783 A | 10/1999 | Grafton et al. |
| 5,968,045 A | 10/1999 | Frazier |
| 5,968,047 A | 10/1999 | Reed |
| 5,968,077 A | 10/1999 | Wojciechowicz et al. |
| 5,970,697 A | 10/1999 | Jacobs et al. |
| 5,972,006 A | 10/1999 | Sciaino, Jr. |
| 5,976,125 A | 11/1999 | Graham |
| 5,976,127 A | 11/1999 | Lax |
| 5,980,473 A | 11/1999 | Korakianitis et al. |
| 5,980,524 A | 11/1999 | Justin et al. |
| 5,980,539 A | 11/1999 | Kontos |
| 5,980,548 A | 11/1999 | Evans et al. |
| 5,980,558 A | 11/1999 | Wiley |
| 5,980,559 A | 11/1999 | Bonutti |
| 5,989,252 A | 11/1999 | Fumex |
| 5,989,256 A | 11/1999 | Kuslich et al. |
| 5,989,282 A | 11/1999 | Bonutti |
| 5,989,294 A | 11/1999 | Marlow |
| 5,993,452 A | 11/1999 | Vandewalle |
| 5,993,476 A | 11/1999 | Groiso |
| 5,997,542 A | 12/1999 | Burke |
| 5,997,552 A | 12/1999 | Person et al. |

(56) References Cited

U.S. PATENT DOCUMENTS

| | | |
|---|---|---|
| 5,997,575 A | 12/1999 | Whitson et al. |
| 6,001,100 A | 12/1999 | Sherman et al. |
| 6,001,106 A | 12/1999 | Ryan et al. |
| 6,004,351 A | 12/1999 | Tomita et al. |
| 6,004,352 A | 12/1999 | Buni |
| 6,007,538 A | 12/1999 | Levin |
| 6,007,567 A | 12/1999 | Bonutti |
| 6,010,525 A | 1/2000 | Bonutti et al. |
| 6,013,103 A | 1/2000 | Kaufman et al. |
| 6,016,727 A | 1/2000 | Morgan |
| 6,019,767 A | 2/2000 | Howell |
| 6,022,352 A | 2/2000 | Vandewalle |
| 6,022,373 A | 2/2000 | Li |
| 6,023,661 A | 2/2000 | Sottery |
| 6,024,758 A | 2/2000 | Thal |
| 6,027,523 A | 2/2000 | Schmieding |
| 6,030,410 A | 2/2000 | Zurbrugg |
| 6,033,429 A | 3/2000 | Magovern |
| 6,033,430 A | 3/2000 | Bonutti |
| 6,036,695 A | 3/2000 | Smith |
| 6,039,753 A | 3/2000 | Meislin |
| 6,041,485 A | 3/2000 | Pedlick et al. |
| 6,042,601 A | 3/2000 | Smith |
| 6,042,609 A | 3/2000 | Giordano et al. |
| 6,045,551 A | 4/2000 | Bonutti |
| 6,045,571 A | 4/2000 | Hill et al. |
| 6,045,572 A | 4/2000 | Johnson et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,051,007 A | 4/2000 | Hogendijk et al. |
| 6,053,916 A | 4/2000 | Moore |
| 6,053,921 A | 4/2000 | Wagner et al. |
| 6,056,752 A | 5/2000 | Roger |
| 6,056,772 A | 5/2000 | Bonutti |
| 6,056,773 A | 5/2000 | Bonutti |
| 6,059,817 A | 5/2000 | Bonutti et al. |
| 6,059,818 A | 5/2000 | Johnson et al. |
| 6,062,344 A | 5/2000 | Okabe et al. |
| 6,066,173 A | 5/2000 | McKernan et al. |
| 6,068,648 A | 5/2000 | Cole et al. |
| 6,071,305 A | 6/2000 | Brown et al. |
| 6,074,403 A | 6/2000 | Nord |
| 6,077,277 A | 6/2000 | Mollenauer et al. |
| 6,077,292 A | 6/2000 | Bonutti |
| 6,080,185 A | 6/2000 | Johnson et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,102,934 A | 8/2000 | Li |
| 6,106,545 A | 8/2000 | Egan |
| 6,110,128 A | 8/2000 | Andelin et al. |
| 6,110,207 A | 8/2000 | Eichhorn et al. |
| 6,113,604 A | 9/2000 | Whittaker et al. |
| 6,117,160 A | 9/2000 | Bonutti |
| 6,117,162 A | 9/2000 | Schmieding et al. |
| 6,123,710 A | 9/2000 | Pinczewski et al. |
| 6,127,596 A | 10/2000 | Brown et al. |
| 6,132,433 A | 10/2000 | Whelan |
| 6,132,437 A | 10/2000 | Omurtag et al. |
| 6,136,010 A | 10/2000 | Modesitt et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,150,163 A | 11/2000 | McPherson et al. |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,171,310 B1 | 1/2001 | Giordano et al. |
| 6,179,840 B1 | 1/2001 | Bowman |
| 6,183,461 B1 | 2/2001 | Matsuura et al. |
| 6,183,737 B1 | 2/2001 | Zaleske et al. |
| 6,187,025 B1 | 2/2001 | Machek |
| 6,190,348 B1 | 2/2001 | Tiemann et al. |
| 6,190,401 B1 | 2/2001 | Green et al. |
| 6,190,411 B1 | 2/2001 | Lo et al. |
| 6,193,754 B1 | 2/2001 | Seedhom |
| 6,200,318 B1 | 3/2001 | Har-Shai et al. |
| 6,200,329 B1 | 3/2001 | Fung et al. |
| 6,200,330 B1 | 3/2001 | Benderev et al. |
| 6,200,606 B1 | 3/2001 | Peterson et al. |
| 6,200,685 B1 | 3/2001 | Davidson |
| 6,203,556 B1 | 3/2001 | Evans et al. |
| 6,203,563 B1 | 3/2001 | Fernandez |
| 6,203,565 B1 | 3/2001 | Bonutti et al. |
| 6,203,572 B1 | 3/2001 | Johnson et al. |
| 6,203,576 B1 | 3/2001 | Afriat et al. |
| 6,206,883 B1 | 3/2001 | Tunc |
| 6,210,376 B1 | 4/2001 | Grayson |
| 6,210,381 B1 | 4/2001 | Morse |
| 6,214,007 B1 | 4/2001 | Anderson |
| 6,214,012 B1 | 4/2001 | Karpman et al. |
| 6,217,580 B1 | 4/2001 | Levin |
| 6,221,107 B1 | 4/2001 | Steiner et al. |
| 6,228,096 B1 | 5/2001 | Marchand |
| 6,231,592 B1 | 5/2001 | Bonutti et al. |
| 6,234,980 B1 | 5/2001 | Bell |
| 6,235,057 B1 | 5/2001 | Roger et al. |
| 6,235,058 B1 | 5/2001 | Huene |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,254,604 B1 | 7/2001 | Howell |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 6,283,973 B1 | 9/2001 | Hubbard et al. |
| 6,283,996 B1 | 9/2001 | Chervitz et al. |
| 6,287,307 B1 | 9/2001 | Abboudi |
| 6,287,325 B1 | 9/2001 | Bonutti |
| 6,293,929 B1 | 9/2001 | Smith et al. |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,302,899 B1 | 10/2001 | Johnson et al. |
| 6,302,915 B1 | 10/2001 | Cooney, III et al. |
| 6,303,158 B1 | 10/2001 | Odgaard et al. |
| 6,306,156 B1 | 10/2001 | Clark |
| 6,306,158 B1 | 10/2001 | Bartlett |
| 6,306,159 B1 | 10/2001 | Schwartz et al. |
| 6,309,124 B1 | 10/2001 | Gueret |
| 6,309,405 B1 | 10/2001 | Bonutti |
| 6,312,448 B1 | 11/2001 | Bonutti |
| 6,315,788 B1 | 11/2001 | Roby |
| 6,319,224 B1 | 11/2001 | Stout et al. |
| 6,319,271 B1 | 11/2001 | Schwartz et al. |
| 6,328,758 B1 | 12/2001 | Tornier et al. |
| 6,334,064 B1 | 12/2001 | Fiddian-green |
| 6,342,060 B1 | 1/2002 | Adams |
| 6,343,531 B2 | 2/2002 | Amis |

(56) References Cited

U.S. PATENT DOCUMENTS

| | | |
|---|---|---|
| 6,355,066 B1 | 3/2002 | Kim |
| 6,358,270 B1 | 3/2002 | Lemer |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,111 B1 | 5/2002 | Barber |
| 6,387,113 B1 | 5/2002 | Hawkins et al. |
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,456 B1 | 6/2002 | Slate et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,073 B2 | 7/2002 | Bowman |
| 6,423,088 B1 | 7/2002 | Fenton, Jr. |
| 6,425,924 B1 | 7/2002 | Rousseau |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,458,161 B1 | 10/2002 | Gibbs et al. |
| 6,461,373 B2 | 10/2002 | Wyman et al. |
| 6,464,690 B1 | 10/2002 | Castaneda et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,478,753 B2 | 11/2002 | Reay-Young |
| 6,482,210 B1 | 11/2002 | Skiba et al. |
| 6,485,504 B1 | 11/2002 | Johnson et al. |
| 6,491,714 B1 | 12/2002 | Bennett |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex |
| 6,511,499 B2 | 1/2003 | Schmieding et al. |
| 6,514,274 B1 | 2/2003 | Boucher et al. |
| 6,517,542 B1 | 2/2003 | Papay et al. |
| 6,517,552 B1 | 2/2003 | Nord et al. |
| 6,517,564 B1 | 2/2003 | Grafton et al. |
| 6,517,578 B2 | 2/2003 | Hein |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,540,783 B1 | 4/2003 | Whittaker et al. |
| 6,543,094 B2 | 4/2003 | D'Addario |
| 6,544,281 B2 | 4/2003 | ElAttrache et al. |
| 6,547,564 B1 | 4/2003 | Hansson et al. |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,551,353 B1 | 4/2003 | Baker et al. |
| 6,553,802 B2 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,558,389 B2 | 5/2003 | Clark et al. |
| 6,562,071 B2 | 5/2003 | Jarvinen |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,572,655 B1 | 6/2003 | Johnson |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,592,622 B1 | 7/2003 | Ferguson |
| 6,595,911 B2 | 7/2003 | LoVuolo |
| 6,599,289 B1 | 7/2003 | Bojarski et al. |
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,626,930 B1 | 9/2003 | Allen et al. |
| 6,629,977 B1 | 10/2003 | Wolf |
| 6,629,997 B2 | 10/2003 | Mansmann |
| 6,632,245 B2 | 10/2003 | Kim |
| 6,635,073 B2 | 10/2003 | Bonutti |
| 6,638,279 B2 | 10/2003 | Bonutti |
| 6,638,286 B1 | 10/2003 | Burbank et al. |
| 6,638,312 B2 | 10/2003 | Plouhar et al. |
| 6,641,596 B1 | 11/2003 | Lizardi |
| 6,641,597 B2 | 11/2003 | Burkhart et al. |
| 6,645,169 B1 | 11/2003 | Slate et al. |
| 6,645,211 B2 | 11/2003 | Magana |
| 6,645,227 B2 | 11/2003 | Fallin et al. |
| 6,648,903 B1 | 11/2003 | Pierson, III |
| 6,648,921 B2 | 11/2003 | Anderson et al. |
| 6,652,450 B2 | 11/2003 | Neisz et al. |
| 6,652,533 B2 | 11/2003 | O'neil |
| 6,652,560 B1 | 11/2003 | Gerke et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,666,877 B2 | 12/2003 | Morgan et al. |
| 6,669,707 B1 | 12/2003 | Swanstrom et al. |
| 6,679,889 B1 | 1/2004 | West, Jr. et al. |
| 6,682,533 B1 | 1/2004 | Dinsdale et al. |
| 6,682,549 B2 | 1/2004 | Bartlett |
| 6,685,728 B2 | 2/2004 | Sinnott et al. |

(56) References Cited

U.S. PATENT DOCUMENTS

| | | |
|---|---|---|
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,692,516 B2 | 2/2004 | West, Jr. et al. |
| 6,695,852 B2 | 2/2004 | Gleason |
| 6,712,849 B2 | 3/2004 | Re et al. |
| 6,712,859 B2 | 3/2004 | Rousseau et al. |
| 6,716,190 B1 | 4/2004 | Glines et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,780 B2 | 6/2004 | Stout et al. |
| 6,752,810 B1 | 6/2004 | Gao et al. |
| 6,752,831 B2 | 6/2004 | Sybert et al. |
| 6,755,836 B1 | 6/2004 | Lewis |
| 6,755,868 B2 | 6/2004 | Rousseau |
| 6,761,722 B2 | 7/2004 | Cole et al. |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,790,210 B1 | 9/2004 | Cragg et al. |
| 6,793,595 B1 | 9/2004 | Monnet |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,835,377 B2 | 12/2004 | Goldberg et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,887,271 B2 | 5/2005 | Justin et al. |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,911,202 B2 | 6/2005 | Amir et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,939,379 B2 | 9/2005 | Sklar |
| 6,949,102 B2 | 9/2005 | Andrews |
| 6,951,565 B2 | 10/2005 | Keane et al. |
| 6,960,214 B2 | 11/2005 | Burkinshaw |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,984,237 B2 | 1/2006 | Hatch et al. |
| 6,986,781 B2 | 1/2006 | Smith |
| 6,989,034 B2 | 1/2006 | Hammer et al. |
| 6,994,719 B2 | 2/2006 | Grafton |
| 6,994,725 B1 | 2/2006 | Goble |
| 7,001,429 B2 | 2/2006 | Ferguson |
| 7,004,959 B2 | 2/2006 | Bonutti |
| 7,008,451 B2 | 3/2006 | Justin et al. |
| 7,048,754 B2 | 5/2006 | Martin et al. |
| 7,052,499 B2 | 5/2006 | Steger et al. |
| 7,066,942 B2 | 6/2006 | Treace |
| 7,066,944 B2 | 6/2006 | Laufer et al. |
| 7,081,126 B2 | 7/2006 | McDevitt et al. |
| 7,083,638 B2 | 8/2006 | Foerster |
| 7,087,064 B1 | 8/2006 | Hyde |
| 7,087,073 B2 | 8/2006 | Bonutti |
| 7,097,654 B1 | 8/2006 | Freedland |
| 7,105,010 B2 | 9/2006 | Hart et al. |
| 7,112,221 B2 | 9/2006 | Harris et al. |
| 7,118,578 B2 | 10/2006 | West, Jr. et al. |
| 7,118,583 B2 | 10/2006 | O'Quinn et al. |
| 7,125,421 B2 | 10/2006 | Tremulis et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,148,209 B2 | 12/2006 | Hoemann et al. |
| 7,153,127 B2 | 12/2006 | Struble et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,160,285 B2 | 1/2007 | Sklar et al. |
| 7,160,333 B2 | 1/2007 | Plouhar et al. |
| 7,172,626 B1 | 2/2007 | Andrews |
| 7,179,259 B1 | 2/2007 | Gibbs |
| 7,201,722 B2 | 4/2007 | Krueger |
| 7,207,993 B1 | 4/2007 | Baldwin et al. |
| 7,255,675 B2 | 8/2007 | Gertner et al. |
| 7,255,700 B2 | 8/2007 | Kaiser et al. |
| 7,255,715 B2 | 8/2007 | Metzger |
| 7,261,716 B2 | 8/2007 | Strobel et al. |
| 7,264,634 B2 | 9/2007 | Schmieding |
| 7,279,008 B2 | 10/2007 | Brown et al. |
| 7,285,124 B2 | 10/2007 | Foerster |
| 7,291,177 B2 | 11/2007 | Gibbs |
| 7,303,577 B1 | 12/2007 | Dean |
| 7,306,417 B2 | 12/2007 | Dorstewitz |
| 7,309,355 B2 | 12/2007 | Donnelly et al. |
| 7,326,222 B2 | 2/2008 | Dreyfuss et al. |
| 7,329,272 B2 | 2/2008 | Burkhart et al. |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,465,308 B2 | 12/2008 | Sikora et al. |
| 7,468,074 B2 | 12/2008 | Caborn et al. |
| 7,481,814 B1 | 1/2009 | Metzger |
| 7,485,149 B1 | 2/2009 | White |
| 7,494,506 B2 | 2/2009 | Brulez et al. |
| D587,807 S | 3/2009 | Wolf et al. |
| 7,500,983 B1 | 3/2009 | Kaiser et al. |
| 7,513,910 B2 | 4/2009 | Buskirk et al. |
| 7,572,275 B2 | 8/2009 | Fallin et al. |
| 7,572,298 B2 | 8/2009 | Roller et al. |
| 7,578,825 B2 | 8/2009 | Huebner |
| 7,585,311 B2 | 9/2009 | Green et al. |
| 7,591,823 B2 | 9/2009 | Tipirneni |
| 7,597,705 B2 | 10/2009 | Forsberg et al. |
| 7,601,165 B2 | 10/2009 | Stone |
| 7,604,636 B1 | 10/2009 | Walters et al. |
| 7,608,092 B1 | 10/2009 | Schaffhausen |
| 7,608,098 B1 | 10/2009 | Stone et al. |
| 7,615,076 B2 | 11/2009 | Cauthen, III et al. |
| 7,621,937 B2 | 11/2009 | Pipenhagen et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 | 2/2010 | Stone et al. |
| 7,670,279 B2 | 3/2010 | Gertner |
| 7,678,123 B2 | 3/2010 | Chanduszko |

(56) References Cited

U.S. PATENT DOCUMENTS

| | | |
|---|---|---|
| 7,691,112 B2 | 4/2010 | Chanduszko et al. |
| 7,695,493 B2 | 4/2010 | Saadat et al. |
| 7,695,503 B1 | 4/2010 | Kaiser et al. |
| 7,703,372 B1 | 4/2010 | Shakespeare |
| 7,713,285 B1 | 5/2010 | Stone et al. |
| 7,717,929 B2 | 5/2010 | Fallman |
| 7,731,732 B2 | 6/2010 | Ken |
| 7,736,364 B2 | 6/2010 | Stone |
| 7,736,379 B2 | 6/2010 | Ewers et al. |
| 7,749,250 B2 | 7/2010 | Stone et al. |
| 7,758,594 B2 | 7/2010 | Lamson et al. |
| 7,758,611 B2 | 7/2010 | Kato |
| 7,762,942 B2 | 7/2010 | Neisz et al. |
| 7,771,482 B1 | 8/2010 | Karmon |
| 7,776,041 B1 | 8/2010 | Walters |
| 7,790,945 B1 | 9/2010 | Watson, Jr. |
| 7,803,173 B2 | 9/2010 | Burkhart et al. |
| 7,819,895 B2 | 10/2010 | Ginn et al. |
| 7,828,820 B2 | 11/2010 | Stone et al. |
| 7,828,850 B2 | 11/2010 | Cauthen, III et al. |
| 7,856,698 B2 | 12/2010 | Hays |
| 7,857,830 B2 | 12/2010 | Stone et al. |
| 7,867,252 B2 | 1/2011 | Criscuolo et al. |
| 7,867,264 B2 | 1/2011 | McDevitt et al. |
| 7,875,058 B2 | 1/2011 | Holmes, Jr. |
| 7,878,058 B2 | 2/2011 | Blendinger et al. |
| 7,887,586 B2 | 2/2011 | Linares |
| 7,896,907 B2 | 3/2011 | Mcdevitt et al. |
| 7,905,903 B2 | 3/2011 | Stone et al. |
| 7,905,904 B2 | 3/2011 | Stone et al. |
| 7,909,851 B2 | 3/2011 | Stone et al. |
| 7,914,539 B2 | 3/2011 | Stone et al. |
| 7,938,847 B2 | 5/2011 | Fanton et al. |
| 7,951,198 B2 | 5/2011 | Sucec et al. |
| 7,959,650 B2 | 6/2011 | Kaiser et al. |
| 7,981,140 B2 | 7/2011 | Burkhart |
| 7,998,203 B2 | 8/2011 | Blum |
| 8,034,090 B2 | 10/2011 | Stone et al. |
| 8,062,334 B2 | 11/2011 | Green et al. |
| 8,075,574 B2 | 12/2011 | May et al. |
| 8,088,108 B2 | 1/2012 | Kraft |
| 8,088,130 B2 | 1/2012 | Kaiser et al. |
| 8,114,127 B2 | 2/2012 | West, Jr. |
| 8,114,128 B2 | 2/2012 | Cauldwell et al. |
| 8,118,835 B2 | 2/2012 | Weisel et al. |
| 8,118,836 B2 | 2/2012 | Denham et al. |
| 8,118,868 B2 | 2/2012 | May et al. |
| 8,128,658 B2 | 3/2012 | Kaiser et al. |
| 8,137,354 B2 | 3/2012 | Stone |
| 8,137,382 B2 | 3/2012 | Denham et al. |
| 8,162,997 B2 | 4/2012 | Struhl |
| 8,167,906 B2 | 5/2012 | Cauldwell et al. |
| 8,177,810 B2 | 5/2012 | Ferree |
| 8,202,295 B2 | 6/2012 | Kaplan |
| 8,202,318 B2 | 6/2012 | Willobee |
| 8,221,454 B2 | 7/2012 | Schaffhausen |
| 8,231,654 B2 | 7/2012 | Kaiser et al. |
| 8,251,998 B2 | 8/2012 | Hoeppner et al. |
| 8,252,022 B2 | 8/2012 | Holman et al. |
| 8,273,106 B2 | 9/2012 | Stone et al. |
| 8,292,921 B2 | 10/2012 | Stone et al. |
| 8,298,262 B2 | 10/2012 | Stone et al. |
| 8,298,284 B2 | 10/2012 | Cassani |
| 8,303,604 B2 | 11/2012 | Stone et al. |
| 8,317,825 B2 | 11/2012 | Stone |
| 8,337,525 B2 | 12/2012 | Stone et al. |
| 8,343,155 B2 | 1/2013 | Fisher et al. |
| 8,343,227 B2 | 1/2013 | Metzger et al. |
| 8,361,054 B2 | 1/2013 | Ducharme et al. |
| 8,361,113 B2 | 1/2013 | Stone et al. |
| 8,409,253 B2 | 4/2013 | Stone et al. |
| 8,486,114 B2 | 7/2013 | Gillard et al. |
| 8,500,818 B2 | 8/2013 | Metzger et al. |
| 8,506,597 B2 | 8/2013 | Kaiser et al. |
| 8,551,140 B2 | 10/2013 | Denham et al. |
| 8,562,645 B2 | 10/2013 | Stone et al. |
| 8,562,647 B2 | 10/2013 | Kaiser et al. |
| 8,574,235 B2 | 11/2013 | Stone |
| 8,579,944 B2 | 11/2013 | Holloway et al. |
| 8,597,327 B2 | 12/2013 | Stone et al. |
| 8,608,777 B2 | 12/2013 | Kaiser et al. |
| 8,632,566 B2 | 1/2014 | Olson |
| 8,632,569 B2 | 1/2014 | Stone et al. |
| 8,652,171 B2 | 2/2014 | Stone et al. |
| 8,652,172 B2 * | 2/2014 | Denham et al. ............... 606/232 |
| 8,672,904 B1 | 3/2014 | Schultz |
| 8,672,968 B2 | 3/2014 | Stone et al. |
| 8,672,969 B2 | 3/2014 | Stone et al. |
| 8,702,718 B2 | 4/2014 | Bhatnagar et al. |
| 8,721,650 B2 | 5/2014 | Fanton et al. |
| 8,721,684 B2 | 5/2014 | Denham et al. |
| 8,771,316 B2 | 7/2014 | Denham et al. |
| 8,771,352 B2 | 7/2014 | Conner et al. |
| 8,777,956 B2 | 7/2014 | Hoeppner et al. |
| 8,801,783 B2 | 8/2014 | Stone et al. |
| 8,840,645 B2 | 9/2014 | Denham et al. |
| 8,900,314 B2 | 12/2014 | Metzger et al. |
| 8,926,613 B2 | 1/2015 | Kaiser et al. |
| 8,932,331 B2 | 1/2015 | Kaiser et al. |
| 8,936,621 B2 | 1/2015 | Denham et al. |
| 8,961,548 B2 | 2/2015 | Buser |
| 8,968,364 B2 | 3/2015 | Berelsman et al. |
| 8,998,949 B2 | 4/2015 | Stone et al. |
| 9,005,287 B2 | 4/2015 | Stone |
| 9,017,381 B2 | 4/2015 | Kaiser et al. |
| 9,023,058 B2 | 5/2015 | Jaramillo et al. |
| 9,078,644 B2 | 7/2015 | Stone |
| 9,149,267 B2 | 10/2015 | Norton et al. |
| 9,173,651 B2 | 11/2015 | Stone et al. |
| 9,198,673 B2 | 12/2015 | Stone |
| 9,216,078 B2 | 12/2015 | Conner et al. |
| 9,271,713 B2 | 3/2016 | Denham et al. |
| 9,314,235 B2 | 4/2016 | Bojarski et al. |
| 9,314,241 B2 | 4/2016 | Stone et al. |
| 9,357,991 B2 | 6/2016 | Denham et al. |
| 9,357,992 B2 | 6/2016 | Stone et al. |
| 9,370,350 B2 | 6/2016 | Norton |
| 9,381,013 B2 | 7/2016 | Norton |
| 9,402,621 B2 | 8/2016 | Stone et al. |
| 2001/0002439 A1 | 5/2001 | Bonutti et al. |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0029387 A1 | 10/2001 | Wolf et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051815 A1 | 12/2001 | Esplin |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | ElAttrache et al. |
| 2002/0019649 A1 | 2/2002 | Sikora et al. |
| 2002/0029048 A1 | 3/2002 | Miller |
| 2002/0029066 A1 | 3/2002 | Foerster |
| 2002/0032465 A1 | 3/2002 | Lemer |
| 2002/0045902 A1 | 4/2002 | Bonutti |
| 2002/0052628 A1 | 5/2002 | Bowman |
| 2002/0055780 A1 | 5/2002 | Sklar |
| 2002/0058966 A1 | 5/2002 | Tormala et al. |
| 2002/0068254 A1 | 6/2002 | Campbell |
| 2002/0077629 A1 | 6/2002 | Hoffman et al. |
| 2002/0077659 A1 | 6/2002 | Johnson et al. |
| 2002/0082220 A1 | 6/2002 | Hoemann et al. |
| 2002/0099411 A1 | 7/2002 | Bartlett |
| 2002/0111591 A1 | 8/2002 | Mckinnon et al. |

(56) References Cited

U.S. PATENT DOCUMENTS

| | | |
|---|---|---|
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0156475 A1 | 10/2002 | Lerch et al. |
| 2002/0161401 A1 | 10/2002 | Steiner |
| 2002/0161439 A1 | 10/2002 | Strobel et al. |
| 2002/0165548 A1 | 11/2002 | Jutley |
| 2002/0165611 A1 | 11/2002 | Enzerink et al. |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0177853 A1 | 11/2002 | Chervitz et al. |
| 2002/0188298 A1 | 12/2002 | Chan |
| 2002/0193830 A1 | 12/2002 | Bonutti |
| 2003/0004545 A1 | 1/2003 | Burkhart et al. |
| 2003/0009235 A1 | 1/2003 | Manrique et al. |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0065402 A1 | 4/2003 | Anderson et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1 | 6/2003 | Eichhorn et al. |
| 2003/0120309 A1 | 6/2003 | Colleran et al. |
| 2003/0130670 A1 | 7/2003 | Anderson et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0139752 A1 | 7/2003 | Pasricha et al. |
| 2003/0139775 A1 | 7/2003 | Grafton |
| 2003/0149448 A1 | 8/2003 | Foerster et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0176920 A1 | 9/2003 | Sklar et al. |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208209 A1 | 11/2003 | Gambale et al. |
| 2003/0208210 A1 | 11/2003 | Dreyfuss et al. |
| 2003/0212456 A1 | 11/2003 | Lipchitz et al. |
| 2003/0216809 A1 | 11/2003 | Ferguson |
| 2003/0220646 A1 | 11/2003 | Thelen et al. |
| 2003/0220660 A1 | 11/2003 | Kortenbach et al. |
| 2003/0225459 A1 | 12/2003 | Hammer et al. |
| 2003/0229361 A1 | 12/2003 | Jackson |
| 2003/0229396 A1 | 12/2003 | Andrews |
| 2003/0236555 A1 | 12/2003 | Thornes |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0039389 A1 | 2/2004 | West et al. |
| 2004/0044391 A1 | 3/2004 | Porter |
| 2004/0059357 A1 | 3/2004 | Koseki |
| 2004/0073176 A1 | 4/2004 | Utterberg |
| 2004/0087981 A1 | 5/2004 | Berube et al. |
| 2004/0092936 A1 | 5/2004 | Miller et al. |
| 2004/0093031 A1 | 5/2004 | Burkhart et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0127907 A1 | 7/2004 | Dakin et al. |
| 2004/0133206 A1 | 7/2004 | Stevens et al. |
| 2004/0133211 A1 | 7/2004 | Raskin et al. |
| 2004/0133238 A1 | 7/2004 | Cerier |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0147958 A1 | 7/2004 | Lam et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0181234 A1 | 9/2004 | McDevitt et al. |
| 2004/0182968 A1 | 9/2004 | Gentry |
| 2004/0187314 A1 | 9/2004 | Johnson |
| 2004/0193185 A1 | 9/2004 | McBrayer |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225183 A1 | 11/2004 | Michlitsch et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243180 A1 | 12/2004 | Donnelly et al. |
| 2004/0243235 A1 | 12/2004 | Goh et al. |
| 2004/0249394 A1 | 12/2004 | Morris et al. |
| 2004/0260296 A1 | 12/2004 | Kaiser et al. |
| 2004/0260298 A1 | 12/2004 | Kaiser et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2004/0267317 A1 | 12/2004 | Higgins et al. |
| 2004/0267361 A1 | 12/2004 | Donnelly et al. |
| 2004/0267362 A1 | 12/2004 | Hwang et al. |
| 2005/0004670 A1 | 1/2005 | Gebhardt et al. |
| 2005/0021087 A1 | 1/2005 | Koseki |
| 2005/0021148 A1 | 1/2005 | Gibbs |
| 2005/0027307 A1 | 2/2005 | Schwartz et al. |
| 2005/0033362 A1 | 2/2005 | Grafton |
| 2005/0033363 A1 | 2/2005 | Bojarski et al. |
| 2005/0038426 A1 | 2/2005 | Chan |
| 2005/0049598 A1 | 3/2005 | West, Jr. et al. |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0065526 A1 | 3/2005 | Drew et al. |
| 2005/0070906 A1 | 3/2005 | Clark et al. |
| 2005/0070928 A1 | 3/2005 | Heino et al. |
| 2005/0074495 A1 | 4/2005 | Schwartz et al. |
| 2005/0076478 A1 | 4/2005 | Miyazaki et al. |
| 2005/0085819 A1 | 4/2005 | Ellis et al. |

(56) References Cited

U.S. PATENT DOCUMENTS

| | | |
|---|---|---|
| 2005/0090827 A1 | 4/2005 | Gedebou |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0107882 A1 | 5/2005 | Stone et al. |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125031 A1 | 6/2005 | Pipenhagen et al. |
| 2005/0125036 A1 | 6/2005 | Roby |
| 2005/0125073 A1 | 6/2005 | Orban et al. |
| 2005/0130301 A1 | 6/2005 | Mckay et al. |
| 2005/0131413 A1 | 6/2005 | O'Driscoll et al. |
| 2005/0137600 A1 | 6/2005 | Jacobs et al. |
| 2005/0137624 A1 | 6/2005 | Fallman |
| 2005/0149033 A1 | 7/2005 | McGuire et al. |
| 2005/0149118 A1 | 7/2005 | Koyfman et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0171547 A1 | 8/2005 | Aram |
| 2005/0171603 A1 | 8/2005 | Justin et al. |
| 2005/0171604 A1 | 8/2005 | Michalow |
| 2005/0177237 A1 | 8/2005 | Shappley et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0192632 A1 | 9/2005 | Geissler et al. |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251153 A1 | 11/2005 | Sakamoto et al. |
| 2005/0251159 A1 | 11/2005 | Ewers et al. |
| 2005/0251177 A1 | 11/2005 | Saadat et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0261642 A1 | 11/2005 | Weston |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004364 A1 | 1/2006 | Green et al. |
| 2006/0004410 A1 | 1/2006 | Nobis et al. |
| 2006/0015103 A1 | 1/2006 | Burke |
| 2006/0015106 A1 | 1/2006 | Lerch et al. |
| 2006/0015107 A1 | 1/2006 | Sklar |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0052787 A1 | 3/2006 | Re et al. |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0095130 A1 | 5/2006 | Caborn et al. |
| 2006/0095131 A1 | 5/2006 | Justin et al. |
| 2006/0100627 A1 | 5/2006 | Stone et al. |
| 2006/0100637 A1 | 5/2006 | Rathbun et al. |
| 2006/0106423 A1 | 5/2006 | Weisel et al. |
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122608 A1 | 6/2006 | Fallin et al. |
| 2006/0122611 A1 | 6/2006 | Morales et al. |
| 2006/0135958 A1 | 6/2006 | Marissen et al. |
| 2006/0149258 A1 | 7/2006 | Sousa |
| 2006/0149266 A1 | 7/2006 | Cordasco |
| 2006/0155287 A1 | 7/2006 | Montgomery et al. |
| 2006/0155328 A1 | 7/2006 | Foerster |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0178743 A1 | 8/2006 | Carter |
| 2006/0189993 A1 | 8/2006 | Stone |
| 2006/0190042 A1 | 8/2006 | Stone et al. |
| 2006/0195101 A1 | 8/2006 | Stevens |
| 2006/0195106 A1 | 8/2006 | Jones et al. |
| 2006/0200235 A1 | 9/2006 | Bianchi et al. |
| 2006/0212055 A1 | 9/2006 | Karabey et al. |
| 2006/0229623 A1 | 10/2006 | Bonutti et al. |
| 2006/0229671 A1 | 10/2006 | Steiner et al. |
| 2006/0229676 A1 | 10/2006 | Doll et al. |
| 2006/0235407 A1 | 10/2006 | Wang et al. |
| 2006/0235413 A1 | 10/2006 | Denham et al. |
| 2006/0241624 A1 | 10/2006 | Kizuka et al. |
| 2006/0241776 A1 | 10/2006 | Brown et al. |
| 2006/0241781 A1 | 10/2006 | Brown et al. |
| 2006/0247642 A1 | 11/2006 | Stone et al. |
| 2006/0253130 A1 | 11/2006 | Wolniewicz |
| 2006/0259048 A1 | 11/2006 | Koseki |
| 2006/0259076 A1 | 11/2006 | Burkhart |
| 2006/0264944 A1 | 11/2006 | Cole |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276818 A1 | 12/2006 | Buser et al. |
| 2006/0276841 A1 | 12/2006 | Barbieri et al. |
| 2006/0276896 A1 | 12/2006 | Fallin et al. |
| 2006/0280768 A1 | 12/2006 | Hwang et al. |
| 2006/0280803 A1 | 12/2006 | Kumar et al. |
| 2006/0282082 A1 | 12/2006 | Fanton et al. |
| 2006/0282083 A1 | 12/2006 | Fanton et al. |
| 2006/0282085 A1 | 12/2006 | Stone et al. |
| 2006/0293709 A1 | 12/2006 | Bojarski et al. |
| 2007/0005068 A1 | 1/2007 | Sklar |
| 2007/0005080 A1 | 1/2007 | Wolniewicz et al. |
| 2007/0010857 A1 | 1/2007 | Sugimoto et al. |
| 2007/0016305 A1 | 1/2007 | Chudik |
| 2007/0021779 A1 | 1/2007 | Garvin et al. |
| 2007/0027476 A1 | 2/2007 | Harris et al. |
| 2007/0032800 A1 | 2/2007 | Ortiz et al. |
| 2007/0032823 A1 | 2/2007 | Tegg |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0071568 A1 | 3/2007 | Dorstewitz |
| 2007/0073307 A1 | 3/2007 | Scribner et al. |
| 2007/0073319 A1 | 3/2007 | Mikkaichi et al. |
| 2007/0073322 A1 | 3/2007 | Mikkaichi et al. |
| 2007/0078435 A1 | 4/2007 | Stone et al. |
| 2007/0083236 A1 | 4/2007 | Sikora et al. |
| 2007/0088362 A1 | 4/2007 | Bonutti et al. |
| 2007/0093847 A1 | 4/2007 | Scribner et al. |
| 2007/0100350 A1 | 5/2007 | Deffenbaugh et al. |
| 2007/0112384 A1 | 5/2007 | Conlon et al. |
| 2007/0118217 A1 | 5/2007 | Brulez et al. |
| 2007/0123883 A1 | 5/2007 | Ellis et al. |
| 2007/0123984 A1 | 5/2007 | Hodorek |
| 2007/0129809 A1 | 6/2007 | Meridew et al. |

(56) References Cited

U.S. PATENT DOCUMENTS

| | | |
|---|---|---|
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0167926 A1 | 7/2007 | Blott et al. |
| 2007/0167950 A1 | 7/2007 | Tauro et al. |
| 2007/0173948 A1 | 7/2007 | Meridew et al. |
| 2007/0185488 A1 | 8/2007 | Pohjonen et al. |
| 2007/0185532 A1 | 8/2007 | Stone et al. |
| 2007/0185568 A1 | 8/2007 | Schwartz |
| 2007/0191849 A1 | 8/2007 | ElAttrache et al. |
| 2007/0191853 A1 | 8/2007 | Stone |
| 2007/0198022 A1 | 8/2007 | Lang et al. |
| 2007/0198036 A1 | 8/2007 | Sklar et al. |
| 2007/0219558 A1 | 9/2007 | Deutsch |
| 2007/0225715 A1 | 9/2007 | Deffenbaugh et al. |
| 2007/0225719 A1 | 9/2007 | Stone et al. |
| 2007/0225763 A1 | 9/2007 | Zwolinski et al. |
| 2007/0225805 A1 | 9/2007 | Schmieding |
| 2007/0233241 A1 | 10/2007 | Graf et al. |
| 2007/0239209 A1 | 10/2007 | Fallman |
| 2007/0239275 A1 | 10/2007 | Willobee |
| 2007/0244565 A1 | 10/2007 | Stchur |
| 2007/0250059 A1 | 10/2007 | Weisshaupt et al. |
| 2007/0250163 A1 | 10/2007 | Cassani |
| 2007/0250175 A1 | 10/2007 | Meridew et al. |
| 2007/0255282 A1 | 11/2007 | Simonton et al. |
| 2007/0260251 A1 | 11/2007 | Weier et al. |
| 2007/0260279 A1 | 11/2007 | Hotter et al. |
| 2007/0265704 A1 | 11/2007 | Mayer et al. |
| 2007/0270856 A1 | 11/2007 | Morales et al. |
| 2007/0270878 A1 | 11/2007 | Leisinger |
| 2007/0276387 A1 | 11/2007 | Morales et al. |
| 2007/0288023 A1 | 12/2007 | Pellegrino et al. |
| 2008/0009904 A1 | 1/2008 | Bourque et al. |
| 2008/0027430 A1 | 1/2008 | Montgomery et al. |
| 2008/0027440 A1 | 1/2008 | Marissen et al. |
| 2008/0027446 A1 | 1/2008 | Stone et al. |
| 2008/0033549 A1 | 2/2008 | Marshall et al. |
| 2008/0046009 A1 | 2/2008 | Albertorio et al. |
| 2008/0051836 A1 | 2/2008 | Foerster et al. |
| 2008/0058787 A1 | 3/2008 | Gertner |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0086138 A1 | 4/2008 | Stone et al. |
| 2008/0097430 A1 | 4/2008 | Bernstein et al. |
| 2008/0114460 A1 | 5/2008 | Willobee et al. |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0132948 A1 | 6/2008 | Surti et al. |
| 2008/0133007 A1 | 6/2008 | Donnelly et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0147187 A1 | 6/2008 | Bollinger et al. |
| 2008/0154260 A1 | 6/2008 | Hoof |
| 2008/0154314 A1 | 6/2008 | McDevitt |
| 2008/0161806 A1 | 7/2008 | Donnelly et al. |
| 2008/0161852 A1 | 7/2008 | Kaiser et al. |
| 2008/0161861 A1 | 7/2008 | Huebner |
| 2008/0161864 A1 | 7/2008 | Beck et al. |
| 2008/0166421 A1 | 7/2008 | Buhr et al. |
| 2008/0172097 A1 | 7/2008 | Lerch et al. |
| 2008/0177302 A1 | 7/2008 | Shurnas |
| 2008/0183290 A1 | 7/2008 | Baird et al. |
| 2008/0188933 A1 | 8/2008 | Koob et al. |
| 2008/0188936 A1 | 8/2008 | Ball et al. |
| 2008/0208252 A1 | 8/2008 | Holmes |
| 2008/0217263 A1 | 9/2008 | Higgins et al. |
| 2008/0221527 A1 | 9/2008 | Bradley et al. |
| 2008/0221578 A1 | 9/2008 | Zeitani |
| 2008/0228186 A1 | 9/2008 | Gall et al. |
| 2008/0234730 A1 | 9/2008 | Cotton et al. |
| 2008/0255613 A1 | 10/2008 | Kaiser et al. |
| 2008/0257363 A1 | 10/2008 | Schoenefeld et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275469 A1 | 11/2008 | Fanton et al. |
| 2008/0275477 A1 | 11/2008 | Sterrett et al. |
| 2008/0281428 A1 | 11/2008 | Meyers et al. |
| 2008/0300611 A1 | 12/2008 | Houser et al. |
| 2008/0312689 A1 | 12/2008 | Denham et al. |
| 2008/0319478 A1 | 12/2008 | Foerster et al. |
| 2009/0018589 A1 | 1/2009 | Smisson, III et al. |
| 2009/0018655 A1 | 1/2009 | Brunelle et al. |
| 2009/0043342 A1 | 2/2009 | Freedland |
| 2009/0054928 A1 | 2/2009 | Denham et al. |
| 2009/0062847 A1 | 3/2009 | Ken |
| 2009/0062854 A1 | 3/2009 | Kaiser et al. |
| 2009/0082790 A1 | 3/2009 | Shad et al. |
| 2009/0082805 A1* | 3/2009 | Kaiser et al. ............... 606/228 |
| 2009/0084491 A1 | 4/2009 | Uthgenannt et al. |
| 2009/0099598 A1 | 4/2009 | McDevitt et al. |
| 2009/0105717 A1 | 4/2009 | Bluechel |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0216325 A1 | 8/2009 | May et al. |
| 2009/0228042 A1 | 9/2009 | Koogle,, Jr. et al. |
| 2009/0234357 A1 | 9/2009 | Morales et al. |
| 2009/0234358 A1 | 9/2009 | Morales et al. |
| 2009/0234451 A1 | 9/2009 | Manderson |
| 2009/0240251 A1 | 9/2009 | Gabele |
| 2009/0240335 A1 | 9/2009 | Arcenio et al. |
| 2009/0248091 A1 | 10/2009 | Teague et al. |
| 2009/0265014 A1 | 10/2009 | May et al. |
| 2009/0265015 A1 | 10/2009 | May et al. |
| 2009/0287215 A1 | 11/2009 | Fisher et al. |
| 2009/0299409 A1 | 12/2009 | Coe et al. |
| 2009/0306711 A1 | 12/2009 | Stone et al. |
| 2009/0312776 A1 | 12/2009 | Kaiser et al. |
| 2009/0312793 A1 | 12/2009 | Huxel et al. |
| 2009/0318960 A1 | 12/2009 | Burkhart |
| 2009/0318961 A1 | 12/2009 | Stone et al. |
| 2010/0016899 A1 | 1/2010 | Gelfand |
| 2010/0042114 A1 | 2/2010 | Schaffhausen |
| 2010/0063541 A1 | 3/2010 | Brunelle et al. |
| 2010/0087857 A1 | 4/2010 | Stone et al. |
| 2010/0094355 A1 | 4/2010 | Trenhaile |
| 2010/0106254 A1 | 4/2010 | Delsignore |
| 2010/0121348 A1 | 5/2010 | Van Der Burg et al. |
| 2010/0145384 A1 | 6/2010 | Stone et al. |
| 2010/0152752 A1 | 6/2010 | Denove et al. |
| 2010/0191342 A1 | 7/2010 | Byrd et al. |
| 2010/0204700 A1 | 8/2010 | Falahee |
| 2010/0211071 A1 | 8/2010 | Lettmann et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0274282 A1 | 10/2010 | Olson |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2011/0009885 A1 | 1/2011 | Graf et al. |
| 2011/0022083 A1 | 1/2011 | DiMatteo et al. |
| 2011/0026141 A1 | 2/2011 | Barrows |
| 2011/0046733 A1 | 2/2011 | Eggli |
| 2011/0087225 A1 | 4/2011 | Fritzinger |

(56) References Cited

U.S. PATENT DOCUMENTS

| | | |
|---|---|---|
| 2011/0087284 A1 | 4/2011 | Stone et al. |
| 2011/0098727 A1 | 4/2011 | Kaiser et al. |
| 2011/0106153 A1 | 5/2011 | Stone et al. |
| 2011/0112537 A1 | 5/2011 | Bernstein et al. |
| 2011/0112538 A1 | 5/2011 | Dell'Oca |
| 2011/0160767 A1 | 6/2011 | Stone et al. |
| 2011/0160768 A1 | 6/2011 | Stone et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0218625 A1 | 9/2011 | Berelsman et al. |
| 2011/0224799 A1 | 9/2011 | Stone |
| 2011/0245868 A1 | 10/2011 | Teeslink et al. |
| 2011/0264141 A1 | 10/2011 | Denham et al. |
| 2011/0270278 A1 | 11/2011 | Overes et al. |
| 2011/0270306 A1 | 11/2011 | Denham et al. |
| 2012/0004669 A1 | 1/2012 | Overes et al. |
| 2012/0041485 A1 | 2/2012 | Kaiser et al. |
| 2012/0041486 A1 | 2/2012 | Stone et al. |
| 2012/0041496 A1 | 2/2012 | Walker |
| 2012/0046693 A1 | 2/2012 | Denham et al. |
| 2012/0059417 A1 | 3/2012 | Norton et al. |
| 2012/0059418 A1 | 3/2012 | Denham et al. |
| 2012/0059468 A1 | 3/2012 | Mattern et al. |
| 2012/0089193 A1 | 4/2012 | Stone et al. |
| 2012/0095470 A1 | 4/2012 | Kaiser et al. |
| 2012/0109156 A1 | 5/2012 | Overes et al. |
| 2012/0116409 A1 | 5/2012 | Stone |
| 2012/0116450 A1 | 5/2012 | McDevitt et al. |
| 2012/0116452 A1 | 5/2012 | Stone et al. |
| 2012/0123447 A1 | 5/2012 | Corrao et al. |
| 2012/0123474 A1 | 5/2012 | Zajac et al. |
| 2012/0123541 A1 | 5/2012 | Albertorio et al. |
| 2012/0143215 A1 | 6/2012 | Corrao et al. |
| 2012/0150223 A1 | 6/2012 | Manos et al. |
| 2012/0150297 A1 | 6/2012 | Denham et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0197271 A1 | 8/2012 | Astorino et al. |
| 2012/0215257 A1 | 8/2012 | McDevitt et al. |
| 2012/0245585 A1 | 9/2012 | Kaiser et al. |
| 2012/0265219 A1 | 10/2012 | Rushdy et al. |
| 2012/0290003 A1 | 11/2012 | Dreyfuss |
| 2012/0290004 A1 | 11/2012 | Lombardo et al. |
| 2012/0296427 A1 | 11/2012 | Conner et al. |
| 2012/0310245 A1 | 12/2012 | Hoeppner et al. |
| 2013/0018375 A1 | 1/2013 | Dell'Oca |
| 2013/0018416 A1 | 1/2013 | Lombardo et al. |
| 2013/0023928 A1* | 1/2013 | Dreyfuss ............... 606/228 |
| 2013/0023929 A1 | 1/2013 | Sullivan et al. |
| 2013/0023930 A1 | 1/2013 | Stone et al. |
| 2013/0035698 A1 | 2/2013 | Stone et al. |
| 2013/0035722 A1 | 2/2013 | McDevitt et al. |
| 2013/0046341 A1 | 2/2013 | Stone et al. |
| 2013/0090731 A1 | 4/2013 | Walker |
| 2013/0103082 A1 | 4/2013 | Kaiser et al. |
| 2013/0110165 A1 | 5/2013 | Burkhart et al. |
| 2013/0110251 A1 | 5/2013 | Metzger et al. |
| 2013/0116730 A1 | 5/2013 | Denham et al. |
| 2013/0123810 A1 | 5/2013 | Brown et al. |
| 2013/0123813 A1 | 5/2013 | Stone et al. |
| 2013/0131722 A1 | 5/2013 | Marchand et al. |
| 2013/0138123 A1 | 5/2013 | Stone et al. |
| 2013/0144337 A1 | 6/2013 | Stone et al. |
| 2013/0144338 A1 | 6/2013 | Stone et al. |
| 2013/0158601 A1 | 6/2013 | Stone et al. |
| 2013/0190818 A1 | 7/2013 | Norton |
| 2013/0190819 A1 | 7/2013 | Norton |
| 2013/0204276 A1 | 8/2013 | Stone et al. |
| 2013/0211452 A1 | 8/2013 | Stone et al. |
| 2013/0237997 A1 | 9/2013 | Arai et al. |
| 2013/0245761 A1 | 9/2013 | Conner et al. |
| 2013/0274812 A1 | 10/2013 | Dell'Oca |
| 2013/0289564 A1 | 10/2013 | Bernstein et al. |
| 2013/0317621 A1 | 11/2013 | Metzger et al. |
| 2013/0331848 A1 | 12/2013 | Kaiser et al. |
| 2014/0046367 A1 | 2/2014 | Stone et al. |
| 2014/0046368 A1 | 2/2014 | Kaiser et al. |
| 2014/0067081 A1 | 3/2014 | Stone |
| 2014/0088655 A1 | 3/2014 | Stone et al. |
| 2014/0094913 A1 | 4/2014 | Berelsman et al. |
| 2014/0135835 A1 | 5/2014 | Stone et al. |
| 2014/0163613 A1 | 6/2014 | Stone et al. |
| 2014/0163614 A1 | 6/2014 | Denham et al. |
| 2014/0194927 A1 | 7/2014 | Kaiser et al. |
| 2014/0200583 A1 | 7/2014 | Stone et al. |
| 2014/0257378 A1 | 9/2014 | Norton et al. |
| 2014/0276992 A1 | 9/2014 | Stone et al. |
| 2014/0277447 A1 | 9/2014 | Berelsman et al. |
| 2014/0324101 A1 | 10/2014 | Denham et al. |
| 2014/0330311 A1 | 11/2014 | Denham et al. |
| 2014/0350674 A1 | 11/2014 | Stone et al. |
| 2015/0012094 A1 | 1/2015 | Denham et al. |
| 2015/0057757 A1 | 2/2015 | Metzger et al. |
| 2015/0119890 A1 | 4/2015 | Kaiser et al. |
| 2015/0127051 A1 | 5/2015 | Kaiser et al. |
| 2015/0134000 A1 | 5/2015 | Denham et al. |
| 2015/0173887 A1 | 6/2015 | Berelsman et al. |
| 2015/0257750 A1 | 9/2015 | Kaiser et al. |
| 2016/0000483 A1 | 1/2016 | Stone |
| 2016/0022261 A1 | 1/2016 | Stone et al. |
| 2016/0058436 A1 | 3/2016 | Stone et al. |
| 2016/0081789 A1 | 3/2016 | Denham et al. |
| 2016/0106414 A1 | 4/2016 | Stone et al. |
| 2016/0128684 A1 | 5/2016 | Stone et al. |
| 2016/0183935 A1 | 6/2016 | Stone |
| 2016/0199053 A1 | 7/2016 | Norton et al. |

FOREIGN PATENT DOCUMENTS

| | | |
|---|---|---|
| AU | 4381268 A | 4/1970 |
| AU | 5850469 | 1/1971 |
| AU | 5963869 | 2/1971 |
| AU | 1505470 | 11/1971 |
| AU | 2223767 | 5/1973 |
| AU | 3615171 | 5/1973 |
| AU | 5028569 | 9/1973 |
| AU | 7110887 | 10/1987 |
| AU | 639410 | 11/1989 |
| AU | 639410 A | 11/1989 |
| AU | 651929 | 8/1994 |
| AU | 651929 B2 | 8/1994 |
| CN | 105208970 A | 12/2015 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 | 2/1986 |
| DE | 4127550 | 2/1993 |
| DE | 4302397 | 7/1993 |
| DE | 29621340 | 5/1998 |
| DE | 233303 C | 3/2000 |
| DE | 19841252 | 3/2000 |
| DE | 29922088 U1 | 4/2000 |
| DE | 20207781 U1 | 8/2002 |
| EP | 19062 A1 | 11/1980 |
| EP | 0108912 | 5/1984 |
| EP | 0129422 A2 | 12/1984 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |

(56) References Cited

FOREIGN PATENT DOCUMENTS

| | | |
|---|---|---|
| EP | 0374088 | 6/1990 |
| EP | 0409364 | 1/1991 |
| EP | 0415915 | 3/1991 |
| EP | 0440991 | 8/1991 |
| EP | 440991 A1 | 8/1991 |
| EP | 0441065 | 8/1991 |
| EP | 0447065 A2 | 9/1991 |
| EP | 0451932 | 10/1991 |
| EP | 0464480 | 1/1992 |
| EP | 0490417 A1 | 6/1992 |
| EP | 0497079 | 8/1992 |
| EP | 0502509 | 9/1992 |
| EP | 0502698 | 9/1992 |
| EP | 520177 | 12/1992 |
| EP | 0520177 A1 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 | 5/1994 |
| EP | 0611551 A1 | 8/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| EP | 1741412 A2 | 1/2007 |
| EP | 1864617 A2 | 12/2007 |
| EP | 2238944 A2 | 10/2010 |
| EP | 2544607 A1 | 1/2013 |
| EP | 2709557 A1 | 3/2014 |
| FR | 2622790 | 5/1989 |
| FR | 2655840 | 6/1991 |
| FR | 2663837 A1 | 1/1992 |
| FR | 2682867 | 4/1993 |
| FR | 2687911 | 9/1993 |
| FR | 2688689 | 9/1993 |
| FR | 2704140 | 10/1994 |
| FR | 27177070 | 9/1995 |
| FR | 2723528 | 2/1996 |
| FR | 2734709 A1 | 12/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 A | 9/1992 |
| GB | 2312376 | 10/1997 |
| GB | 2403416 A | 1/2005 |
| JP | 5362911 | 5/1978 |
| JP | 5362911 U | 5/1978 |
| JP | 5362912 | 5/1978 |
| JP | 5362912 U | 5/1978 |
| JP | 5374942 | 6/1978 |
| JP | 5374942 U | 6/1978 |
| JP | 5378230 | 6/1978 |
| JP | 54176284 U | 12/1979 |
| JP | 54178988 U | 12/1979 |
| JP | 62159647 | 7/1987 |
| JP | 62295657 | 12/1987 |
| JP | 5269160 | 10/1993 |
| JP | 5300917 | 11/1993 |
| JP | 751292 | 2/1995 |
| JP | 10127672 A | 5/1998 |
| JP | 10211213 | 8/1998 |
| RU | 2051647 C1 | 1/1996 |
| RU | 2076667 C1 | 4/1997 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9609797 A1 | 4/1996 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9937219 A1 | 7/1999 |
| WO | WO-9944544 | 9/1999 |
| WO | WO-9952472 A1 | 10/1999 |
| WO | WO-0004159 A1 | 1/2000 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-03092551 A1 | 11/2003 |
| WO | WO-2004091412 A1 | 10/2004 |
| WO | WO-2005104992 A1 | 11/2005 |
| WO | WO-2005122954 | 12/2005 |
| WO | WO-2006023661 A2 | 3/2006 |
| WO | WO-2006055823 A2 | 5/2006 |
| WO | WO-2007045460 A2 | 4/2007 |
| WO | WO-2007103562 A2 | 9/2007 |
| WO | WO-2007109280 A2 | 9/2007 |
| WO | WO-2007119057 A1 | 10/2007 |
| WO | WO-2008002550 A2 | 1/2008 |
| WO | WO-2008015171 A1 | 2/2008 |
| WO | WO-2008073588 A2 | 6/2008 |
| WO | WO-2009012021 A1 | 1/2009 |
| WO | WO-2009083047 A1 | 7/2009 |
| WO | WO-2009131820 A1 | 10/2009 |
| WO | WO-2010138832 A1 | 12/2010 |
| WO | WO-2011112371 A1 | 9/2011 |
| WO | WO-2011150238 A1 | 12/2011 |
| WO | WO-2012134999 A1 | 10/2012 |
| WO | WO-2012158583 A1 | 11/2012 |
| WO | WO-2013066974 A1 | 5/2013 |
| WO | WO-2013074525 A1 | 5/2013 |
| WO | WO-2014/100109 A1 | 6/2014 |
| WO | WO-2014151766 A1 | 9/2014 |

OTHER PUBLICATIONS

Invitation to Pay Additional Fees mailed Jul. 19, 2012, for PCT/US2012/037703 claiming benefit of U.S. Appl. No. 13/109,667, filed May 7, 2011.
"AperFix® System Surgical Technique Guide. Single Tunnel Double Bundle.™" Cayenne Medical brochure. (Aug. 2008) 8 sheets.
"Bio-Intrafix (TCP/PLA & Intrafix, Tibial Soft Tissue Fasteners," by DePuy Mitek, 6 sheets, (date unknown).
"Bio-Intrafix Tibial Soft Tissue Fasteners, Building on the Legacy of IntraFix," brochure. DePuy Mitek,(Feb. 2007) 6 sheets.

(56) References Cited

OTHER PUBLICATIONS

"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"Do your next distal tendon repair with . . . The Lubbers Technique", Teno Fix® brochure, 2003 (2 pages) Ortheon® Medical.
"EZ Loc Femoral Fixation Device," copyright 2005 Arthrotek, Inc. (8 sheets).
"JuggerKnot™ Soft Anchor Midfoot Repair," brochure. Biomet Sports Medicine (Jul. 2011) 12 sheets.
"JuggerKnot™ Soft Anchor. It's Small. It's strong. And it's all suture . . . " Ordering Information brochure. Biomet Sports Medicine (Jun. 2011) 2 sheets.
"JuggerKnot™ Soft Anchor. Labral Repair," brochure. Biomet Sports Medicine (Apr. 2011) 12 sheets.
"Make your next tendon repair an open-and-shut case. The Teno Fix® Tendon Repair System", Teno Fix® brochure, 2003 (2 pages) Ortheon® Medical.
"PANALOK Anchor with PDS II and ETHIBOND Suture", Mitek Products ETHICON, 1997.
"SE Graft Tensioning System Surgical Technique," Linvatec Corporation copyright 2003, 2004.
"Technique for ACL Reconstruction with Acufex Director Drill Guide and Endobutton CL," by Thomas D. Roseberg, copyright 1999 Smith & Nephew.
A. Weiler, et al; Biodegradierbare Interferenzschrauben in der Kreuzbandchirurgie; OP-JOURNAL 14 pp. 278-284; 1998.
Arthrotek, A Biomet Company; Knees; Sure fire Hybrid Meniscal Device. (2005).
Arthrotek, A Biomet Company; Sure fire Hybrid Meniscal Device; Launch Date: Fall AANA 2004.
F. Alan Barber, M.D., "Uses and Abuses of Sutures and Anchors," Shoulder Scope, San Diego Shoulder Arthroscopy Library.
F. Alan Barber, M.D., "Using Sutures and Anchors," San Diego Shoulder Arthroscopy Course, 17th Annual Meeting.
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Roy Alan Majors, M.D.; "Meniscal repairs: proven techniques and current trends," Lippincott Williams & Wilkins, Inc.; 2002.
Shoulder Arthroscopy; pp. H-2-H-22.
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
International Preliminary Report on Patentability mailed Dec. 6, 2012 for PCT/US2011/038188 claiming benefit of U.S. Appl. No. 12/788,966, filed May 27, 2010.
International Preliminary Report on Patentability mailed Sep. 20, 2012 for PCT/US2011/026349 which claims benefit of U.S. Appl. No. 12/719,337, filed Mar. 8, 2010.
Interview Summary mailed Jun. 20, 2011 for U.S. Appl. No. 12/196,405.
Notice of Allowance (Supplemental Notice of Allowability) mailed Apr. 15, 2011 for U.S. Appl. No. 12/196,398, filed Aug. 22, 2008; now U.S. Pat. No. 7,959,650.
Notice of Allowance (Supplemental Notice of Allowability) mailed Mar. 9, 2011 for U.S. Appl. No. 12/196,398, filed Aug. 22, 2008; now U.S. Pat. No. 7,959,650.
Notice of Allowance with Interview Summary mailed Aug. 31, 2011 for U.S. Appl. No. 12/474,802, filed Nov. 3, 2010.
Notice of Allowance with Interview Summary mailed Feb. 3, 2011 for U.S. Appl. No. 12/196,398, filed Aug. 22, 2010; now U.S. Pat. No. 7,959,650.
Office Action from the U.S. Patent Office mailed Mar. 5, 2013 for U.S. Appl. No. 12/702,067.
Office Action from the U.S. Patent Office mailed Mar. 13, 2013 for U.S. Appl. No. 13/181,729.
Office Action from the U.S. Patent Office mailed Mar. 20, 2013 for U.S. Appl. No. 13/399,125.
Office Action from the U.S. Patent Office mailed May 22, 2013 for U.S. Appl. No. 13/098,927.
Office Action mailed Apr. 11, 2011 for U.S. Appl. No. 12/196,405.
Office Action mailed May 19, 2009 for U.S. Appl. No. 11/541,505, filed Sep. 29, 2006; now U.S. Pat. No. 7,658,751.
Office Action mailed May 4, 2011 for U.S. Appl. No. 12/196,407, filed Aug. 22, 2008.
Office Action mailed May 9, 2011 for U.S. Appl. No. 12/196,410, filed Aug. 22, 2008.
Restriction Requirement mailed Mar. 22, 2011 for U.S. Appl. No. 12/196,407, filed Aug. 22, 2008.
Restriction Requirement mailed Mar. 9, 2009 for U.S. Appl. No. 11/541,505, filed Sep. 29, 2006; now U.S. Pat. No. 7,658,751.
Restriction Requirement mailed Mar. 9, 2009 for U.S. Appl. No. 11/541,506, filed Sep. 29, 2006; now U.S. Pat. No. 7,601,165.
Restriction Requirement mailed Sep. 29, 2010 for U.S. Appl. No. 12/196,398, filed Aug. 22, 2008; now U.S. Pat. No. 7,959,650.
"ToggleLoc™ Fixation Device with ZipLoop™ Technology: ACL Reconstruction Bone-Tendon-Bone," by James R. Andrews, M.D., of Biomet Sports Medicine, a Biomet Company Brochure (2013), pp. 1-20.
International Preliminary Report on Patentability and Written Opinion mailed May 30, 2014 for PCT/US2012/064832 which claims benefit of U.S. Appl. No. 13/295,126, filed Nov. 14, 2011.
International Search Report and Written Opinion mailed Jun. 6, 2014 for PCT/US2014/026413 which claims benefit of U.S. Appl. No. 14/095,614, filed Dec. 3, 2013 and U.S. Appl. No. 14/095,639, filed Dec. 3, 2013.
ToggleLoc Fixation Device with ZipLoop Technology: Biceps Tendon Reattachment by Mark J. Albritton, M.D. and Daniel Worrel, M.D. of Biomet Sports Medicine, a Biomet Company Brochure (2099, 2011), pp. 1-12.
International Search Report and Written Opinion mailed Feb. 6, 2013 for PCT/US2012/064832 which claims benefit of U.S. Appl. No. 13/295,126, filed Nov. 14, 2011.
International Search Report and Written Opinion mailed Mar. 6, 2013 for PCT/US2012/062738 which claims benefit of U.S. Appl. No. 13/288,459, filed Nov. 3, 2011.
Office Action from the U.S. Patent Office mailed Jul. 15, 2013 for U.S. Appl. No. 13/587,374.
Office Action from the U.S. Patent Office mailed Aug. 7, 2013 for U.S. Appl. No. 13/412,127.

(56) References Cited

OTHER PUBLICATIONS

Office Action from the U.S. Patent Office mailed Sep. 11, 2013 for U.S. Appl. No. 13/412,116.
International Search Report and Written Opinion mailed Mar. 6, 2014 for PCT/US2013/075989 which claims benefit of U.S. Appl. No. 13/720,648, filed Dec. 19, 2012.
"Arthroscopic Meniscal Repair using the Meniscal Cinch™", Surgical Technique brochure. (2008) Arthrex® 6 sheets.
Interview Summary mailed Jul. 14, 2011 for U.S. Appl. No. 12/196,407.
Interview Summary mailed Jul. 14, 2011 for U.S. Appl. No. 12/196,410.
Notice of Allowance mailed Oct. 13, 2011 for U.S. Appl. No. 12/196,410.
Notice of Allowance mailed Oct. 26, 2011 for U.S. Appl. No. 12/196,405.
Notice of Allowance mailed Oct. 26, 2011 for U.S. Appl. No. 12/196,407.
Notice of Allowance mailed Mar. 22, 2012 for U.S. Appl. No. 13/102,182.
Notice of Allowance mailed Jun. 1, 2009 for U.S. Appl. No. 11/541,506.
Notice of Allowance mailed Sep. 18, 2009 for U.S. Appl. No. 11/541,505.
Office Action mailed Dec. 7, 2011 for U.S. Appl. No. 12/589,168.
Pioneer® Sternal Cable System (2010).
Rapid Sternal Closure (2006) KLS Martin L.P. http://www.rapidsternalclosure.com/medical/demo.php Web accessed Sep. 8, 2008.
Saxena, Pankaj, MCh, DNB et al., "Use of Double Wires in Sternal Closure, A Useful Technique," Texas Heart® Institute. Journal List>Tex Heart Inst J > v.33(4); (2006).
Zeitani, Jacob, M.D., "A New Sternal Reinforcement Device to Prevent and Treat Sternal Dehiscence," CTSNet.org (Jun. 30, 2008).
"Suture Tensioner w/Tensiometer," Arthrex® , Inc. catalog "Next Generation in Knee Ligament Reconstruction & Repair Technology," 2009.
"TriTis™ Tibial Fixation System and Implant" brochure. Scandius Biomedical (2006).
International Search Report and Written Opinion mailed Sep. 21, 2012 for PCT/US2012/037703 filed May 14, 2012 claiming benefit of U.S. Appl. No. 13/109,667, filed May 17, 2011 and U.S. Appl. No. 13/109,672, filed May 17, 2011.
Interview Summary mailed Nov. 27, 2012 for U.S. Appl. No. 13/098,897.
Office Action mailed Oct. 24, 2012 for U.S. Appl. No. 13/399,125.
Office Action mailed Sep. 21, 2012 for U.S. Appl. No. 13/098,897.
Office Action mailed Sep. 24, 2012 for U.S. Appl. No. 13/098,927.
Office Action mailed Oct. 2, 2012 for U.S. Appl. No. 13/181,729.
International Preliminary Report on Patentability and Written Opinion mailed Nov. 28, 2013 for PCT/US2012/037703, which claims benefit of U.S. Appl. No. 13/109,672, filed May 17, 2011,and U.S. Appl. No. 13/109,667, filed May 17, 2011.
Notice of Allowance mailed Oct. 7, 2013 for U.S. Appl. No. 12/702,067.
Notice of Allowance mailed Oct. 24, 2013 for U.S. Appl. No. 13/412,127.
Office Action mailed Dec. 13, 2013 for U.S. Appl. No. 13/412,105.
Ziptight™ Fixation System Featuring Zip Loop™ Technology. Ankle Syndesmosis. Surgical Protocol by Timothy Charlton, M.D. Biomet Sports® Medicine brochure. (Jun. 15, 2011) 8 pages.
"JuggerKnot™ Soft Anchor: Arthroscopic and Mini-Open Rotator Cuff Repair Using JuggerKnot™ Soft Anchor—2.9mm with ALLthread™ Knotless Anchor Surgical Technique" brochure, Biomet® Sports Medicine. (2013) 16 pages.
U.S. Appl. No. 10/984,624, Final Office Action mailed Jan. 5, 2009, 9 pgs.
U.S. Appl. No. 10/984,624, Non Final Office Action mailed Jul. 10, 2008, 9 pgs.
U.S. Appl. No. 10/984,624, Notice of Allowance mailed Jun. 12, 2009, 9 pgs.
U.S. Appl. No. 10/984,624, Response filed Apr. 1, 2009 to Final Office Action mailed Jan. 5, 2009, 16 pgs.
U.S. Appl. No. 10/984,624, Response filed Apr. 15, 2008 to Restriction Requirement mailed Mar. 24, 2008, 1 pg.
U.S. Appl. No. 10/984,624, Response filed Oct. 10, 2008 to Non Final Office Action mailed Jul. 10, 2008, 12 pgs.
U.S. Appl. No. 10/984,624, Restriction Requirement mailed Mar. 24, 2008, 5 pgs.
U.S. Appl. No. 11/294,694, Final Office Action mailed Sep. 1, 2010, 14 pgs.
U.S. Appl. No. 11/294,694, Non Final Office Action mailed Mar. 16, 2010, 19 pgs.
U.S. Appl. No. 11/294,694, Notice of Allowance mailed Nov. 17, 2010, 4 pgs.
U.S. Appl. No. 11/294,694, Preliminary Amendment filed Jan. 13, 2010, 9 pgs.
U.S. Appl. No. 11/294,694, Response filed Jun. 16, 2010 to Non Final Office Action mailed Mar. 16, 2010, 16 pgs.
U.S. Appl. No. 11/294,694, Response filed Nov. 1, 2010 to Final Office Action mailed Sep. 1, 2010, 10 pgs.
U.S. Appl. No. 11/294,694, Response filed Dec. 22, 2009 to Restriction Requirement mailed Nov. 25, 2009, 1 pg.
U.S. Appl. No. 11/294,694, Restriction Requirement mailed Nov. 25, 2009, 9 pgs.
U.S. Appl. No. 11/347,661, Examiner Interview Summary mailed Sep. 11, 2009, 2 pgs.
U.S. Appl. No. 11/347,661, Final Office Action mailed Mar. 3, 2009, 15 pgs.
U.S. Appl. No. 11/347,661, Non Final Office Action mailed Aug. 13, 2009, 19 pgs.
U.S. Appl. No. 11/347,661, Non Final Office Action mailed Aug. 21, 2008, 11 pgs.
U.S. Appl. No. 11/347,661, Notice of Allowance mailed Feb. 24, 2010, 8 pgs.
U.S. Appl. No. 11/347,661, Notice of Allowance mailed May 5, 2010, 8 pgs.
U.S. Appl. No. 11/347,661, Response filed May 29, 2008 to Restriction Requirement mailed Apr. 30, 2008, 1 pg.
U.S. Appl. No. 11/347,661, Response filed Jun. 3, 2009 to Final Office Action mailed Mar. 3, 2009, 19 pgs.
U.S. Appl. No. 11/347,661, Response filed Nov. 6, 2009 to Non Final Office Action mailed Aug. 13, 2009, 16 pgs.
U.S. Appl. No. 11/347,661, Response filed Nov. 19, 2008 to Non Final Office Action mailed Aug. 21, 2008, 12 pgs.
U.S. Appl. No. 11/347,661, Restriction Requirement mailed Apr. 30, 2008, 6 pgs.
U.S. Appl. No. 11/347,662, Examiner Interview Summary mailed Jun. 24, 2010, 3 pgs.
U.S. Appl. No. 11/347,662, Examiner Interview Summary mailed Nov. 9, 2009, 3 pgs.
U.S. Appl. No. 11/347,662, Final Office Action mailed Sep. 16, 2009, 13 pgs.
U.S. Appl. No. 11/347,662, Final Office Action mailed Oct. 26, 2010, 10 pgs.
U.S. Appl. No. 11/347,662, Non Final Office Action mailed Mar. 9, 2009, 11 pgs.
U.S. Appl. No. 11/347,662, Non Final Office Action mailed May 21, 2010, 19 pgs.
U.S. Appl. No. 11/347,662, Non Final Office Action mailed Oct. 28, 2008, 13 pgs.
U.S. Appl. No. 11/347,662, Response filed Jan. 16, 2009 to Non Final Office Action mailed Oct. 28, 2008, 16 pgs.
U.S. Appl. No. 11/347,662, Response filed Feb. 12, 2010 to Final Office Action mailed Sep. 16 2009, 21 pgs.
U.S. Appl. No. 11/347,662, Response filed Jun. 5, 2009 to Non Final Office Action mailed Mar. 9, 2009, 13 pgs.
U.S. Appl. No. 11/347,662, Response filed Aug. 20, 2010 to Non Final Office Action mailed May 21, 2010, 13 pgs.
U.S. Appl. No. 11/386,071, Advisory Action mailed Dec. 23, 2010, 3 pgs.

(56) References Cited

OTHER PUBLICATIONS

U.S. Appl. No. 11/386,071, Examiner Interview Summary mailed Jan. 31, 2011, 3 pgs.
U.S. Appl. No. 11/386,071, Examiner Interview Summary mailed Jul. 21, 2010, 3 pgs.
U.S. Appl. No. 11/386,071, Final Office Action mailed Oct. 27, 2010, 10 pgs.
U.S. Appl. No. 11/386,071, Non Final Office Action mailed May 12, 2010, 13 pgs.
U.S. Appl. No. 11/386,071, Notice of Allowance mailed Jun. 6, 2011, 6 pgs.
U.S. Appl. No. 11/386,071, Response filed Jan. 26, 2011 to Advisory Action mailed Dec. 23, 2010, 13 pgs.
U.S. Appl. No. 11/386,071, Response filed Aug. 12, 2010 to Non Final Office Action mailed May 12, 2010, 14 pgs.
U.S. Appl. No. 11/386,071, Response filed Dec. 15, 2010 to Final Office Action mailed Oct. 27, 2010, 14 pgs.
U.S. Appl. No. 11/408,282, Final Office Action mailed Dec. 15, 2008, 8 pgs.
U.S. Appl. No. 11/408,282, Non Final Office Action mailed May 23, 2008, 12 pgs.
U.S. Appl. No. 11/408,282, Response filed Aug. 21, 2008 to Non Final Office Action mailed May 23, 2008, 10 pgs.
U.S. Appl. No. 11/504,882, Examiner Interview Summary mailed Sep. 2, 2010, 3 pgs.
U.S. Appl. No. 11/504,882, Final Office Action mailed Dec. 21, 2010, 7 pgs.
U.S. Appl. No. 11/504,882, Non Final Office Action mailed Jun. 19, 2014, 11 pgs.
U.S. Appl. No. 11/504,882, Non Final Office Action mailed Jun. 23, 2010, 8 pgs.
U.S. Appl. No. 11/504,882, Non Final Office Action mailed Nov. 13, 2013, 13 pgs.
U.S. Appl. No. 11/504,882, Notice of Allowance mailed Dec. 1, 2014, 9 pgs.
U.S. Appl. No. 11/504,882, Response filed Feb. 10, 2014 to Non Final Office Action mailed Nov. 13, 2013, 11 pgs.
U.S. Appl. No. 11/504,882, Response filed Mar. 18, 2011 to Final Office Action mailed Dec. 21, 2010, 11 pgs.
U.S. Appl. No. 11/504,882, Response filed Sep. 17, 2014 to Non Final Office Action mailed Jun. 19, 2014, 14 pgs.
U.S. Appl. No. 11/504,882, Response filed Sep. 23, 2010 to Non Final Office Action mailed Jun. 23, 2010, 12 pgs.
U.S. Appl. No. 11/504,882, Supplemental Notice of Allowability mailed Mar. 12, 2015, 5 pgs.
U.S. Appl. No. 11/541,505, Response filed Apr. 9, 2009 to Restriction Requirement mailed Mar. 9, 2009, 1 pg.
U.S. Appl. No. 11/541,505, Response filed Jun. 18, 2009 to Non Final Office Action mailed May 19, 2009, 5 pgs.
U.S. Appl. No. 11/541,506, Notice of Allowance mailed Jun. 29, 2009, 8 pgs.
U.S. Appl. No. 11/541,506, Response filed Apr. 9, 2009 to Restriction Requirement mailed Mar. 9, 2009, 1 pg.
U.S. Appl. No. 11/739,768, Examiner Interview Summary mailed May 11, 2011, 3 pgs.
U.S. Appl. No. 11/739,768, Examiner Interview Summary mailed Oct. 4, 2011, 3 pgs.
U.S. Appl. No. 11/739,768, Final Office Action mailed Aug. 22, 2011, 14 pgs.
U.S. Appl. No. 11/739,768, Non Final Office Action mailed Mar. 4, 2011, 11 pgs.
U.S. Appl. No. 11/739,768, Notice of Allowance mailed Nov. 15, 2011, 5 pgs.
U.S. Appl. No. 11/739,768, Response filed Jun. 6, 2011 to Non Final Office Action mailed Mar. 4, 2011, 15 pgs.
U.S. Appl. No. 11/739,768, Response filed Oct. 26, 2011 to Final Office Action mailed Aug. 22, 2011, 14 pgs.
U.S. Appl. No. 11/740,035, Final Office Action mailed Aug. 7, 2008, 9 pgs.
U.S. Appl. No. 11/740,035, Non Final Office Action mailed Jan. 3, 2008, 9 pgs.
U.S. Appl. No. 11/740,035, Response filed Apr. 3, 2008 to Non Final Office Action mailed Jan. 3, 2008, 6 pgs.
U.S. Appl. No. 11/784,821, Corrected Notice of Allowance mailed Dec. 24, 2014, 4 pgs.
U.S. Appl. No. 11/784,821, Examiner Interview Summary mailed Jun. 26, 2014, 3 pgs.
U.S. Appl. No. 11/784,821, Examiner Interview Summary mailed Nov. 17, 2009, 3 pgs.
U.S. Appl. No. 11/784,821, Final Office Action mailed Mar. 10, 2010, 11 pgs.
U.S. Appl. No. 11/784,821, Non Final Office Action mailed Mar. 28, 2014, 14 pgs.
U.S. Appl. No. 11/784,821, Non Final Office Action mailed Sep. 4, 2009, 12 pgs.
U.S. Appl. No. 11/784,821, Notice of Allowance mailed Oct. 21, 2014, 10 pgs.
U.S. Appl. No. 11/784,821, Response filed Jun. 10, 2010 to Final Office Action mailed Mar. 10, 2010, 20 pgs.
U.S. Appl. No. 11/784,821, Response filed Jun. 15, 2009 to Restriction Requirement mailed May 13, 2009, 2 pgs.
U.S. Appl. No. 11/784,821, Response filed Jun. 26, 2014 to Non Final Office Action mailed Mar. 28, 2014, 16 pgs.
U.S. Appl. No. 11/784,821, Response filed Nov. 23, 2009 to Non Final Office Action mailed Sep. 4, 2009, 17 pgs.
U.S. Appl. No. 11/784,821, Restriction Requirement mailed May 13, 2009, 6 pgs.
U.S. Appl. No. 11/869,440, Examiner Interview Summary mailed Mar. 25, 2010, 3 pgs.
U.S. Appl. No. 11/869,440, Non Final Office Action mailed Mar. 1, 2010, 13 pgs.
U.S. Appl. No. 11/869,440, Notice of Allowance mailed Aug. 19, 2010, 10 pgs.
U.S. Appl. No. 11/869,440, Response filed Jun. 1, 2010 to Non Final Office Action mailed Mar. 1, 2010, 14 pgs.
U.S. Appl. No. 11/935,681, Examiner Interview Summary mailed Jul. 19, 2010, 3 pgs.
U.S. Appl. No. 11/935,681, Non Final Office Action mailed May 24, 2010, 12 pgs.
U.S. Appl. No. 11/935,681, Notice of Allowance mailed Nov. 8, 2010, 10 pgs.
U.S. Appl. No. 11/935,681, Response filed Apr. 19, 2010 to Restriction Requirement mailed Mar. 17, 2010, 4 pgs.
U.S. Appl. No. 11/935,681, Response filed Aug. 24, 2010 to Non Final Office Action mailed May 24, 2010, 13 pgs.
U.S. Appl. No. 11/935,681, Restriction Requirement mailed Mar. 17, 2010, 6 pgs.
U.S. Appl. No. 12/014,340, Examiner Interview Summary mailed Jun. 22, 2010, 3 pgs.
U.S. Appl. No. 12/014,340, Non Final Office Action mailed May 25, 2010, 12 pgs.
U.S. Appl. No. 12/014,340, Notice of Allowance mailed Nov. 8, 2010, 9 pgs.
U.S. Appl. No. 12/014,340, Preliminary Amendment filed May 21, 2010, 11 pgs.
U.S. Appl. No. 12/014,340, Response filed Apr. 26, 2010 to Restriction Requirement mailed Mar. 25, 2010, 2 pgs.
U.S. Appl. No. 12/014,340, Response filed Aug. 25, 2010 to Non Final Office Action mailed May 25, 2010, 16 pgs.
U.S. Appl. No. 12/014,340, Restriction Requirement mailed Mar. 25, 2010, 9 pgs.
U.S. Appl. No. 12/014,399, Examiner Interview Summary mailed Jun. 23, 2010, 3 pgs.
U.S. Appl. No. 12/014,399, Non Final Office Action mailed May 26, 2010, 13 pgs.
U.S. Appl. No. 12/014,399, Notice of Allowance mailed Nov. 12, 2010, 11 pgs.
U.S. Appl. No. 12/014,399, Preliminary Amendment filed May 25, 2010, 10 pgs.
U.S. Appl. No. 12/014,399, Response filed May 5, 2010 to Restriction Requirement mailed Apr. 6, 2010, 2 pgs.

(56) References Cited

OTHER PUBLICATIONS

U.S. Appl. No. 12/014,399, Response filed Aug. 25, 2010 to Non Final Office Action mailed May 26, 2010, 14 pgs.
U.S. Appl. No. 12/014,399, Restriction Requirement mailed Apr. 6, 2010, 9 pgs.
U.S. Appl. No. 12/029,861, Examiner Interview Summary mailed Jan. 27, 2012, 3 pgs.
U.S. Appl. No. 12/029,861, Final Office Action mailed Dec. 8, 2011, 11 pgs.
U.S. Appl. No. 12/029,861, Non Final Office Action mailed Jul. 26, 2011, 11 pgs.
U.S. Appl. No. 12/029,861, Notice of Allowance mailed Apr. 26, 2012, 5 pgs.
U.S. Appl. No. 12/029,861, Response filed Jan. 26, 2012 to Final Office Action mailed Dec. 8, 2011, 15 pgs.
U.S. Appl. No. 12/029,861, Response filed May 6, 2011 to Restriction Requirement mailed Apr. 7, 2011, 10 pgs.
U.S. Appl. No. 12/029,861, Response filed Jun. 23, 2011 to Restriction Requirement mailed May 24, 2011, 1 pgs.
U.S. Appl. No. 12/029,861, Response filed Oct. 14, 2011 to Non Final Office Action mailed Jul. 26, 2011, 11 pgs.
U.S. Appl. No. 12/029,861, Restriction Requirement mailed Apr. 7, 2011, 8 pgs.
U.S. Appl. No. 12/029,861, Restriction Requirement mailed May 24, 2011, 6 pgs.
U.S. Appl. No. 12/107,437, Examiner Interview Summary mailed May 10, 2010, 4 pgs.
U.S. Appl. No. 12/107,437, Non Final Office Action mailed Mar. 17, 2010, 9 pgs.
U.S. Appl. No. 12/107,437, Preliminary Amendment filed Feb. 23, 2010, 9 pgs.
U.S. Appl. No. 12/107,437, Response filed Jan. 29, 2010 to Restriction Requirement mailed Jan. 13, 2010, 1 pgs.
U.S. Appl. No. 12/107,437, Restriction Requirement mailed Jan. 13, 2010, 7 pgs.
U.S. Appl. No. 12/196,398, Examiner Interview Summary mailed Nov. 8, 2010, 3 pgs.
U.S. Appl. No. 12/196,398, Preliminary Amendment filed Nov. 10, 2008, 3 pgs.
U.S. Appl. No. 12/196,398, Preliminary Amendment filed Dec. 1, 2010, 12 pgs.
U.S. Appl. No. 12/196,398, Preliminary Amendment filed Dec. 9, 2008, 46 pgs.
U.S. Appl. No. 12/196,398, Response filed Oct. 29, 2010 to Restriction Requirement mailed Aug. 29, 2010, 2 pgs.
U.S. Appl. No. 12/196,405, Preliminary Amendment filed Nov. 10, 2008, 3 pgs.
U.S. Appl. No. 12/196,405, Response filed Mar. 16, 2011 to Restriction Requirement mailed Feb. 14, 2011, 1 pgs.
U.S. Appl. No. 12/196,405, Response filed Jul. 12, 2011 to Non Final Office Action mailed Apr. 11, 2011, 19 pgs.
U.S. Appl. No. 12/196,405, Restriction Requirement mailed Feb. 14, 2011, 6 pgs.
U.S. Appl. No. 12/196,405, Supplemental Amendment filed Oct. 3, 2011, 12 pgs.
U.S. Appl. No. 12/196,407, Preliminary Amendment filed Nov. 10, 2008, 3 pgs.
U.S. Appl. No. 12/196,407, Response filed Apr. 20, 2011 to Restriction Requirement mailed Mar. 22, 2011, 12 pgs.
U.S. Appl. No. 12/196,407, Response filed Aug. 2, 2011 to Non Final Office Action mailed May 4, 2011, 27 pgs.
U.S. Appl. No. 12/196,407, Supplemental Response to Non Final Office Action filed Oct. 3, 2011, 18 pgs.
U.S. Appl. No. 12/196,410, Response filed Apr. 20, 2011 to Restriction Requirement mailed Mar. 22, 2011, 13 pgs.
U.S. Appl. No. 12/196,410, Response filed Aug. 1, 2011 to Non Final Office Action mailed May 9, 2011, 23 pgs.
U.S. Appl. No. 12/196,410, Restriction Requirement mailed Mar. 22, 2011, 6 pgs.
U.S. Appl. No. 12/196,410, Supplemental Amendment filed Oct. 3, 2011, 15 pgs.
U.S. Appl. No. 12/398,548, Examiner Interview Summary mailed Jul. 12, 2011, 3 pgs.
U.S. Appl. No. 12/398,548, Non Final Office Action mailed Apr. 12, 2011, 7 pgs.
U.S. Appl. No. 12/398,548, Notice of Allowance mailed Oct. 18, 2011, 7 pgs.
U.S. Appl. No. 12/398,548, Response filed Jul. 12, 2011 to Non Final Office Action mailed Apr. 12, 2011, 15 pgs.
U.S. Appl. No. 12/398,548, Supplemental Preliminary Amendment filed Sep. 7, 2010, 11 pgs.
U.S. Appl. No. 12/419,491, Examiner Interview Summary mailed May 30, 2012, 3 pgs.
U.S. Appl. No. 12/419,491, Examiner Interview Summary mailed Nov. 29, 2011, 3 pgs.
U.S. Appl. No. 12/419,491, Final Office Action mailed Apr. 12, 2012, 12 pgs.
U.S. Appl. No. 12/419,491, Non Final Office Action mailed Sep. 22, 2011, 12 pgs.
U.S. Appl. No. 12/419,491, Notice of Allowance mailed Jul. 13, 2012, 10 pgs.
U.S. Appl. No. 12/419,491, Response filed May 30, 2012 to Final Office Action mailed Apr. 12, 2012, 12 pgs.
U.S. Appl. No. 12/419,491, Response filed Dec. 9, 2011 to Non Final Office Action mailed Sep. 22, 2011, 17 pgs.
U.S. Appl. No. 12/474,802, Notice of Allowance mailed Oct. 26, 2011, 4 pgs.
U.S. Appl. No. 12/474,802, Response filed Mar. 28, 2011 to Restriction Requirement mailed Feb. 24, 2011, 12 pgs.
U.S. Appl. No. 12/474,802, Restriction Requirement mailed Feb. 24, 2011, 6 pgs.
U.S. Appl. No. 12/489,168, Examiner Interview Summary mailed Feb. 21, 2012, 3 pgs.
U.S. Appl. No. 12/489,168, Notice of Allowance mailed Apr. 26, 2012, 8 pgs.
U.S. Appl. No. 12/489,168, Notice of Allowance mailed Sep. 5, 2012, 8 pgs.
U.S. Appl. No. 12/489,168, Preliminary Amendment filed Oct. 22, 2009, 3 pgs.
U.S. Appl. No. 12/489,168, Response filed Feb. 27, 2012 to Non Final Office Action mailed Dec. 7, 2011, 15 pgs.
U.S. Appl. No. 12/489,168, Response filed Nov. 11, 2011 to Restriction Requirement mailed Oct. 20, 2011, 1 pg.
U.S. Appl. No. 12/489,168, Restriction Require ent mailed Oct. 20, 2011, 8 pgs.
U.S. Appl. No. 12/489,181, Examiner Interview Summary mailed Feb. 13, 2012, 3 pgs.
U.S. Appl. No. 12/489,181, Non Final Office Action mailed Jan. 3, 2012, 9 pgs.
U.S. Appl. No. 12/489,181, Notice of Allowance mailed May 23, 2012, 9 pgs.
U.S. Appl. No. 12/489,181, Preliminary Amendment filed Mar. 31, 2011, 10 pgs.
U.S. Appl. No. 12/489,181, Preliminary Amendment filed Oct. 22, 2009, 3 pgs.
U.S. Appl. No. 12/489,181, Response filed Mar. 27, 2012 to Non Final Office Action mailed Jan. 3, 2012, 12 pgs.
U.S. Appl. No. 12/489,181, Response filed Dec. 5, 2011 to Restriction Requirement mailed Nov. 4, 2011, 1 pg.
U.S. Appl. No. 12/489,181, Restriction Requirement mailed Nov. 4, 2011, 7 pgs.
U.S. Appl. No. 12/570,854, Examiner Interview Summary mailed Apr. 16, 2012, 3 pgs.
U.S. Appl. No. 12/570,854, Non Final Office Action mailed Feb. 10, 2012, 8 pgs.
U.S. Appl. No. 12/570,854, Notice of Allowance mailed Jun. 29, 2012, 10 pgs.
U.S. Appl. No. 12/570,854, Notice of Allowance mailed Sep. 19, 2012, 6 pgs.
U.S. Appl. No. 12/570,854, Response filed May 10, 2012 to Non Final Office Action mailed Feb. 10, 2012, 27 pgs.

(56) References Cited

OTHER PUBLICATIONS

U.S. Appl. No. 12/570,854, Response filed Dec. 20, 2011 to Restriction Requirement mailed Dec. 14, 2011, 1 pg.
U.S. Appl. No. 12/570,854, Restriction Requirement mailed Dec. 14, 2011, 6 pgs.
U.S. Appl. No. 12/702,067, Preliminary Amendment filed Jan. 11, 2011, 13 pgs.
U.S. Appl. No. 12/702,067, Response filed Jun. 5, 2013 to Non Final Office Action, mailed Mar. 5, 2013, 17 pgs.
U.S. Appl. No. 12/702,067, Response filed Oct. 2, 2012 to Restriction Requirement mailed Sep. 4, 2012, 1 pg.
U.S. Appl. No. 12/702,067, Restriction Requirement mailed Sep. 4, 2012, 9 pgs.
U.S. Appl. No. 12/719,337, Advisory Action mailed Sep. 30, 2014, 4 pgs.
U.S. Appl. No. 12/719,337, Examiner Interview Summary mailed Apr. 4, 2014, 4 pgs.
U.S. Appl. No. 12/719,337, Examiner Interview Summary mailed May 14, 2013, 3 pgs.
U.S. Appl. No. 12/719,337, Examiner Interview Summary mailed Sep. 18, 2014, 3 pgs.
U.S. Appl. No. 12/719,337, Final Office Action mailed Mar. 12, 2013, 8 pgs.
U.S. Appl. No. 12/719,337, Final Office Action mailed Jul. 18, 2014, 15 pgs.
U.S. Appl. No. 12/719,337, Non Final Office Action mailed Jan. 10, 2014, 14 pgs.
U.S. Appl. No. 12/719,337, Non Final Office Action mailed Sep. 5, 2012, 7 pgs.
U.S. Appl. No. 12/719,337, Notice of Allowance mailed Mar. 11, 2015, 10 pgs.
U.S. Appl. No. 12/719,337, Notice of Non-Compliant Amendment mailed May 2, 2014, 3 pgs.
U.S. Appl. No. 12/719,337, Response filed Apr. 10, 2014 to Non Final Office Action mailed Jan. 10, 2014, 16 pgs.
U.S. Appl. No. 12/719,337, Response filed May 25, 2012 to Restriction Requirement mailed Apr. 26, 2012, 9 pgs.
U.S. Appl. No. 12/719,337, Response filed Jun. 5, 2013 to Final Office Action mailed Mar. 12, 2013, 16 pgs.
U.S. Appl. No. 12/719,337, Response filed Jun. 25, 2014 to Notice of Non-Compliant Amendment mailed May 2, 2014, 10 pgs.
U.S. Appl. No. 12/719,337, Response filed Sep. 18, 2014 to Final Office Action mailed Jul. 18, 2014, 13 pgs.
U.S. Appl. No. 12/718,337, Response filed Nov. 28, 2012 to Non Final Office Action mailed Sep. 5, 2012, 14 pgs.
U.S. Appl. No. 12/719,337, Restriction Requirement mailed Apr. 26, 2012, 8 pgs.
U.S. Appl. No. 12/788,973, Advisory Action mailed Jan. 23, 2013, 3 pgs.
U.S. Appl. No. 12/788,973, Advisory Action mailed Dec. 27, 2012, 8 pgs.
U.S. Appl. No. 12/788,973, Final Office Action mailed Sep. 18, 2012, 16 pgs.
U.S. Appl. No. 12/788,973, Non Final Office Action mailed May 8, 2012, 12 pgs.
U.S. Appl. No. 12/788,973, Notice of Allowance mailed Mar. 21, 2013, 6 pgs.
U.S. Appl. No. 12/788,973, Response filed Jan. 16, 2013 to Advisory Action mailed Dec. 27, 2012, 9 pgs.
U.S. Appl. No. 12/788,973, Response filed Jul. 19, 2012 to Non Final Office Action mailed May 8, 2012, 21 pgs.
U.S. Appl. No. 12/788,973, Response filed Dec. 16, 2011 to Restriction Requirement mailed Dec. 6, 2011, 11 pgs.
U.S. Appl. No. 12/788,973, Response filed Dec. 17, 2012 to Final Office Action mailed Sep. 18, 2012, 15 pgs.
U.S. Appl. No. 12/788,973, Restriction Requirement mailed Dec. 6, 2011, 9 pgs.
U.S. Appl. No. 12/788,973, Supplemental Notice of Allowance mailed May 24, 2013, 2 pgs.
U.S. Appl. No. 12/788,978, Advisory Action mailed Dec. 24, 2013, 4 pgs.
U.S. Appl. No. 12/788,978, Applicant's Summary of Examiner Interview filed Dec. 12, 2013, 2 pgs.
U.S. Appl. No. 12/788,978, Corrected Notice of Allowance mailed Apr. 30, 2014, 2 pgs.
U.S. Appl. No. 12/788,978, Examiner Interview Summary mailed Jan. 28, 2014, 3 pgs.
U.S. Appl. No. 12/788,978, Examiner Interview Summary mailed Mar. 22, 2013, 3 pgs.
U.S. Appl. No. 12/788,978, Examiner Interview Summary mailed Sep. 11, 2012, 3 pgs.
U.S. Appl. No. 12/788,978, Examiner Interview Summary mailed Oct. 29, 2013, 4 pgs.
U.S. Appl. No. 12/788,978, Examiner Interview Summary mailed Dec. 16, 2013, 3 pgs.
U.S. Appl. No. 12/788,978, Examiner Interview Summary mailed Dec. 27, 2012, 3 pgs.
U.S. Appl. No. 12/788,978, Final Office Action mailed Aug. 20, 2013, 17 pgs.
U.S. Appl. No. 12/788,978, Final Office Action mailed Nov. 2, 2012, 14 pgs.
U.S. Appl. No. 12/788,978, Non Final Office Action mailed Jan. 11, 2013, 16 pgs.
U.S. Appl. No. 12/788,978, Non Final Office Action mailed Jul. 13, 2012, 17 pgs.
U.S. Appl. No. 12/788,978, Notice of Allowance mailed Jan. 24, 2014, 9 pgs.
U.S. Appl. No. 12/788,978, Notice of Non-Compliant Amendment mailed Jun. 6, 2013, 3 pgs.
U.S. Appl. No. 12/788,978, Response filed Jan. 2, 2013 to Final Office Action mailed Nov. 2, 2012, 13 pgs.
U.S. Appl. No. 12/788,978, Response filed Jan. 20, 2014 to Advisory Action mailed Dec. 24, 2013, 4 pgs.
U.S. Appl. No. 12/788,978, Response filed Apr. 8, 2013 to Non Final Office Action mailed Jan. 11, 2013, 16 pgs.
U.S. Appl. No. 12/788,978, Response filed May 21, 2012 to Restriction Requirement mailed Apr. 20, 2012, 12 pgs.
U.S. Appl. No. 12/788,978, Response filed Jul. 3, 2013 to Notice of Non-Compliant Amendment mailed Jun. 6, 2013, 17 pgs.
U.S. Appl. No. 12/788,978, Response filed Oct. 5, 2012 to Non Final Office Action mailed Jul. 13, 2012, 20 pgs.
U.S. Appl. No. 12/788,978, Response filed Nov. 20, 2013 to Final Office Action mailed Aug. 20, 2013, 15 pgs.
U.S. Appl. No. 12/788,978, Restriction Requirement mailed Apr. 20, 2012, 8 pgs.
U.S. Appl. No. 12/828,977, Examiner Interview Summary mailed Jul. 9, 2012, 3 pgs.
U.S. Appl. No. 12/828,977, Non Final Office Action mailed May 3, 2012, 9 pgs.
U.S. Appl. No. 12/828,977, Notice of Allowance mailed Sep. 5, 2012, 9 pgs.
U.S. Appl. No. 12/828,977, Preliminary Amendment filed Jul. 19, 2011, 10 pgs.
U.S. Appl. No. 12/828,977, Response filed Mar. 14, 2012 to Restriction Requirement mailed Feb. 13, 2012, 9 pgs.
U.S. Appl. No. 12/828,977, Response filed Jul. 25, 2012 to Non Final Office Action mailed May 3, 2012, 11 pgs.
U.S. Appl. No. 12/828,977, Restriction Requirement mailed Feb. 13, 2012, 7 pgs.
U.S. Appl. No. 12/915,962, Examiner Interview Summary mailed Jul. 25, 2012, 3 pgs.
U.S. Appl. No. 12/915,962, Non Final Office Action mailed May 7, 2012, 11 pgs.
U.S. Appl. No. 12/915,962, Non Final Office Action mailed Oct. 15, 2012, 9 pgs.
U.S. Appl. No. 12/915,962, Notice of Allowance mailed Jun. 10, 2013, 12 pgs.
U.S. Appl. No. 12/915,962, Response filed Jan. 10, 2013 to Non Final Office Action mailed Oct. 15, 2012, 21 pgs.
U.S. Appl. No. 12/915,962, Response filed Mar. 16, 2012 to Restriction Requirement mailed Feb. 15, 2012, 15 pgs.

(56) References Cited

OTHER PUBLICATIONS

U.S. Appl. No. 12/915,962, Response filed Aug. 7, 2012 to Non Final Office Action mailed May 7, 2012, 26 pgs.
U.S. Appl. No. 12/915,962, Restriction Requirement mailed Feb. 15, 2012, 8 pgs.
U.S. Appl. No. 12/938,902, Examiner Interview Summary mailed Dec. 3, 2012, 3 pgs.
U.S. Appl. No. 12/976,328, Examiner Interview Summary mailed Feb. 13, 2012, 3 pgs.
U.S. Appl. No. 12/976,328, Non Final Office Action mailed Dec. 15, 2011, 13 pgs.
U.S. Appl. No. 12/976,328, Notice of Allowance mailed Apr. 30, 2012, 9 pgs.
U.S. Appl. No. 12/976,328, Response filed Mar. 2, 2012 to Non Final Office Action mailed Dec. 15, 2011, 15 pgs.
U.S. Appl. No. 13/045,689, Examiner Interview Summary mailed May 14, 2012, 3 pgs.
U.S. Appl. No. 13/045,689, Non Final Office Action mailed Mar. 20, 2012, 11 pgs.
U.S. Appl. No. 13/045,689, Notice of Allowance mailed Aug. 10, 2012, 10 pgs.
U.S. Appl. No. 13/045,689, Notice of Allowance mailed Sep. 24, 2012, 7 pgs.
U.S. Appl. No. 13/045,689, Response filed Jan. 30, 2012 to Restriction Requirement mailed Dec. 29, 2011, 13 pgs.
U.S. Appl. No. 13/045,689, Response filed Jun. 8, 2012 to Non Final Office Action mailed Mar. 20, 2012, 15 pgs.
U.S. Appl. No. 13/045,689, Restriction Requirement mailed Dec. 29, 2011, 6 pgs.
U.S. Appl. No. 13/045,691, Examiner Interview Summary mailed May 14, 2012, 3 pgs.
U.S. Appl. No. 13/045,691, Non Final Office Action mailed Mar. 20, 2012, 12 pgs.
U.S. Appl. No. 13/045,691, Notice of Allowance mailed Jun. 19, 2012, 10 pgs.
U.S. Appl. No. 13/045,691, Response filed Feb. 9, 2012 to Restriction Requirement mailed Jan. 9, 2012, 1 pg.
U.S. Appl. No. 13/045,691, Response filed Jun. 8, 2012 to Non Final Office Action mailed Mar. 20, 2012, 17 pgs.
U.S. Appl. No. 13/045,691, Restriction Requirement mailed Jan. 9, 2012, 6 pgs.
U.S. Appl. No. 13/071,563, Final Office Action mailed May 23, 2014, 13 pgs.
U.S. Appl. No. 13/071,563, Non Final Office Action mailed Oct. 23, 2013, 18 pgs.
U.S. Appl. No. 13/071,563, Notice of Allowance mailed Aug. 15, 2014, 7 pgs.
U.S. Appl. No. 13/071,563, Preliminary Amendment filed May 1, 2012, 8 pgs.
U.S. Appl. No. 13/071,563, Preliminary Amendment filed Dec. 6, 2011, 7 pgs.
U.S. Appl. No. 13/071,563, Response filed Jan. 21, 2014 to Non Final Office Action mailed Oct. 23, 2013, 13 pgs.
U.S. Appl. No. 13/071,563, Response filed Jul. 23, 2014 to Final Office Action mailed May 23, 2014, 14 pgs.
U.S. Appl. No. 13/071,563, Response filed Sep. 19, 2013 to Restriction Requirement mailed Aug. 9, 2013, 11 pgs.
U.S. Appl. No. 13/071,563, Restriction Requirement mailed Aug. 19, 2013, 7 pgs.
U.S. Appl. No. 13/098,897, Notice of Allowance mailed Jun. 11, 2013, 13 pgs.
U.S. Appl. No. 13/098,897, Response filed Aug. 30, 2012 to Restriction Requirement mailed Jul. 30, 2012, 16 pgs.
U.S. Appl. No. 13/098,897, Response filed Dec. 18, 2012 to Non Final Office Action mailed Sep. 21, 2012, 21 pgs.
U.S. Appl. No. 13/098,897, Restriction Requirement mailed Jul. 30, 2012, 8 pgs.
U.S. Appl. No. 13/098,927, Advisory Action mailed Aug. 8, 2013, 3 pgs.
U.S. Appl. No. 13/098,927, Applicant's Summary of Examiner Interview filed Sep. 23, 2013, 12 pgs.
U.S. Appl. No. 13/098,927, Examiner Interview Summary mailed Jun. 28, 2013, 3 pgs.
U.S. Appl. No. 13/098,927, Examiner Interview Summary mailed Sep. 20, 2013, 3 pgs.
U.S. Appl. No. 13/098,927, Notice of Allowance mailed Jan. 8, 2014, 5 pgs.
U.S. Appl. No. 13/098,927, Notice of Allowance mailed Sep. 26, 2013, 14 pgs.
U.S. Appl. No. 13/098,927, Response filed Jul. 22, 2015 to Final Office Action mailed May 22, 2013, 17 pgs.
U.S. Appl. No. 13/098,927, Response filed Aug. 27, 2012 to Restriction Requirement mailed Jul. 25, 2012, 14 pgs.
U.S. Appl. No. 13/098,927, Response filed Dec. 21, 2012 to Non Final Office Action mailed Sep. 24, 2012, 21 pgs.
U.S. Appl. No. 13/098,927, Restriction Requirement mailed Jul. 25, 2012, 8 pgs.
U.S. Appl. No. 13/109,667, Advisory Action mailed Feb. 4, 2014, 4 pgs.
U.S. Appl. No. 13/109,667, Examiner Interview Summary mailed Dec. 20, 2013, 3 pgs.
U.S. Appl. No. 13/109,667, Final Office Action mailed Oct. 11, 2013, 19 pgs.
U.S. Appl. No. 13/109,667, Non Final Office Action mailed May 21, 2013, 21 pgs.
U.S. Appl. No. 13/109,667, Notice of Allowance mailed Feb. 18, 2014, 10 pgs.
U.S. Appl. No. 13/109,667, Response filed Jan. 13, 2014 to Final Office Action mailed Oct. 11, 2013, 20 pgs.
U.S. Appl. No. 13/109,667, Response filed May 2, 2013 to Restriction Requirement mailed Apr. 2, 2013, 1 pg.
U.S. Appl. No. 13/109,667, Response filed Aug. 21, 2013 to Non Final Office Action mailed May 21, 2013, 27 pgs.
U.S. Appl. No. 13/109,667, Restriction Requirement mailed Apr. 2, 2013, 8 pgs.
U.S. Appl. No. 13/109,667, Supplemental Notice of Allowability mailed Jun. 12, 2014, 3 pgs.
U.S. Appl. No. 13/109,667, Supplemental Notice of Allowance mailed May 28, 2014, 2 pgs.
U.S. Appl. No. 13/109,667, Supplemental Preliminary Amendment filed Feb. 4, 2014, 16 pgs.
U.S. Appl. No. 13/109,672, 312 Amendment filed Jan. 15, 2015, 3 pgs.
U.S. Appl. No. 13/109,672, Non Final Office Action mailed May 15, 2014, 10 pgs.
U.S. Appl. No. 13/109,672, Notice of Allowance mailed Feb. 3, 2015, 2 pgs.
U.S. Appl. No. 13/109,672, Notice of Allowance mailed Sep. 29, 2014, 9 pgs.
U.S. Appl. No. 13/109,672, PTO Response to Rule 312 Communication mailed Jan. 27, 2015, 2 pgs.
U.S. Appl. No. 13/109,672, Response filed Apr. 14, 2014 to Restriction Requirement mailed Feb. 14, 2014, 15 pgs.
U.S. Appl. No. 13/109,672, Response filed Aug. 15, 2014 to Non Final Office Action mailed May 15, 2014, 20 pgs.
U.S. Appl. No. 0 ,672, Response filed Nov. 4, 2013 to Restriction Requirement mailed Oct. 2, 2013, 10 pgs.
U.S. Appl. No. 13/109,672, Restriction Requirement mailed Feb. 14, 2014, 7 pgs.
U.S. Appl. No. 13/109,672, Restriction Requirement mailed Oct. 2, 2013, 7 pgs.
U.S. Appl. No. 13/111,564, Corrected Notice of Allowance mailed Oct. 9, 2013, 2 pgs.
U.S. Appl. No. 13/111,564, Examiner Interview Summary mailed Jun. 18, 2013, 3 pgs.
U.S. Appl. No. 13/111,564, Non Final Office Action mailed Mar. 18, 2013, 8 pgs.
U.S. Appl. No. 13/111,564, Notice of Allowance mailed Jun. 28, 2013, 12 pgs.
U.S. Appl. No. 13/111,564, Response filed Feb. 4, 2013 to Restriction Requirement mailed Jan. 3, 2013, 20 pgs.

(56) References Cited

OTHER PUBLICATIONS

U.S. Appl. No. 13/111,564, Response filed Jun. 18, 2013 to Non Final Office Action mailed Mar. 18, 2013, 25 pgs.
U.S. Appl. No. 13/111,564, Restriction Requirement mailed Jan. 3, 2013, 5 pgs.
U.S. Appl. No. 13/177,153, Final Office Action mailed May 28, 2013, 11 pgs.
U.S. Appl. No. 13/177,153, Non Final Office Action mailed Oct. 2, 2012, 11 pgs.
U.S. Appl. No. 13/177,153, Notice of Allowance mailed Jan. 7, 2014, 4 pgs.
U.S. Appl. No. 13/177,153, Notice of Allowance mailed Sep. 17, 2013, 13 pgs.
U.S. Appl. No. 13/177,153, Response filed Aug. 28, 2013 to Final Office Action mailed May 28, 2013, 19 pgs.
U.S. Appl. No. 13/177,153, Response filed Sep. 4, 20712 to Restriction Requirement mailed Aug. 2, 2012, 15 pgs.
U.S. Appl. No. 13/177,15 , Response filed Dec. 20, 2012 to Non Final Office Action mailed Oct. 20, 2012, 16 pgs.
U.S. Appl. No. 13/177,153, Restriction Requirement mailed Aug. 2, 2012, 9 pgs.
U.S. Appl. No. 13/181,729, Examiner Interview Summary mailed May 9, 2013, 3 pgs.
U.S. Appl. No. 13/181,729, Notice of Allowance mailed May 23, 2013, 9 pgs.
U.S. Appl. No. 13/181,729, Response filed May 13, 2013 to Final Office Action mailed Mar. 13, 2013, 13 pgs.
U.S. Appl. No. 13/181,729, Response filed Dec. 20, 2012 to Non Final Office Action mailed Oct. 2, 2012, 15 pgs.
U.S. Appl. No. 13/269,097, Final Office Action mailed Aug. 8, 2013, 7 pgs.
U.S. Appl. No. 13/269,097, Non Final Office Action mailed Feb. 12, 2013, 10 pgs.
U.S. Appl. No. 13/269,097, Notice of Allowance mailed Feb. 3, 2014, 5 pgs.
U.S. Appl. No. 13/269,097, Notice of Allowance mailed Oct. 21, 2013, 9 pgs.
U.S. Appl. No. 13/269,097, Response filed May 13, 2013 to Non Final Office Action mailed Feb. 12, 2013, 17 pgs.
U.S. Appl. No. 13/269,097, Response filed Oct. 8, 2013 to Final Office Action mailed Aug. 8, 2013, 12 pgs.
U.S. Appl. No. 13/269,097, Response filed Nov. 13, 2012 to Restriction Requirement mailed Oct. 17, 2012, 1 pg.
U.S. Appl. No. 13/269,097, Restriction Requirement mailed Oct. 17, 2012, 8 pgs.
U.S. Appl. No. 13/278,341, Notice of Allowance mailed Jun. 18, 2013, 10 pgs.
U.S. Appl. No. 13/278,341, Response filed Mar. 8, 2013 to Restriction Requirement Feb. 11, 2013, 1 pg.
U.S. Appl. No. 13/278,341, Restriction Requirement mailed Feb. 11, 2013, 6 pgs.
U.S. Appl. No. 13/281,009, Non Final Office Action mailed Jun. 2, 2015, 9 pgs.
U.S. Appl. No. 13/281,009, Notice of Allowance mailed Feb. 24, 2016, 9 pgs.
U.S. Appl. No. 13/281,009, Notice of Allowance mailed Oct. 29, 2015, 8 pgs.
U.S. Appl. No. 13/281,009, Response filed Sep. 2, 2015 to Non Final Office Action mailed Jun. 2, 2015, 13 pgs.
U.S. Appl. No. 13/281,009, Restriction Requirement mailed Feb. 11, 2015, 6 pgs.
U.S. Appl. No. 13/288,463, Examiner Interview Summary mailed Jun. 3, 2014, 3 pgs.
U.S. Appl. No. 13/288,463, Non Final Office Action mailed Feb. 24, 2014, 13 pgs.
U.S. Appl. No. 13/288,463, Notice of Allowance mailed Aug. 27, 2014, 9 pgs.
U.S. Appl. No. 13/288,463, Response filed May 27, 2014 to Non Final Office Action mailed Feb. 24, 2014, 15 pgs.
U.S. Appl. No. 13/288,463, Supplemental Notice of Allowability mailed Dec. 8, 2014, 5 pgs.
U.S. Appl. No. 13/288,463, Supplemental Notice of Allowability mailed Dec. 19, 2014, 5 pgs.
U.S. Appl. No. 13/293,825, Notice of Allowability mailed Jun. 22, 2015, 7 pgs.
U.S. Appl. No. 13/293,825, Notice of Allowance mailed May 19, 2015, 9 pgs.
U.S. Appl. No. 13/293,825, Response filed Apr. 15, 2015 to Restriction Requirement mailed Feb. 12, 2015, 17 pgs.
U.S. Appl. No. 13/293,825, Restriction Requirement mailed Feb. 12, 2015, 9 pgs.
U.S. Appl. No. 13/295,126, Non Final Office Action mailed May 19, 2015, 9 pgs.
U.S. Appl. No. 13/295,126, Notice of Allowance mailed Oct. 22, 2015, 9 pgs.
U.S. Appl. No. 13/295,126, Response filed Apr. 13, 2015 to Restriction Requirement mailed Feb. 12, 2015, 1 pgs.
U.S. Appl. No. 13/295,126, Response filed Aug. 17, 2015 to Non Final Office Action mailed May 19, 2015, 21 pgs.
U.S. Appl. No. 13/295,126, Restriction Requirement mailed Feb. 12, 2015, 9 pgs.
U.S. Appl. No. 13/311,936, Examiner Interview Summary mailed Feb. 12, 2015, 2 pgs.
U.S. Appl. No. 13/311,936, Non Final Office Action mailed Feb. 9, 2015, 13 pgs.
U.S. Appl. No. 13/311,936, Non Final Office Action mailed Oct. 19, 2015, 8 pgs.
U.S. Appl. No. 13/311,936, Notice of Allowance mailed Mar. 29, 2016, 8 pgs.
U.S. Appl. No. 13/311,936, Response filed Jan. 18, 2016 to Non Final Office Action mailed Oct. 19, 2015, 8 pgs.
U.S. Appl. No. 13/311,936, Response filed Jun. 9, 2015 to Non Final Office Action mailed Feb. 9, 2015, 12 pgs.
U.S. Appl. No. 13/311,936, Response filed Oct. 3, 2014 to Restriction Requirement mailed Aug. 5, 2014, 10 pgs.
U.S. Appl. No. 13/311,936, Restriction Requirement mailed Aug. 5, 2014, 7 pgs.
U.S. Appl. No. 13/350,985, Final Office Action mailed Apr. 16, 2015, 8 pgs.
U.S. Appl. No. 13/350,985, Non Final Office Action mailed Dec. 15, 2014, 8 pgs.
U.S. Appl. No. 13/350,985, Notice of Allowance mailed Jul. 27, 2015, 5 pgs.
U.S. Appl. No. 13/350,985, Response filed Mar. 13, 2015 to Non Final Office Action mailed Dec. 15, 2014, 10 pgs.
U.S. Appl. No. 13/350,985, Response filed Jul. 9, 2015 to Final Office Action mailed Apr. 16, 2015, 8 pgs.
U.S. Appl. No. 13/350,985, Response filed Dec. 2, 2014 to Restriction Requirement mailed Oct. 2, 2014, 9 pgs.
U.S. Appl. No. 13/350,985, Restriction Requirement mailed Oct. 2, 2014, 6 pgs.
U.S. Appl. No. 13/399,125, Corrected Notice of Allowance mailed Aug. 28, 2014, 2 pgs.
U.S. Appl. No. 13/399,125, Examiner Interview Summary mailed May 17, 2013, 3 pgs.
U.S. Appl. No. 13/399,125, Notice of Allowance mailed May 16, 2014, 8 pgs.
U.S. Appl. No. 13/399,125, Response filed Jan. 10, 2013 to Non Final Office Action mailed Oct. 24, 2012, 15 pgs.
U.S. Appl. No. 13/399,125, Response filed May 20, 2013 to Final Office Action mailed Mar. 20, 2013, 14 pgs.
U.S. Appl. No. 13/412,105, Advisory Action mailed Feb. 24, 2014, 3 pgs.
U.S. Appl. No. 13/412,105, Examiner Interview Summary mailed Feb. 6, 2014, 3 pgs.
U.S. Appl. No. 13/412,105, Examiner Interview Summary mailed Oct. 11, 2013, 3 pgs.
U.S. Appl. No. 13/412,105, Non Final Office Action mailed Jul. 15, 2013, 10 pgs.
U.S. Appl. No. 13/412,105, Notice of Allowance mailed Aug. 18, 2014, 9 pgs.

(56) References Cited

OTHER PUBLICATIONS

U.S. Appl. No. 13/412,105, Response filed Feb. 10, 2014 to Final Office Action mailed Dec. 13, 2013, 14 pgs.
U.S. Appl. No. 13/412,105, Response filed Mar. 13, 2014 to Advisory Action mailed Feb. 24, 2014, 19 pgs.
U.S. Appl. No. 13/412,105, Response filed May 6, 2013 to Restriction Requirement mailed Apr. 5, 2013, 9 pgs.
U.S. Appl. No. 13/412,105, Response filed Oct. 14, 2013 to Non Final Office Action mailed Jul. 15, 2013, 13 pgs.
U.S. Appl. No. 13/412,105, Restriction Requirement mailed Apr. 5, 2013, 9 pgs.
U.S. Appl. No. 13/412,116, Corrected Notice of Allowance mailed Jun. 2, 2014, 2 pgs.
U.S. Appl. No. 13/412,116, Examiner Interview Summary mailed Dec. 13, 2013, 3 pgs.
U.S. Appl. No. 13/412,116, Notice of Allowance mailed Feb. 19, 2014, 9 pgs.
U.S. Appl. No. 13/412,116, Response filed Jul. 3, 2013 to Restriction Requirement mailed Jun. 19, 2013, 1 pg.
U.S. Appl. No. 13/412,116, Response filed Dec. 11, 2013 to Non Final Office Action mailed Sep. 11, 2013, 11 pgs.
U.S. Appl. No. 13/412 Restriction Requirement mailed Jun. 19, 2013, 9 pgs.
U.S. Appl. No. 13/412,127, Examiner Interview Summary mailed Nov. 5, 2013, 3 pgs.
U.S. Appl. No. 13/412,127, Response filed May 23, 2013 to Restriction Requirement mailed Apr. 24, 2013, 2 pgs.
U.S. Appl. No. 13/412,127, Response filed Nov. 5, 2013 to Non Final Office Action mailed Aug. 7, 2013, 16 pgs.
U.S. Appl. No. 13/412,127, Restriction Requirement mailed Apr. 24, 2013, 10 pgs.
U.S. Appl. No. 13/587,374, Final Office Action mailed Nov. 6, 2013, 9 pgs.
U.S. Appl. No. 13/587,374, Notice of Allowance mailed Feb. 28, 2014, 5 pgs.
U.S. Appl. No. 13/587,374, Preliminary Amendment filed Jun. 21, 2013, 9 pgs.
U.S. Appl. No. 13/587,374, Response filed Jan. 24, 2014 to Final Office Action mailed Nov. 6, 2013, 15 pgs.
U.S. Appl. No. 13/587,374, Response filed Oct. 14, 2013 to Non Final Office Action mailed Jul. 17, 2013, 14 pgs.
U.S. Appl. No. 13/625,413, Final Office Action mailed Oct. 30, 2015, 8 pgs.
U.S. Appl. No. 13/625,413, Non Final Office Action mailed Jun. 8, 2015, 11 pgs.
U.S. Appl. No. 13/625,413, Notice of Allowance mailed Apr. 1, 2016, 8 pgs.
U.S. Appl. No. 13/625,413, Notice of Allowance mailed Dec. 11, 2015, 9 pgs.
U.S. Appl. No. 13/625,413, Response filed May 11, 2015 to Restriction Requirement mailed Mar. 10, 2015, 1 pg.
U.S. Appl. No. 13/625,413, Response filed Sep. 8, 2015 to Non Final Office Action mailed Jun. 8, 2015, 16 pgs.
U.S. Appl. No. 13/625,413, Response filed Dec. 1, 2015 to Final Office Action mailed Oct. 30, 2015, 9 pgs.
U.S. Appl. No. 13/625.413, Restriction Requirement mailed Mar. 10, 2015, 7 pgs.
U.S. Appl. No. 13/645,964, Advisory Action mailed Feb. 4, 2016, 2 pgs.
U.S. Appl. No. 13/645,964, Final Office Action mailed Oct. 6, 2015, 17 pgs.
U.S. Appl. No. 13/645,964, Non Final Office Action mailed Mar. 15, 2016, 15 pgs.
U.S. Appl. No. 13/645,964, Non Final Office Action mailed Mar. 17, 2015, 15 pgs.
U.S. Appl. No. 13/645,964, Response filed Jul. 17, 2015 to Non Final Office Action mailed Mar. 17, 2015, 17 pgs.
U.S. Appl. No. 13/645,964, Response filed Dec. 4, 2015 to Final Office Action mailed Oct. 6, 2015, 14 pgs.
U.S. Appl. No. 13/656,821, Notice of Allowance mailed Jun. 18, 2015, 11 pgs.
U.S. Appl. No. 13/656,821, Response filed May 11, 2015 to Restriction Requirement mailed Mar. 10, 2015, 1 pg.
U.S. Appl. No. 13/656,821, Restriction Requirement mailed Mar. 10, 2015, 6 pgs.
U.S. Appl. No. 13/720,648, Final Office Action mailed Nov. 16, 2015, 7 pgs.
U.S. Appl. No. 13/720,648, Non Final Office Action mailed Jun. 10, 2015, 11 pgs.
U.S. Appl. No. 13/720,648, Notice of Allowance mailed Feb. 5, 2016, 11 pgs.
U.S. Appl. No. 13/720,648, Response filed Jan. 13, 2016 to Final Office Action mailed Nov. 16, 2015, 9 pgs.
U.S. Appl. No. 13/720,648, Response filed May 11, 2015 to Restriction Requirement mailed Mar. 10, 2015, 8 pgs.
U.S. Appl. No. 13/720,648, Response filed Oct. 9, 2015 to Non Final Office Action mailed Jun. 10, 2015, 23 pgs.
U.S. Appl. No. 13/720,648, Restriction Requirement mailed Mar. 10, 2015, 8 pgs.
U.S. Appl. No. 13/721,970, Notice of Allowance mailed Aug. 12, 2013, 13 pgs.
U.S. Appl. No. 13/721,970, Preliminary Amendment filed Mar. 15, 2013, 13 pgs.
U.S. Appl. No. 13/721,970, Response filed May 8, 2013 to Restriction Requirement mailed Apr. 11, 2013, 1 pgs.
U.S. Appl. No. 13/721,970, Restriction Requirement mailed Apr. 11, 2013, 6 pgs.
U.S. Appl. No. 13/751,846, Final Office Action mailed Nov. 17, 2015, 9 pgs.
U.S. Appl. No. 13/751,846, Non Final Office Action mailed Jun. 15, 2015, 10 pgs.
U.S. Appl. No. 13/751,846, Notice of Allowance mailed Mar. 16, 2016, 11 pgs.
U.S. Appl. No. 13/751,846, Response filed Feb. 5, 2016 to Final Office Action mailed Nov. 17, 2015, 14 pgs.
U.S. Appl. No. 13/751,846, Response filed May 11, 2015 to Restriction Requirement mailed Mar. 10, 2015, 15 pgs.
U.S. Appl. No. 13/751,846, Response filed Oct. 9, 2015 to Non Final Office Action mailed Jun. 15, 2015, 20 pgs.
U.S. Appl. No. 13/751,846, Restriction Requirement mailed Mar. 10, 2015, 7 pgs.
U.S. Appl. No. 13/757,003, Non Final Office Action mailed Jun. 25, 2015, 8 pgs.
U.S. Appl. No. 13/757,003, Notice of Allowance mailed Feb. 8, 2016, 10 pgs.
U.S. Appl. No. 13/757,003, Response filed May 12, 2015 to Restriction Requirement mailed Mar. 12, 2015, 9 pgs.
U.S. Appl. No. 13/757,00 , Response filed Oct. 26, 2015 to Non Final Office Action mailed Jul. 25, 2015, 8 pgs.
U.S. Appl. No. 13/757,003, Restriction Requirement mailed Mar. 12, 2015, 6 pgs.
U.S. Appl. No. 13/757,019, Non Final Office Action mailed Jun. 25, 2015, 11 pgs.
U.S. Appl. No. 13/757,01 , Notice of Allowance mailed Dec. 10, 2015, 10 pgs.
U.S. Appl. No. 13/757,019, Response filed May 11, 2015 to Restriction Requirement mailed Mar. 11, 2015, 9 pgs.
U.S. Appl. No. 13/757,019, Response filed Oct. 26, 2015 to Non Final Office Action mailed Jun. 25, 2015, 9 pgs.
U.S. Appl. No. 13/757,019, Restriction Requirement mailed Mar. 11, 2015, 10 pgs.
U.S. Appl. No. 13/767,401, Non Final Office Action mailed Aug. 26, 2015, 9 pgs.
U.S. Appl. No. 13/767,401, Notice of Allowance mailed Apr. 8, 2016, 9 pgs.
U.S. Appl. No. 13/767,401, Notice of Allowance mailed Dec. 30, 2015, 9 pgs.
U.S. Appl. No. 13/767,401, Response filed May 18, 2015 to Restriction Requirement mailed Mar. 17, 2015, 15 pgs.
U.S. Appl. No. 13/767,401, Response filed Nov. 6, 2015 to Non Final Office Action mailed Aug. 26, 2015, 12 pgs.

(56) References Cited

OTHER PUBLICATIONS

U.S. Appl. No. 13/767,401, Restriction Requirement mailed Mar. 17, 2015, 8 pgs.
U.S. Appl. No. 13/790,982, Examiner Interview Summary mailed Jun. 9, 2015, 3 pgs.
U.S. Appl. No. 13/790,982, Non Final Office Action mailed Sep. 16, 2015, 11 pgs.
U.S. Appl. No. 13/790,982, Notice of Allowance mailed Feb. 24, 2016, 10 pgs.
U.S. Appl. No. 13/790,982, Response filed Jun. 2, 2015 to Restriction Requirement mailed Apr. 2, 2015, 11 pgs.
U.S. Appl. No. 13/790,982, Response filed Dec. 16, 2015 to Non Final Office Action mailed Sep. 16, 2015, 10 pgs.
U.S. Appl. No. 13/790,982, Restriction Requirement mailed Apr. 2, 2015, 10 pgs.
U.S. Appl. No. 13/790,997, Examiner Interview Summary mailed Jun. 8, 2015, 3 pgs.
U.S. Appl. No. 13/790,997, Non Final Office Action mailed Sep. 21, 2015, 8 pgs.
U.S. Appl. No. 13/790,997, Notice of Allowance mailed Mar. 2, 2016, 9 pgs.
U.S. Appl. No. 13/790,997, Response filed Jun. 2, 2015 to Restriction Requirement mailed Apr. 2, 2015, 12 pgs.
U.S. Appl. No. 13/790,997, Response filed Dec. 18, 2015 to Non Final Office Action mailed Sep. 21, 2015, 9 pgs.
U.S. Appl. No. 13/790,997, Restriction Requirement mailed Apr. 2, 2015, 8 pgs.
U.S. Appl. No. 13/791,014, Final Office Action mailed Jan. 8, 2016, 11 pgs.
U.S. Appl. No. 13/791,014, Non Final Office Action mailed Aug. 14, 2015, 9 pgs.
U.S. Appl. No. 13/791,014, Response filed Aug. 3, 2015 to Restriction Requirement mailed May 1, 2015, 9 pgs.
U.S. Appl. No. 13/791,014, Response filed Nov. 10, 2015 to Non Final Office Action mailed Aug. 14, 2015, 13 pgs.
U.S. Appl. No. 13/791,014, Restriction Requirement mailed May 1, 2015, 6 pgs.
U.S. Appl. No. 13/833,567, Final Office Action mailed Mar. 9, 2016, 9 pgs.
U.S. Appl. No. 13/833,567, Non Final Office Action mailed Oct. 23, 2015, 10 pgs.
U.S. Appl. No. 13/833,567, Response filed Jan. 22, 2016 to Non Final Office Action mailed Oct. 23, 2015, 11 pgs.
U.S. Appl. No. 13/833,567, Response filed Jun. 25, 2015 to Restriction Requirement mailed Apr. 3, 2015, 10 pgs.
U.S. Appl. No. 13/833,567, Restriction Requirement mailed Apr. 3, 2015, 6 pgs.
U.S. Appl. No. 13/838,755, Final Office Action mailed Feb. 22, 2016, 9 pgs.
U.S. Appl. No. 13/838,755, Non Final Office Action mailed Sep. 17, 2015, 11 pgs.
U.S. Appl. No. 13/838,755, Response filed Jun. 8, 2015 to Restriction Requirement mailed Apr. 6, 2015, 1 pg.
U.S. Appl. No. 13/838,755, Response filed Dec. 1, 2015 to Non Final Office Action mailed Sep. 17, 2015, 13 pgs.
U.S. Appl. No. 13/838,755, Restriction Requirement mailed Apr. 6, 2015, 6 pgs.
U.S. Appl. No. 13/889,851, Non Final Office Action mailed Apr. 6, 2015, 10 pgs.
U.S. Appl. No. 13/889,851, Notice of Allowance mailed Aug. 12, 2015, 8 pgs.
U.S. Appl. No. 13/889,851, Response filed Feb. 26, 2015 to Restriction Requirement mailed Jan. 21, 2015, 12 pgs.
U.S. Appl. No. 13/889,851, Response filed Jul. 16, 2015 to Non Final Office Action mailed Apr. 6, 2015, 14 pgs.
U.S. Appl. No. 13/889,851, Restriction Requirement mailed Jan. 21, 2015, 6 pgs.
U.S. Appl. No. 13/889,851, Supplemental Amendment and Response filed Jul. 6, 2015 to Non Final Office Action mailed Apr. 6, 2015, 8 pgs.
U.S. Appl. No. 13/959,145, Final Office Action mailed Jan. 29, 2016, 16 pgs.
U.S. Appl. No. 13/959,145, Final Office Action mailed Feb. 5, 2015, 22 pgs.
U.S. Appl. No. 13/959,145, Non Final Office Action mailed Jul. 31, 2015, 21 pgs.
U.S. Appl. No. 13/959,145, Non Final Office Action mailed Sep. 15, 2014, 20 pgs.
U.S. Appl. No. 13/959,145, Response filed Mar. 28, 2016 to Final Office Action mailed Jan. 29, 2016, 10 pgs.
U.S. Appl. No. 13/959,145, Response filed Jul. 6, 2015 to Final Office Action mailed Feb. 5, 2015, 18 pgs.
U.S. Appl. No. 13/959,145, Response filed Oct. 30, 2015 to Non Final Office Action mailed Jul. 31, 2015, 14 pgs.
U.S. Appl. No. 13/959,145, Response filed Dec. 15, 2014 to Non Final Office Action mailed Sep. 15, 2014, 21 pgs.
U.S. Appl. No. 14/055,172, Restriction Requirement mailed Mar. 4, 2016, 6 pgs.
U.S. Appl. No. 14/055,191, Restriction Requirement mailed Mar. 7, 2016, 6 pgs.
U.S. Appl. No. 14/071,295, Non Final Office Action mailed Aug. 15, 2014, 6 pgs.
U.S. Appl. No. 14/071,295, Notice of Allowance mailed Dec. 10, 2014, 8 pgs.
U.S. Appl. No. 14/071,295, Response filed Nov. 17, 2014 to Non Final Office Action mailed Aug. 15, 2014, 14 pgs.
U.S. Appl. No. 14/071,295, Supplemental Notice of Allowability mailed Jan. 26, 2015, 2 pgs.
U.S. Appl. No. 14/095,614, Preliminary Amendment filed Apr. 15, 2014, 17 pgs.
U.S. Appl. No. 14/107,350, Notice of Allowance mailed Feb. 26, 2016, 11 pgs.
U.S. Appl. No. 14/107,350, Preliminary Amendment filed Feb. 28, 2014, 4 pgs.
U.S. Appl. No. 14/211,977, Preliminary Amendment filed Mar. 2, 2016, 7 pgs.
U.S. Appl. No. 14/211,977, Restriction Requirement mailed Mar. 11, 2016, 6 pgs.
U.S. Appl. No. 14/275,548, Non Final Office Action mailed Feb. 19, 2016, 14 pgs.
U.S. Appl. No. 14/324,688, Non Final Office Action mailed Jan. 8, 2016, 18 pgs.
U.S. Appl. No. 14/324,688, Response filed Apr. 8, 2016 to Non Final Office Action mailed Jan. 8, 2016, 15 pgs.
U.S. Appl. No. 14/456,286, Non Final Office Action mailed Dec. 30, 2015, 16 pgs.
U.S. Appl. No. 14/456,286, Response filed Mar. 30, 2016 to Non Final Office Action mailed Dec. 30, 2015, 15 pgs.
U.S. Appl. No. 14/456,286, Response filed Dec. 11, 2015 to Restriction Requirement mailed Oct. 29, 2015, 6 pgs.
U.S. Appl. No. 14/456,286, Restriction Requirement mailed Oct. 29, 2015, 9 pgs.
U.S. Appl. No. 14/589,101, Final Office Action mailed Oct. 2, 2015, 10 pgs.
U.S. Appl. No. 14/589,101, Non Final Office Action mailed Feb. 12, 2015, 10 pgs.
U.S. Appl. No. 14/589,101, Response filed Jun. 12, 2015 to Non Final Office Action mailed Feb. 12, 2015, 11 pgs.
U.S. Appl. No. 14/589,101, Response filed Dec. 29, 2015 to Final Office Action mailed Oct. 2, 2015, 15 pgs.
U.S. Appl. No. 14/697,140, Non Final Office Action mailed Apr. 8, 2016, 8 pgs.
U.S. Appl. No. 14/794,309, Preliminary Amendment filed Sep. 22, 2015, 6 pgs.
U.S. Appl. No. 14/794,309, Supplemental Preliminary Amendment filed Mar. 3, 2016, 8 pgs.
U.S. Appl. No. 14/876,167, Preliminary Amendment filed Oct. 27, 2015, 8 pgs.
U.S. Appl. No. 14/936,831, Preliminary Amendment filed Nov. 11, 2015, 6 pgs.
U.S. Appl. No. 14/956,724, Preliminary Amendment filed Dec. 7, 2015, 8 pgs.

(56) References Cited

OTHER PUBLICATIONS

U.S. Appl. No. 14/956,724, Supplemental Preliminary Amendment filed Feb. 11, 2016, 7 pgs.
U.S. Appl. No. 14/983,108, Preliminary Amendment filed Dec. 30, 2015, 7 pgs.
U.S. Appl. No. 14/983,747, Preliminary Amendment filed Jan. 4, 2016, 5 pgs.
U.S. Appl. No. 15/060,007, Preliminary Amendment filed Mar. 9, 2016, 9 pgs.
U.S. Appl. No. 15/061,352, Preliminary Amendment filed Mar. 7, 2016, 8 pgs.
U.S. Appl. No. 15/074,553, Preliminary Amendment filed Mar. 21, 2016, 8 pgs.
U.S. Appl. No. 12/938,902, Non Final Office Action mailed Sep. 17, 2012, 11 pgs.
U.S. Appl. No. 12/938,902, Notice of Allowance mailed Jun. 21, 2013, 13 pgs.
U.S. Appl. No. 12/938,902, Notice of Allowance mailed Oct. 1, 2013, 9 pgs.
U.S. Appl. No. 12/938,902, Response filed Aug. 6, 2012 to Restriction Requirement mailed Jul. 6, 2012, 14 pgs.
U.S. Appl. No. 12/938,902, Response filed Dec. 10, 2012 to Non Final Office Action mailed Sep. 17, 2012, 20 pgs.
U.S. Appl. No. 12/938,902, Restriction Requirement mailed Jul. 6, 2012, 8 pgs.
Bio-Intrafix Tibial Soft Tissue Fasteners, Building on the Legacy of IntraFix, (Feb. 2007), 6 pgs.
European Application Serial No. 10727548.9, Examination Notification Art. 94(3) mailed Sep. 18, 2014, 6 pgs.
European Application Serial No. 10727548.9, Office Action mailed Jan. 19, 2012, 2 pgs.
European Application Serial No. 10727548.9, Response filed Mar. 19, 2015 to Examination Notification Art. 94(3) mailed Sep. 18, 2014, 23 pgs.
European Application Serial No. 11707316.3, Examination Notification Art. 94(3) mailed Feb. 4, 2014, 3 pgs.
European Application Serial No. 11707316.3, Examination Notification Art. 94(3) mailed Dec. 17, 2014, 5 pgs.
European Application Serial No. 11707316.3, Office Action mailed Nov. 10, 2015, 6 pgs.
European Application Serial No. 11707316.3, Response filed Jun. 5, 2014 to Examination Notification Art. 94(3) mailed Feb. 4, 2014, 7 pgs.
European Application Serial No. 11707316.3, Response filed Jun. 29, 2015 to Examination Notification Art. 94(3) mailed Dec. 17, 2014, 25 pgs.
European Application Serial No. 12721676.0, Communication pursuant to Article 94(3) EPC mailed Sep. 30, 2015, 4 pgs.
European Application Serial No. 12721676.0, Office Action mailed Jan. 3, 2014, 2 pgs.
European Application Serial No. 12721676.0, Preliminary Amendment filed Nov. 19, 2013, 9 pgs.
European Application Serial No. 12721676.0, Response filed Jul. 10, 2014 to Office Action mailed Jan. 3, 2014, 2 pgs.
European Application Serial No. 12791902.5, Examination Notification Art. 94(3) mailed Aug. 14, 2015, 4 pgs.
European Application Serial No. 12791902.5, Office Action mailed Jul. 15, 2014, 2 pgs.
European Application Serial No. 12806211.4, Examination Notification Art. 94(3) mailed Aug. 13, 2015, 5 pgs.
European Application Serial No. 12806211.4, Office Action mailed Jul. 18, 2014, 2 pgs.
European Application Serial No. 13818131.8, Office Action mailed Jul. 28, 2015, 2 pgs.
European Application Serial No. 13818131.8, Response filed Feb. 8, 2016 to Office Action mailed Jul. 28, 2015, 14 pgs.
European Application Serial No. 14716173.1, Office Action mailed Nov. 5, 2015, 2 pgs.
International Application Serial No. PCT/US2009/039580, International Preliminary Report on Patentability mailed Nov. 4, 2010, 9 pgs.
International Application Serial No. PCT/US2009/039580, International Search Report mailed Jul. 30, 2009, 4 pgs.
International Application Serial No. PCT/US2009/039580, Written Opinion mailed Jul. 30, 2009, 7 pgs.
International Application Serial No. PCT/US2010/036602, International Preliminary Report on Patentability mailed Dec. 8, 2011, 9 pgs.
International Application Serial No. PCT/US2010/036602, International Search Report mailed Nov. 8, 2010, 6 pgs.
International Application Serial No. PCT/US2010/036602, Written Opinion mailed Nov. 8, 2010, 7 pgs.
International Application Serial No. PCT/US2012/030294, International Preliminary Report on Patentability mailed Oct. 10, 2013, 9 pgs.
International Application Serial No. PCT/US2012/030294, International Search Report mailed May 23, 2012, 6 pgs.
International Application Serial No. PCT/US2012/030294.Written Opinion mailed May 23, 2012, 7 pgs.
International Application Serial No. PCT/US2012/037703, Written Opinion mailed Nov. 28, 2013.
International Application Serial No. PCT/US2012/062738, International Preliminary Report on Patentability mailed May 15, 2014, 9 pgs.
International Application Serial No. PCT/US2012/062738, International Search Report mailed Mar. 6, 2013, 6 pgs.
International Application Serial No. PCT/US2012/062738, Written Opinion mailed Mar. 6, 2013, 7 pgs.
International Application Serial No. PCT/US2013/075989, International Preliminary Report on Patentability mailed Jul. 2, 2015, 10 pgs.
International Application Serial No. PCT/US2014/026413, International Preliminary Report on Patentability mailed Sep. 24, 2015, 10 pgs.
Mallory-Head Modular Calcar Revision System, Biomet Orthopedics, Inc., (2006), 20 pgs.
SportMesh™ Soft Tissue Reinforcrnent, Made from . . . Artelon® optimal tissue repair, Biomet® Sports Medicine, Inc., (2007), 8 pgs.
Alford, J Winslow, et al., "Cartilage Restoration, Part 1. Basic Science, Historical Perspective, Patient Evaluation, and Treatment Options", The American Journal of Sports Medicine, 33(2), (2005), 295-306.
Anitua, Eduardo, et al., "Autologous platelets as a source of proteins for healing and tissue regeneration"Thromb Haemost, vol. 91 (2004), 4-15.
Edwards, Andrew, at al., "The Attachments of the Fiber Bundles of the Posterior Cruciate ligament: An Anatomic Study", Arthroscopy: The Journal of Arthroscopic and Related Surgery, vol. 23, No. 3, (Mar. 2008), 284-290.
Floryan, K. et al., "Intraoperative use of Autologous Platelet-Rich and Platelet-Poor Plasma for Orthopedic Surgery Patients", AORN Journal: Home Study Program, 80(4), (Oct. 2004), 667-678.
Haynesworth, S E. et al., "Mitogenic Stimulation of Human Mesenchymal Stem Cells by Platelet Releasate Suggests a Mechanism for Enhancement of Bone Repair by Platelet Concentrate", 48th Annual Meeting of the Orthopaedic Research Society Poster No. 0462, (2002), 1 pg.
Mithoefer, Kai MD, et al., "The Microfracture Technique for the Treatment of Articular Cartilage Lesions in the Knee. A Prospective Cohort Study", The Journal of Bone and Joint Surgery 87(9), (Sep. 2005), 1911-1920.
Nixon, A J, "Platelet Enriched Plasma Provides an Intensely Anabolic Vehicle for Sustained Chondrocyte Function After Implantation", 52nd Annual Meeting of the Orthopedic Research Society: Paper No. 1416, (2005), 2 pgs.
Roseberg, MD, Thomas D. "ACL Reconstruction with Acufex Director Drill Guide and Endobutton CL Fixation System", Smith & Nephew: Knee Series, Technique Guide, (2005), 12 pgs.
Steadman, et al., "Microfracture: Surgical Technique and Rehalibitation to Treat Chondral Defects", Clinical Orthopaedics and Related Research 391, (2001), S362-S369.

(56) References Cited

OTHER PUBLICATIONS

U.S. Appl. No. 14/055,172, Non Final Office Action mailed Jul. 14, 2016, 12 pgs.
U.S. Appl. No. 14/095,614, Restriction Requirement mailed Jul. 11, 2016, 8 pgs.
U.S. Appl. No. 14/095,639, Restriction Requirement mailed Jul. 19, 2016, 8 pgs.
U.S. Appl. No. 14/182,038, Non Final Office Action mailed Jul. 19, 2016, 10 pgs.
U.S. Appl. No. 14/211,977, Notice of Allowance mailed Jul. 12, 2016, 9 pgs.
U.S. Appl. No. 14/215,550, Non Final Office Action mailed Jul. 19, 2016, 12 pgs.
European Application Serial No. 14716173.1, Response filed May 16, 2016 to Communication pursuant to Rules 161(1) and 162 EPC mailed Nov. 5, 2015, 10 pgs.
European Application Serial No. 12806211.4, Communication Pursuant to Article 94(3) EPC mailed Jun. 23, 2016, 4 pgs.
U.S. Appl. No. 13/281,009, Notice of Allowance mailed Jun. 23, 2016, 9 pgs.
U.S. Appl. No. 13/311,936, PTO Response to Rule 312 Communication mailed May 10, 2016, 2 pgs.
U.S. Appl. No. 13/645,964, Response filed Jun. 13, 2016 to Non Final Office Action mailed Mar. 15, 2016, 11 pgs.
U.S. Appl. No. 13/751,846, Notice of Allowance mailed Jul. 6, 2016, 9 pgs.
U.S. Appl. No. 13/791,014, Response filed Jun. 6, 2016 to Final Office Action mailed Jan. 8, 2016, 13 pgs.
U.S. Appl. No. 13/833,567, Advisory Action mailed Apr. 28, 2016, 3 pgs.
U.S. Appl. No. 13/833,567, Non Final Office Action mailed May 27, 2016, 9 pgs.
U.S. Appl. No. 13/838,755, Notice of Allowance mailed Apr. 27, 2016, 7 pgs.
U.S. Appl. No. 13/838,755, Response filed Apr. 15, 2016 to Final Office Action mailed Feb. 22, 2016, 11 pgs.
U.S. Appl. No. 13/959,145, Notice of Allowability mailed Jun. 14, 2016, 2 pgs.
U.S. Appl. No. 13/959,145, Notice of Allowance mailed Apr. 13, 2016, 5 pgs.
U.S. Appl. No. 14/055,172, Response filed May 4, 2016 to Restriction Requirement mailed Mar. 4, 2016, 8 pgs.
U.S. Appl. No. 14/055,191, Non Final Office Action mailed May 16, 2016, 8 pgs.
U.S. Appl. No. 14/055,191, Response filed Apr. 29, 2016 to Restriction Requirement mailed Mar. 7, 2016, 8 pgs.
U.S. Appl. No. 14/094,311, Restriction Requirement mailed Jun. 22, 2016, 6 pgs.
U.S. Appl. No. 14/159,094, Non Final Office Action mailed Jun. 29, 2016, 15 pgs.
U.S. Appl. No. 14/159,094, Response filed Jun. 3, 2016 to Restriction Requirement mailed Apr. 20, 2016, 9 pgs.
U.S. Appl. No. 14/159,094, Restriction Requirement mailed Apr. 20, 2016, 6 pgs.
U.S. Appl. No. 14/182,038, Response filed Jun. 27, 2016 to Restriction Requirement mailed Apr. 26, 2016, 8 pgs.
U.S. Appl. No. 14/182,038, Restriction Requirement mailed Apr. 26, 2016, 7 pgs.
U.S. Appl. No. 14/182,046, Response filed Jun. 27, 2016 to Restriction Requirement mailed Apr. 26, 2016, 7 pgs.
U.S. Appl. No. 14/182,046, Restriction Requirement mailed Apr. 26, 2016, 6 pgs.
U.S. Appl. No. 14/211,977, Response filed Apr. 29, 2016 to Restriction Requirement mailed Mar. 11, 2016, 8 pgs.
U.S. Appl. No. 14/215,550, Response filed Jun. 22, 2016 to Restriction Requirement mailed Apr. 28, 2016, 7 pgs.
U.S. Appl. No. 14/215,550, Restriction Requirement mailed Apr. 28, 2016, 6 pgs.
U.S. Appl. No. 14/275,548, Examiner Interview Summary mailed May 25, 2016, 3 pgs.
U.S. Appl. No. 14/275,548, Response filed May 19, 2016 to Non Final Office Action mailed Feb. 19, 2016, 19 pgs.
U.S. Appl. No. 14/324,688, Notice of Allowance mailed Jun. 9, 2016, 7 pgs.
U.S. Appl. No. 14/456,286, Advisory Action mailed Jun. 21, 2016, 3 pgs.
U.S. Appl. No. 14/456,286, Final Office Action mailed May 27, 2016, 15 pgs.
U.S. Appl. No. 14/456,286, Response filed Jun. 13, 2016 to Final Office Action mailed May 27, 2016, 10 pgs.
U.S. Appl. No. 14/589,101, Non Final Office Action mailed May 5, 2016, 14 pgs.
U.S. Appl. No. 14/697,140, Response filed Jun. 13, 2016 to Non Final Office Action mailed Apr. 8, 2016, 10 pgs.
U.S. Appl. No. 13/833,567, Response filed Apr. 20, 2016 to Final Office Action mailed Mar. 9, 2016, 10 pgs.

* cited by examiner

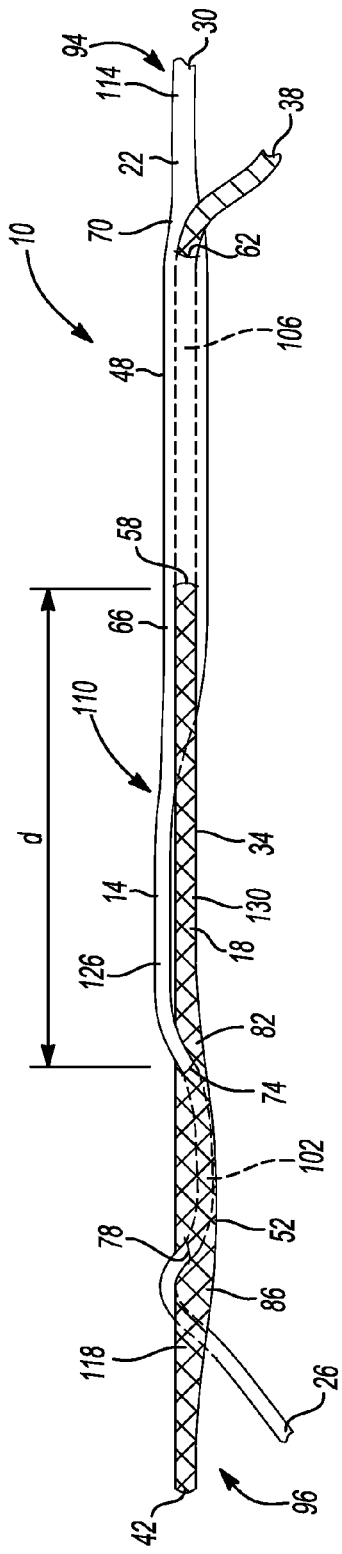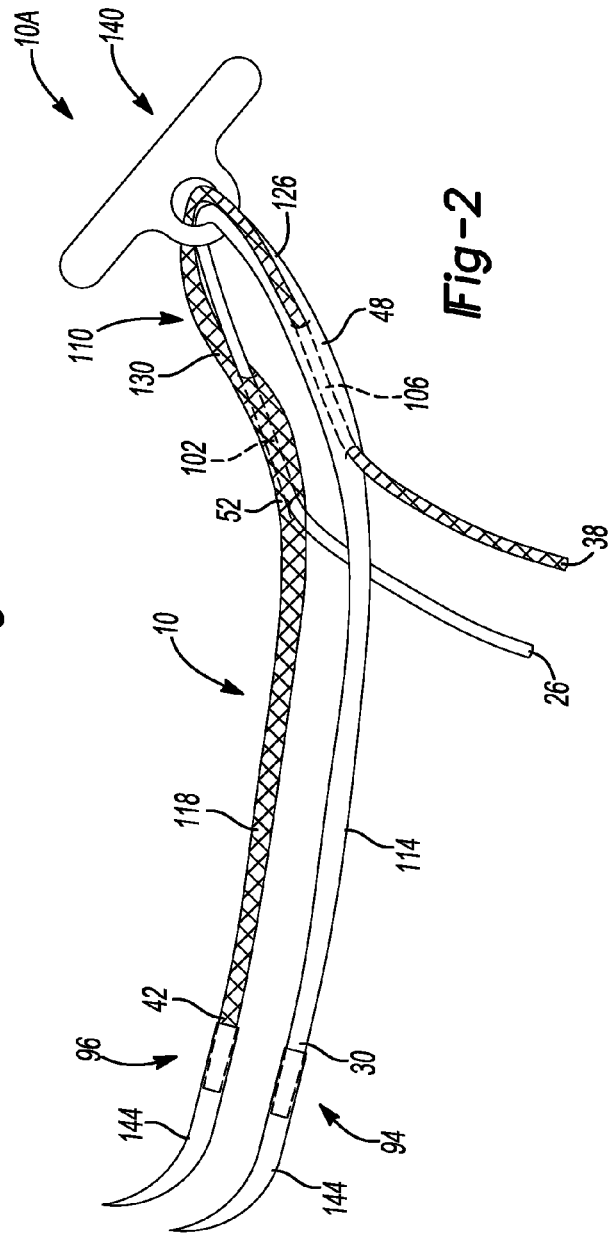

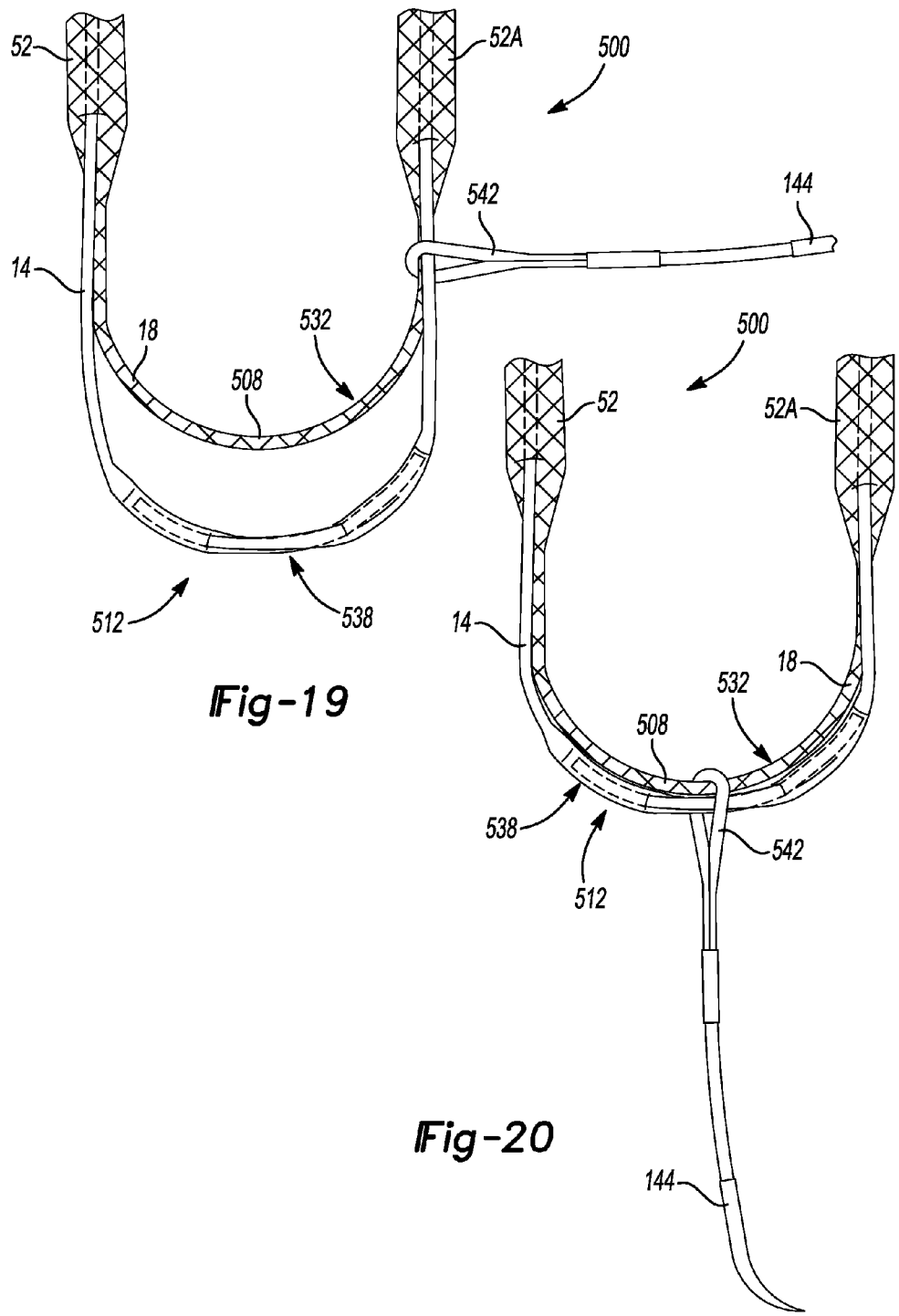

METHOD AND APPARATUS FOR FORMING A SELF-LOCKING ADJUSTABLE LOOP

CROSS-REFERENCE TO RELATED APPLICATIONS

This application is a continuation-in-part of U.S. patent application Ser. No. 13/111,564 filed on May 19, 2011, which is a continuation-in-part of U.S. patent application Ser. No. 12/938,902 filed on Nov. 3, 2010, which is a continuation-in-part of U.S. patent application Ser. No. 12/915,962 filed on Oct. 29, 2010, which is a continuation-in-part of U.S. patent application Ser. No. 12/719,337 filed on Mar. 8, 2010, which is a continuation-in-part of U.S. patent application Ser. No. 12/489,168 filed on Jun. 22, 2009, which is a continuation-in-part of U.S. patent application Ser. No. 12/474,802 filed on May 29, 2009, which is a continuation-in-part of (a) U.S. patent application Ser. No. 12/196,405 filed on Aug. 22, 2008; (b) U.S. patent application Ser. No. 12/196,407 filed on Aug. 22, 2008; (c) U.S. patent application Ser. No. 12/196,410 filed on Aug. 22, 2008; and (d) a continuation-in-part of U.S. patent application Ser. No. 11/541,506 filed on Sep. 29, 2006, which is now U.S. Pat. No. 7,601,165 issued on Oct. 13, 2009.

This application is a continuation-in-part of U.S. patent application Ser. No. 12/570,854 filed on Sep. 30, 2009, which is a continuation-in-part of U.S. patent application Ser. No. 12/014,399 filed on Jan. 15, 2008, which is now U.S. Pat. No. 7,909,851 issued on Mar. 22, 2011, which is a continuation-in-part of U.S. patent application Ser. No. 11/347,661 filed on Feb. 3, 2006, which is now U.S. Pat. No. 7,749,250 issued on Jul. 6, 2010.

This application is a continuation-in-part of U.S. patent application Ser. No. 12/702,067 filed on Feb. 8, 2010, which is a continuation of U.S. patent application Ser. No. 11/541,505 filed on Sep. 29, 2006 and is now U.S. Pat. No. 7,658,751 issued on Feb. 9, 2010.

This application is a continuation-in-part of U.S. patent application Ser. No. 13/102,182 filed on May 6, 2011, which is a divisional of U.S. patent application Ser. No. 12/196,398 filed Aug. 22, 2008, now U.S. Pat. No. 7,959,650 issued on Jun. 14, 2011, which is a continuation-in-part of U.S. patent application Ser. No. 11/784,821 filed Apr. 10, 2007.

The disclosures of all of the above applications are incorporated by reference herein.

FIELD

The present disclosure relates generally to methods and apparatus for forming a self-locking adjustable loop.

BACKGROUND

The statements in this section merely provide background information related to the present disclosure and may not constitute prior art.

Tears caused by trauma or disease in soft tissue, such as cartilage, ligament, or muscle, can be repaired by suturing. Various repair techniques and devices have been developed for facilitating suturing that include the use of an intermediate member to facilitate coupling the suture to the soft tissue and are effective for their intended purposes. Nevertheless, there is still a need in the relevant art for tissue repair techniques and associated suture constructs for facilitating suturing without requiring the use of such intermediate members.

SUMMARY

This section provides a general summary of the disclosure, and is not a comprehensive disclosure of its full scope or all of its features.

In one aspect, an apparatus for use in surgical implantation is provided in accordance with the present teachings. The apparatus can include a first flexible member and a second flexible member. The first flexible member can have a first end, a second end and a first body extending therebetween, where the first body defines a first passage portion. The second flexible member can have a first end, a second end and a second body extending therebetween, where the second body defines a second passage portion. The first end of the first flexible member can pass into and through the second passage portion in a first direction such that the first end of the first flexible member extends outside of the second passage portion. The first end of the second flexible member can pass into and through the first passage portion in a second direction such that the first end of the second flexible member extends outside of the first passage portion to form a self-locking adjustable flexible member construct. Applying tension to the first ends of the first and second flexible members can draw the first and second passage portions and corresponding second ends toward each other.

In another aspect, an apparatus for use in surgical implantation is provided in accordance with the present teachings. The apparatus can include first and second sutures. The first suture can have a first end, a second end and a first body extending therebetween, where the first body defines a first passage portion. The second suture can have a first end, a second end and a second body extending therebetween, where the second body defines a second passage portion. The first end of the first suture can pass into and through the second passage portion such that the first end of the first suture extends outside of the second passage portion, and the second end of the first suture can pass into and through the second passage portion in a direction opposite the first end of the first suture so as to form a first self-locking adjustable loop. The first end of the second suture can pass into and through the first passage portion such that the first end of the second suture extends outside of the first passage portion, and the second end of the second suture can pass into and through the first passage portion in a direction opposite the first end of the second suture to form a second self-locking adjustable loop. Applying tension to the first and second ends of the first and second sutures can reduce a size of the first and second adjustable loops.

In yet another aspect, a method of using a flexible member construct in a surgical procedure is provided in accordance with the present teachings. The method can include forming first and second bores in a bone and carrying first and second flexible anchors into the respective first and second bores, where the first and second flexible anchors can each include an internal passage slidably coupled to an adjustable suture construct. The adjustable suture construct can have first and second cooperating self-locking adjustable loops formed from first and second sutures. At least one of the first and second flexible anchors can be positioned through soft tissue. A shape of the first and second flexible anchors can be changed from a first profile to a second profile to retain the flexible anchors in the respective bores. Tension can be applied to ends of the first and second sutures of the adjustable suture construct to reduce a size of the first and second self-locking adjustable loops and secure the soft tissue relative to the first and second flexible anchors and the bone.

Further areas of applicability will become apparent from the description provided and drawings herein. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only and are not intended to limit the scope of the present disclosure.

FIG. 1 depicts an exemplary adjustable flexible member construct formed from two separate flexible member strands according to the present teachings;

FIG. 2 depicts an exemplary assembly configuration of the adjustable flexible member construct of FIG. 1 having an exemplary fixation member coupled thereto according to the present teachings;

FIGS. 18-20 depict an exemplary method of forming a portion of the adjustable flexible member construct of FIG. 15 according to the present teachings;

DETAILED DESCRIPTION

Figure 3:
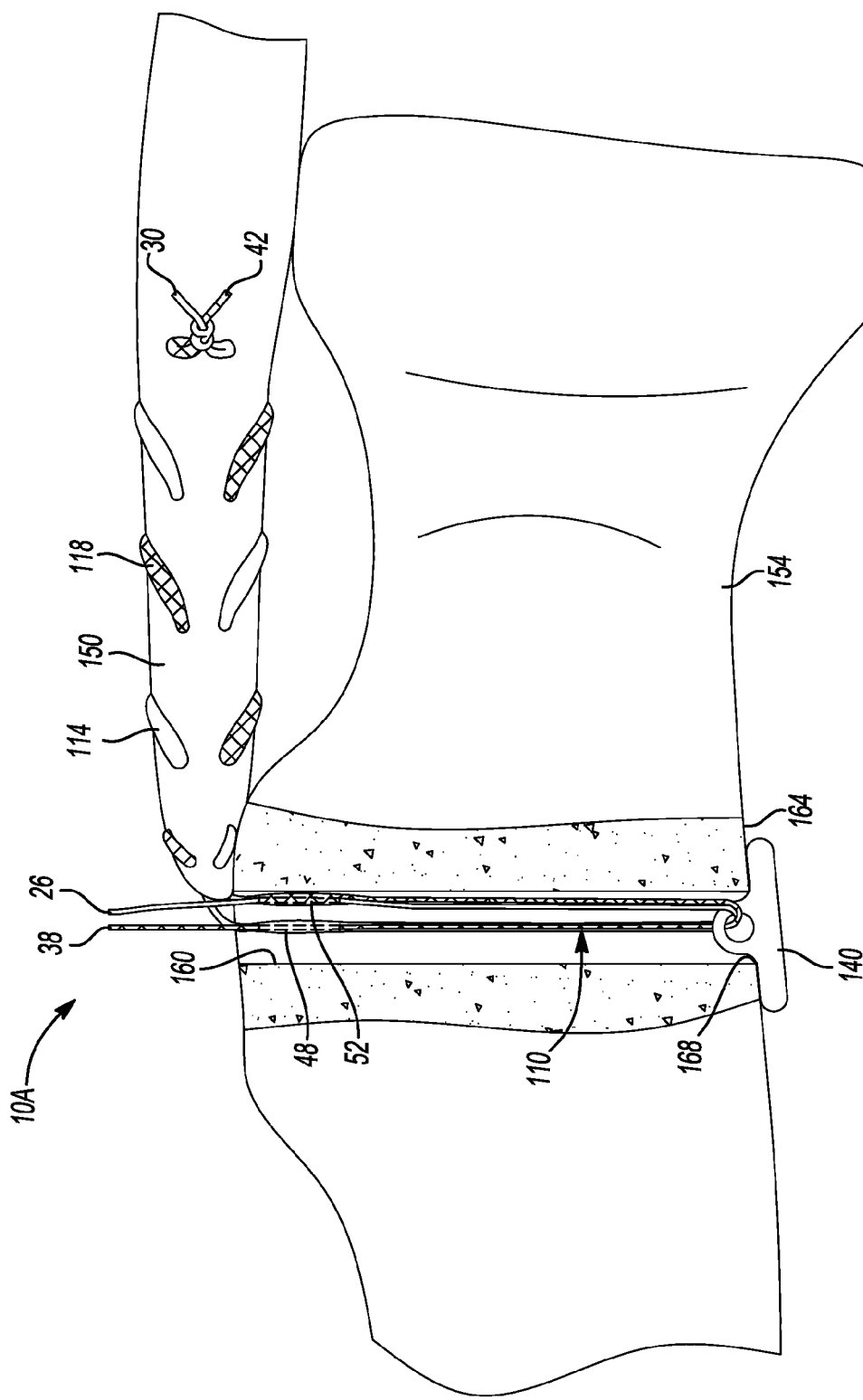
FIG. 3 depicts an exemplary technique for securing soft tissue to bone using the adjustable flexible member construct of FIGS. 1 and 2 according to the present teachings.

The following description is merely exemplary in nature and is in no way intended to limit the present disclosure, its application, or uses. It should be understood that throughout the drawings, corresponding reference numerals indicate like or corresponding parts and features. While the disclosure generally relates to apparatus and associated methods for forming self-locking adjustable loops of flexible member constructs that can be used in securing soft tissue to bone, such as a rotator cuff or distal bicep, the apparatus and methods of the present teachings can be used in connection with various other soft tissue fixation methods and/or other procedures where flexible member tensioning and securing of soft tissue is required.

Referring to FIG. 1, an adjustable flexible member construct 10 is provided according to various aspects of the present teachings. The adjustable flexible member construct 10 can be fashioned from first and second flexible members 14, 18 made of any biocompatible material including, but not limited to, non-resorbable polymers, such as polyethylene or polyester, resorbable polymers, and various combinations thereof. In various aspects, the flexible members 14, 18 can include a hollow material or core to allow for appropriate tensioning, as will be discussed herein. In various aspects, the flexible members 14, 18 can be sutures. In such aspects, the sutures can be a hollow or braided or multiple-filament braided suture structure having a hollow core. In various aspects, the sutures can be resorbable. In various aspects, the flexible members 14, 18 can define a substantially tubular hollow shape.

Flexible member 14 can include a body 22 extending between a first end 26 and a second end 30, and flexible member 18 can similarly include a body 34 extending between a first end 38 and a second end 42. The bodies 22, 34 can include respective formed first and second passage portions 48, 52, as also shown in FIGS. 1 and 2. In one exemplary aspect, the bodies 22, 34 can include an exterior surface and an interior surface defining an elongated passage between the respective first ends 26, 38 and second ends 30, 42. The bodies 22, 34 can define the passage portions 48, 52 as having a larger width than remaining portions of the bodies 22, 34. Alternatively, the passage portions 48, 52 can be formed initially to have the same width or diameter as the remaining portions of flexible member bodies 22, 34, later expanding in diameter during the construction process, which will be discussed below.

The first passage portion 48 can include first and second apertures 58, 62 positioned proximate first and second ends 66, 70 thereof. The second passage portion 52 can include third and fourth apertures 74, 78 positioned proximate third and fourth ends 82, 86 thereof, as shown in FIG. 1. In various aspects, the apertures 58, 62, 74, 78 can be formed during a braiding process of flexible members 14, 18 as loose portions between pairs of fibers defining flexible members 14, 18, or can be formed during the construction process. Alternatively, ends of the flexible members 14, 18 can be pushed between individual fibers of the braided flexible members 14, 18 as will be discussed herein. The adjustable flexible member construct 10 can include a first end 94 and a second end 96. In one exemplary configuration, the first end 94 can be defined by the second end 30 of the first flexible member 14 and the second end 96 can be defined by the second end 42 of the second flexible member 18, as shown for example in FIGS. 1 and 2.

To form the adjustable flexible member construct 10, first end 26 of flexible member 14 can be passed through second passage portion 52 via third and fourth apertures 74, 78 such that a portion 102 of flexible member 14 following first end 26 extends through passage portion 52, as generally shown in FIG. 1. In a similar manner, first end 38 of flexible member 18 can be passed through the first passage portion 48 via the first and second apertures 58, 62 such that a portion 106 of flexible member 18 following first end 38 extends through passage portion 48. This configuration can form an adjustable portion 110 of flexible member construct 10 between passage portions 48, 52, and can form fixed portions 114, 118 extending between respective passage portions 48, 52 and second ends 30, 42. In one exemplary aspect, adjustable portion 110 can include portions 126, 130 of respective flexible members 14, 18 extending between passage portions 48, 52, as shown for example in FIG. 1.

With additional reference to FIG. 2, adjustable flexible member construct 10 is shown in an assembly configuration 10A where an exemplary anchor member 140 is slidable coupled to flexible member construct 10. In the exemplary configuration illustrated, anchor member 140 is a toggle anchor configured to engage a boney structure and is coupled about the adjustable portion 110 of flexible member construct 10. The anchor member 140 can be, for example, a product sold by Biomet Sports Medicine, LLC under the name ToggleLoc™. A further discussion of the anchor member 140 can be found in U.S. Pat. No. 7,601,165. As can also be seen in FIG. 2, needles 144 or other suitable soft tissue piercing members can be coupled to second ends 30, 42 of flexible members 14, 18.

Adjustable flexible member construct 10 can provide an ability to secure the adjustable construct 10 directly to soft tissue, as well as provide an ability to reduce a size of only a portion of the adjustable construct 10 to thereby reduce an overall length of adjustable construct 10. In particular, by using the two separate flexible members 14, 18 coupled together via spaced apart passage portions 48, 52 in the manner discussed above, tension can be applied to first ends 26, 38 to reduce a length d of adjustable portion 110 relative to fixed portions 114, 118 and generally between passage portions 48, 52. In other words, tensioning first ends 26, 38 can draw the passage portions 48, 52 closer to one another thereby reducing a length of the portions 126, 130 (that form adjustable portion 110) and thus reduce the overall length of adjustable flexible member construct 10 without changing a length of fixed portions 114, 118.

Operation of the adjustable flexible member construct 10 will now be discussed in further detail with reference to an exemplary surgical technique shown in FIG. 3 where adjustable flexible member construct assembly 10A is used to attach a distal bicep tendon 150 and corresponding muscle to a radius bone 154. It should be appreciated, however, that adjustable flexible member construct 10 can be used in various attachment and/or attachment configurations, other than the example discussed above, to secure soft tissue to bone or another portion of the anatomy.

The needles 144 can be used to secure the fixed portions 114, 118 of adjustable flexible member construct 10 directly to the distal bicep tendon 150 via any suitable method, such as the whip stitch shown in FIG. 3. The construction of adjustable flexible member construct 10 provides for being able to secure the second ends 30, 42 that form the ends of the fixed portions 114, 118 directly to the soft tissue without requiring an intermediate fixation member to facilitate fixation of the adjustable construct 10 to the soft tissue. Such a configuration can reduce the complexity of the procedure as well as the apparatus used to secure the soft tissue to the bone. With the fixed portions being secured to the distal bicep tendon 150, the needles can be removed, and second ends 30, 42 can be coupled together, such as with a knot, as shown in FIG. 3.

The anchor member 140 can be passed through a bore 160 formed through the radius bone 154 and secured relative to an outer surface 164 of the radius bone 154 adjacent an opening 168 of bore 160. The first ends 26, 38 of flexible members 14, 18 that form adjustable construct 10 can then be tensioned to reduce a size of the adjustable portion 110 and draw the distal bicep tendon 150 into secure engagement with the radius bone 154, as shown in FIG. 3. As will be discussed below, the adjustable flexible member construct 10 can maintain the reduced size of the adjustable portion 110 and corresponding tension in the adjustable flexible member construct 10 without the use of a knot, as will be discussed below.

The pulling of first ends 26, 38 can cause movement of flexible member portions 126, 130 relative to passage portions 48, 52 such that the adjustable portion 110 can be reduced to a desired size and/or placed in a desired tension. Tension in flexible member portions 126, 130 and corresponding fixed portions 114, 118 can cause the bodies 22, 34 defining passage portions 48, 52 to be placed in tension and therefore constrict about flexible member portions 102, 106 passed therethrough. This constriction reduces the diameter of passage portions 48, 52, thus forming a mechanical interface between the exterior surfaces of portions 102, 106 and an interior surface of passage portions 48, 52. This constriction results in static friction between the interior and exterior surfaces at the mechanical interface, causing the adjustable flexible members 14, 18 to "automatically" lock in the reduced size or diameter configuration in which tension is maintained without requiring a knot or other additional tying technique to maintain such tension.

Figure 4:
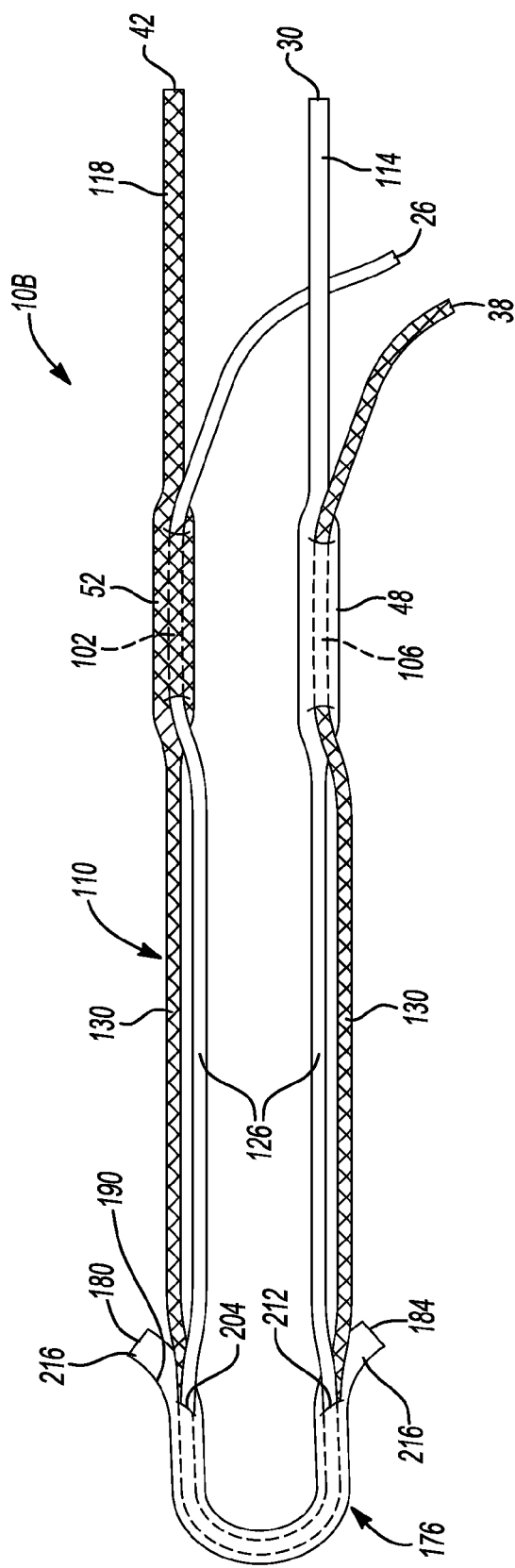
FIG. 4 depicts an exemplary assembly configuration of the adjustable flexible member construct of FIG. 1 having an exemplary flexible anchor coupled thereto according to the present teachings.
Figure 5:
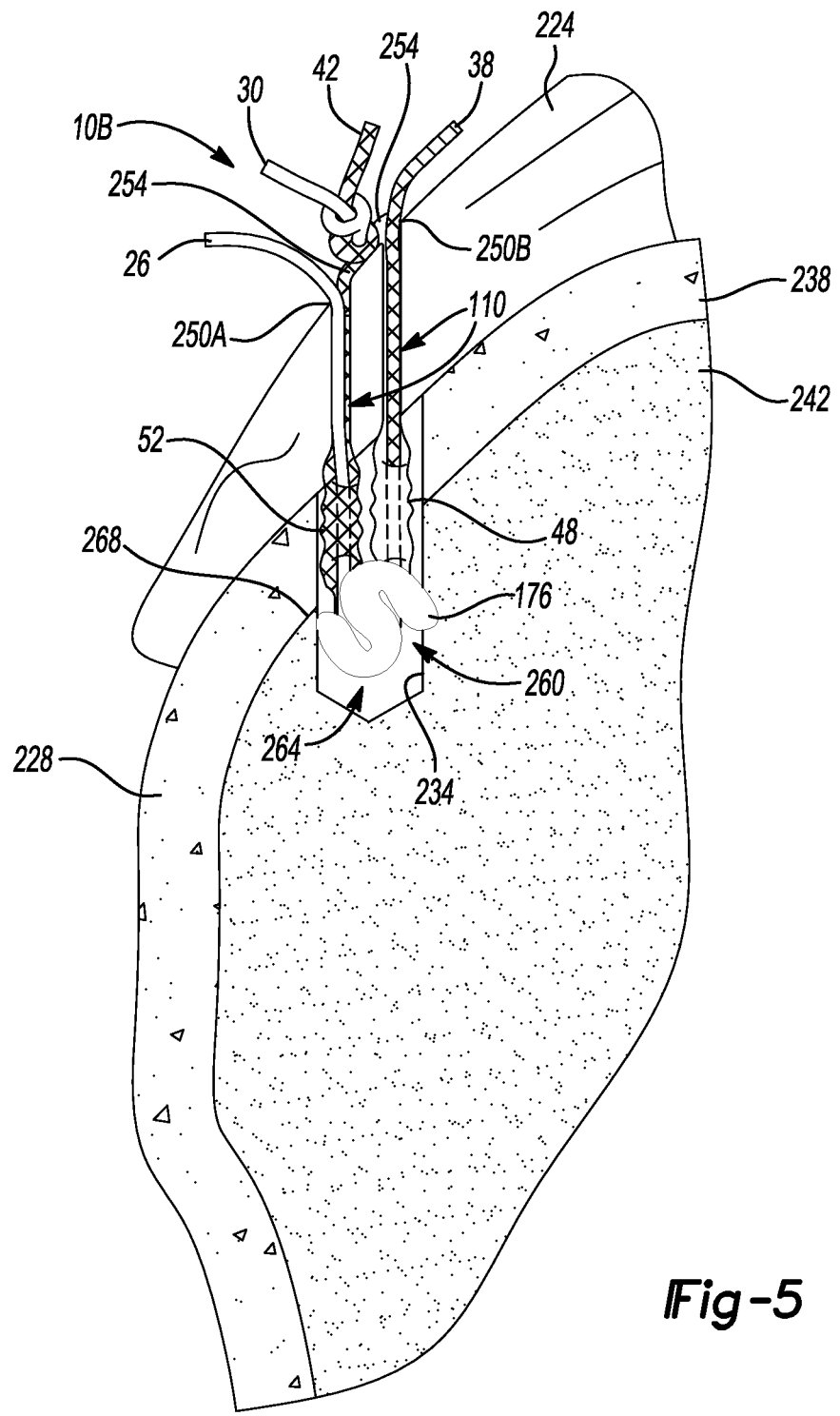
FIG. 5 depicts an exemplary technique for securing soft tissue to bone using the adjustable flexible member construct of FIG. 4 according to the present teachings.

With additional reference to FIGS. 4 and 5, adjustable flexible member construct 10 is shown in an assembly configuration 10B where a flexible anchor 176 is coupled thereto. Flexible anchor 176 can be coupled to adjustable portion 110 in a similar position to anchor member 140, as shown in FIG. 4. Flexible anchor 176 can be an elongate member having a sleeve or tubular configuration with first and second ends 180, 184 and an internal passage 190 extending therebetween. The flexible anchor 176 can be made of resorbable or non-resorbable materials, including a hollow-core braided suture, sponges and sponge-like materials in solid form, perforated materials, woven/braided from biocompatible materials or fibers, such as, for example, polymer, polyester, polyethylene, cotton, silk, or other natural or synthetic materials.

The flexible anchor 176 can have any properties that allow it to change shape. In this regard, the flexible anchor 176 can be, for example, compliant, flexible, foldable, squashable, squeezable, deformable, limp, flaccid, elastic, low-modulus, soft, spongy or perforated, or have any other characteristic property that allows it to change shape. In some aspects, the flexible anchor 176 can be coated with biological or biocompatible coatings, and also can be soaked in platelets and other biologics, which can be easily absorbed by the flexible anchor 176. In one exemplary configuration, the flexible anchor 176 can be formed from a strand of No. 5 braided polyester suture. In other words, multiple fibers can be braided together to form a hollow braided flexible member having an internal passage.

As shown for example in FIG. 4, adjustable flexible member construct 10 can be passed through a first opening 204 in a wall of the flexible anchor 176, guided into and along the internal passage 190, and passed out of the internal passage 190 through a second opening 212 in a wall of the flexible anchor 176 to associate flexible anchor 176 with adjustable portion 110. The openings 204, 212 can be positioned intermediately between the first and second ends 180, 184 of the flexible anchor 176 at a distance of, for example, one-quarter length from ends 180, 184. It will be appreciated that the openings 204, 212 can be apertures or voids in the woven fabric of the flexible anchor 176, such that the openings 204, 212 do not disrupt or break the weave of the flexible anchor 176 when made of braided or woven material. Further, portions of the flexible anchor 176 between the first and second ends 180, 184 and the corresponding first and second openings 204, 212, can define anchoring leg or tail portions 216 that can provide additional resistance for securing the flexible anchor 176 relative to a bone, fastener or implant, as will be discussed in greater detail herein.

In operation, adjustable flexible member construct assembly 10B with flexible anchor 176 can operate in a similar manner as the assembly configuration 10A with anchor member 140 discussed above. In this regard, it should be appreciated that adjustable flexible member construct assembly 10B could be used in place of adjustable flexible member construct assembly 10A to secure the distal bicep tendon 150, as well as in other soft tissue securing techniques.

For example, and with reference to FIGS. 2 and 4-5, adjustable flexible member construct assembly 10B can be used to secure a rotator cuff 224 to a humerus bone 228. In the exemplary technique depicted in FIG. 5, a bore 234 is formed in the humerus 228 through the cortical bone layer 238 and into the cancellous bone layer 242. The flexible anchor 176 can be positioned in bore 234 and the second ends 30, 42 can be passed through rotator cuff 224 via needles 144 or another suitable method at locations 250A and 250B spaced apart from each other. First end 26 can also be passed through location 250A along with second end 42 and first end 38 can be passed through second location 250B along with second end 30, as shown in FIG. 5.

The second ends 30, 42 of fixed portions 114, 118 extending through rotator cuff 224 can then be tied in a knot or secured together in another suitable manner to form a loop portion 254 over rotator cuff 224, as also shown in FIG. 5. Tension can then be applied to first ends 26, 38 to reduce a size of adjustable portion 110 and secure rotator cuff 224 to humerus 228. In applying tension to first ends 26, 38, flexible anchor 176 can be drawn into engagement with cortical bone layer 238 to set the flexible anchor 176 in an anchoring configuration or mass relative to cortical bone layer 238, as also shown in FIG. 5. In one exemplary configuration, during setting of flexible anchor 176, portions of the anchor, including tail portions 216, can bunch together, collapse, expand and/or change shape to a second shape, configuration or locking profile 260 to form an anchoring mass 264.

Anchoring mass 264 can then be set or seated against an inner face of cortical bone layer 238 surrounding bore 234. In an exemplary configuration, second shape or profile 260 can include a width that is greater than that of the initially formed bore 234 such that portions of flexible anchor 176 can expand into the cancellous bone layer 242 and extend transversely beyond the width or diameter of bore 234 beneath the cortical bone 238. For example, the anchoring mass 264 can include a width in a direction perpendicular to a longitudinal axis of bore 234 greater than the width of initially formed bore 234. In one exemplary configuration, the flexible anchor 176 can lock against a ledge 268 of cortical bone layer 238, as also shown in FIG. 5.

Upon seating of the flexible anchor 176, or in combination therewith, tension applied to first ends 26, 38 can draw loop portion 254 against rotator cuff 224 and thus draw rotator cuff 224 in secure engagement with humerus 228. As with the other techniques discussed above, adjustable flexible member construct assembly 10B can automatically lock under tension and/or load without requiring an additional knot to maintain the tension.

Figure 6:
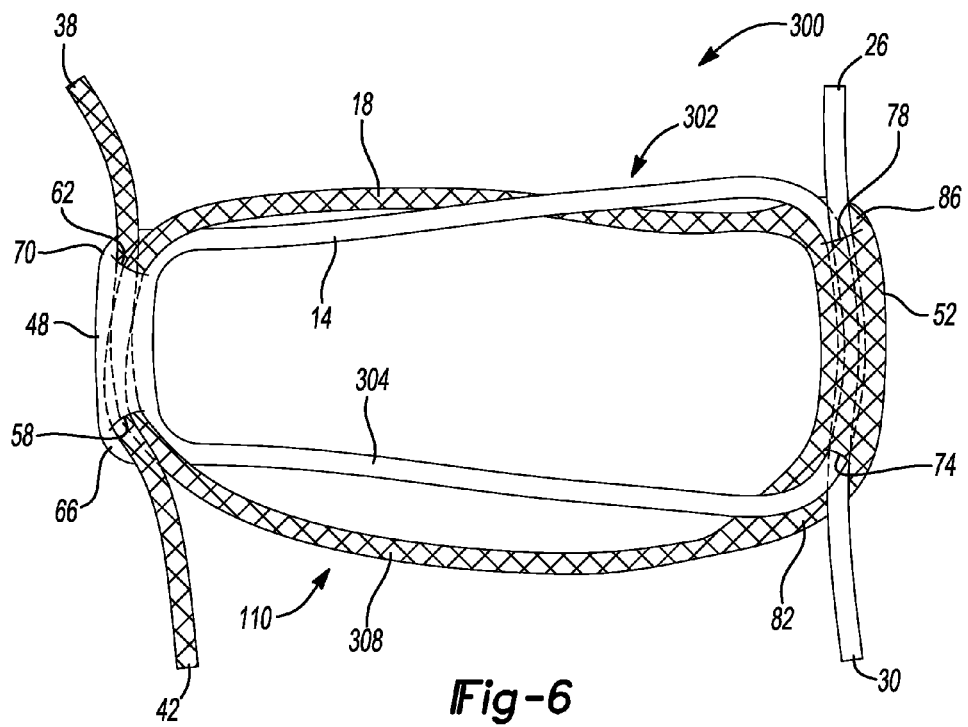
FIG. 6 depicts an exemplary adjustable flexible member construct formed from two separate flexible member strands according to the present teachings.
Figure 7:
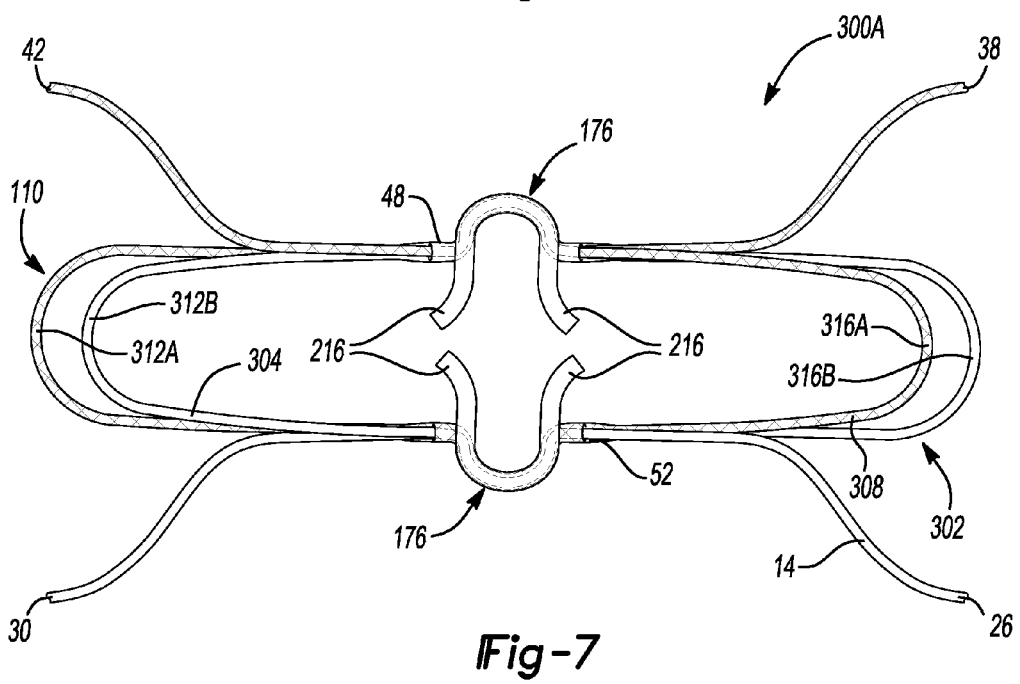
FIG. 7 depicts an exemplary assembly configuration of the adjustable flexible member construct of FIG. 6 having a pair of exemplary flexible anchors coupled thereto according to the present teachings.
Figure 8:
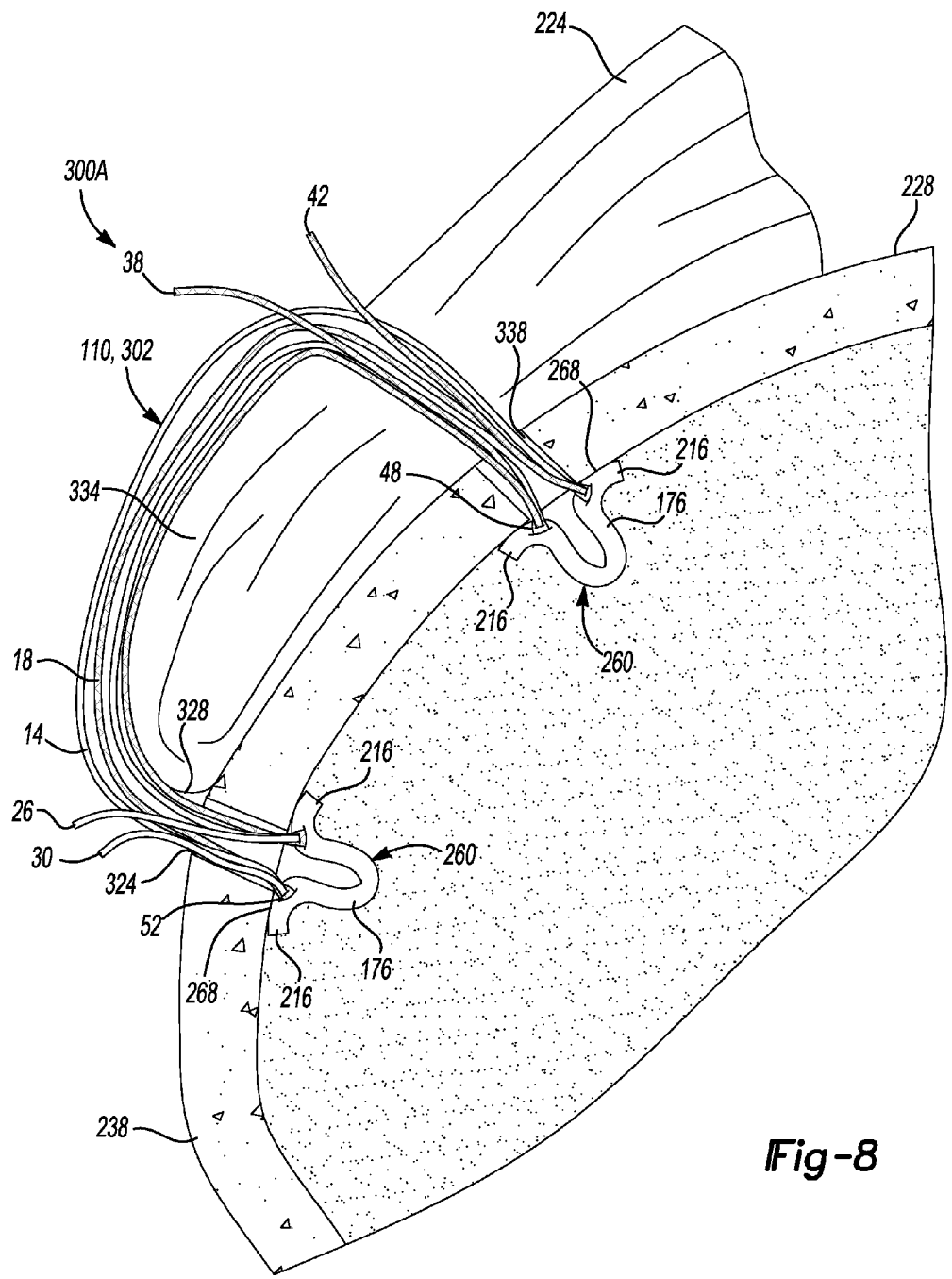
FIG. 8 depicts an exemplary technique for securing soft tissue to bone using the adjustable flexible member construct of FIGS. 6 and 7 according to the present teachings.

Turning now to FIGS. 6-8, an adjustable flexible member construct 300 is provided in accordance with the present teachings. With particular reference to FIG. 6, adjustable flexible member construct 300 can include a double loop configuration and can be optionally formed using the adjustable flexible member construct 10 discussed above. As can be seen in FIG. 6, adjustable flexible member construct 300 can include first and second ends 26, 30 of flexible member 14 extending from opposite ends of passage portion 52 of flexible member 18, and first and second ends 38, 42 of flexible member 18 extending from opposite ends of passage portion 48 of flexible member 14.

To form adjustable flexible member construct 300, second end 42 of flexible member 18 of adjustable construct 10 can be passed into passage portion 48 via second aperture 62 and out passage portion 48 via first aperture 58. Similarly, second end 30 of flexible member 14 of adjustable construct 10 can be passed into passage portion 52 via fourth aperture 78 and out passage portion 52 via third aperture 74 to form the cooperating double self-locking adjustable loop configuration shown in FIG. 6. In the exemplary configuration illustrated, the first and second ends 26, 30 of flexible member 14 pass through passage portion 52 in opposite directions and the first and second ends 38, 42 of flexible member 18 pass through passage portion 48 in opposite directions. Thus, the first and second ends 26, 30 extend from respective opposite ends 86, 82 of passage portion 52 and the first and second ends 38, 42 extend from respective opposite ends 70, 66 of passage portion 48. This configuration can thus form a first adjustable loop 304 from flexible member 14 in cooperation with passage portion 52 of flexible member 18, and a second adjustable loop 308 from flexible member 18 in cooperation with passage portion 48 of flexible member 14. In other words, two adjustable portions are formed between passage portions 48, 52, namely the adjustable portion 110 and another adjustable portion 302. In the exemplary configuration illustrated, when adjustable flexible member construct 300 is placed under tension, the first adjustable loop 304 can self-lock in cooperation with passage portion 52 and the second adjustable loop 308 can self-lock in cooperation with passage portion 48. In one exemplary aspect, the first and second adjustable loops 304, 308 can be co-locking adjustable loops of self-locking adjustable flexible member construct 300.

FIG. 7 illustrates adjustable flexible member construct 300 in an assembly configuration 300A where a pair of flexible anchors 176 are coupled to the respective passage portions 48, 52. It should be appreciated, however, that the pair of flexible anchors 176 could alternatively be different fixation members and/or could be coupled to first portions 312A, 312B of both the first and second loops 304, 308 and second portions 316A, 316B of both the loops 304, 308 of adjustable flexible member construct 300.

The longitudinal and parallel placement of the first and second ends 26, 30 of flexible member 14 within and through passage portion 52 and the first and second ends 38, 42 of flexible member 18 within and through passage portion 48 resists the reverse relative movement of the first and second ends of each of flexible members 14, 18 once flexible member construct 300/300A is tightened. Upon applying tension to the first and second ends 26, 30 and the first and second ends 38, 42, adjustable portions 110, 302 can be reduced to a desired size or placed in a desired tension. Tension in the adjustable portions 110, 302 can cause the bodies of the flexible members 14, 18 defining the passage portions 48, 52 to be placed in tension and therefore constrict about the portions of flexible members 14, 18 extending therethrough similarly to the constriction discussed above with respect to adjustable flexible member construct 10. This constriction can cause the adjustable flexible member construct 300/300A to "automatically" lock in a reduced size or smaller diameter configuration and maintain the tension without requiring a knot.

With particular reference to FIG. 8, an exemplary technique for coupling soft tissue to bone with adjustable flexible member construct assembly 300A will now be discussed in accordance with the present teachings. In one exemplary aspect, adjustable flexible member construct assembly 300A can be used to secure the rotator cuff 224 to the humerus 228. In this aspect, the flexible anchor 176 coupled to passage portion 52 can be positioned in a first bore 324 formed in the humerus 228 in a similar manner as bore 234 discussed above. In the exemplary aspect illustrated, first bore 324 can be formed in humerus 228 adjacent an end 328 of rotator cuff 224, as shown in FIG. 8. The adjustable construct assembly 300A can then be positioned over a portion 334 of the rotator cuff 224 and pierced through rotator cuff 224 such that the flexible anchor 176 coupled to the second passage portion 48 is positioned within a second bore 338 spaced apart from the first bore 324. At this point, the adjustable portions 110, 302 can extend from each of the passage portions 48, 52 over the rotator cuff 224, as shown in FIG. 8.

Tension can then be applied to the first and second ends 26, 30 of flexible member 14 and the first and second ends 38, 42 of flexible member 18 to reduce a size of the adjustable portions 110, 302 and draw the rotator cuff 224 into secure engagement with the humerus 228. As discussed above, tensioning the first and second ends 26, 30, 38, 42 places the adjustable portions 110, 302 under tension thereby causing the passage portions 48, 52 to constrict and automatically lock the flexible members 14, 18 in place under the desired tension without the use of a knot. Further, tensioning the free ends 26, 30, 38, 42 can draw flexible anchors 176 in bores 324, 338 against the cortical bone layer 238 such that tail portions 216 engage the ledge 268 of cortical bone layer 238 thus changing a shape of the flexible anchors 176 from a first profile when the flexible anchors 176 are inserted into the bores 324, 338 to the second profile 260 shown in FIG. 8 where tail portions engage the ledge 268 of cortical bone layer 238. In one exemplary configuration, flexible anchors 176 can change from the first shape or profile to the second shape or profile 260 forming anchoring mass 264 against ledge 268, as shown in FIG. 8 with reference to FIG. 5.

It should be appreciated that while the rotator cuff technique has been discussed above in connection with placing passage portion 48 in bore 338 and passage portion 52 in bore 324, either passage portion 48, 52 could be placed in either bore 324, 338. Further, flexible anchors 176 coupled to first portions 312A, 312B and second portions 316A, 316B could alternatively be positioned in the bores 324, 338. In addition, more than one adjustable flexible member construct assembly 300A could be utilized to secure the rotator cuff 224 to humerus 228 using the same or additional bores formed in humerus 228.

Figure 9:
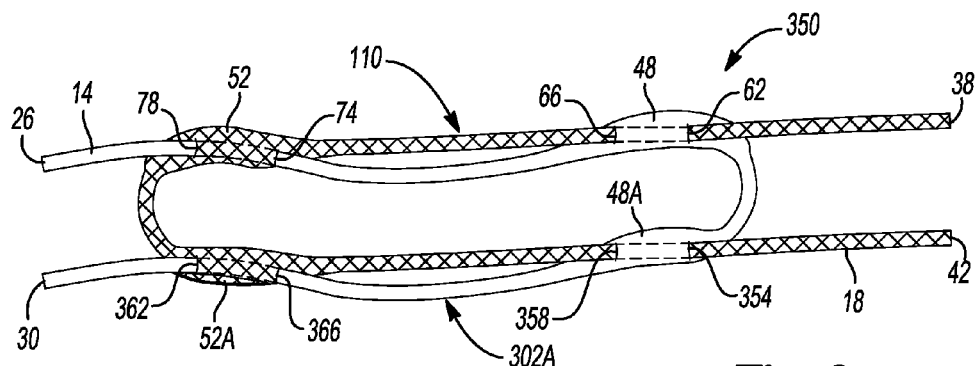
FIG. 9 depicts an exemplary adjustable flexible member construct formed from two separate flexible member strands according to the present teachings.

Turning now to FIG. 9, an adjustable flexible member construct 350 is provided according to the present teachings.

The adjustable flexible member construct 350 can include a double loop configuration as well as two passage portions 48, 48A defined by flexible member 14 and two passage portions 52, 52A defined by flexible member 18. Adjustable flexible member construct 350 can also be formed based on the adjustable flexible member construct 10 discussed above. In this regard, flexible member 14 can include the second passage portion 48A and flexible member 18 can include the second passage portion 52A. In the exemplary configuration illustrated, each of the second passage portions 48A, 52A are spaced apart from the corresponding first passage portions 48, 52. Passage portion 48A can include a fifth aperture 354 and a sixth aperture 358, and passage portion 52A can include a seventh aperture 362 and an eighth aperture 366.

Using adjustable flexible member construct 10 with the second passage portions 48A, 52A discussed above, second end 30 of flexible member 14 can be passed into passage portion 52A via aperture 366 and out via aperture 362, as shown in FIG. 9. Similarly, second end 42 of flexible member 18 can be passed into passage portion 48A via aperture 358 and out via aperture 354. This construction can provide a double loop configuration similar to construct 300, but with four passage portions. In this regard, adjustable portion 110 can remain between passage portions 48 and 52, as shown in FIG. 9. However, adjustable portion 302, depicted in FIG. 9 as 302A, can be positioned between second passage portions 48A and 52A. Adjustable flexible member construct 350 can automatically lock when placed under tension similar to the constructs discussed above, and can also be provided in various assembly configurations, such as with flexible anchors 176. In this regard, construct 350 can be used to secure soft tissue to bone, such as in the exemplary rotator cuff technique discussed above, as well as to compress two bone portions together, such as discussed in commonly owned, co-pending U.S. Pub. Nos. 2010/0211075 and 2011/0106153, the disclosures of which are incorporated by reference herein.

Figure 12:
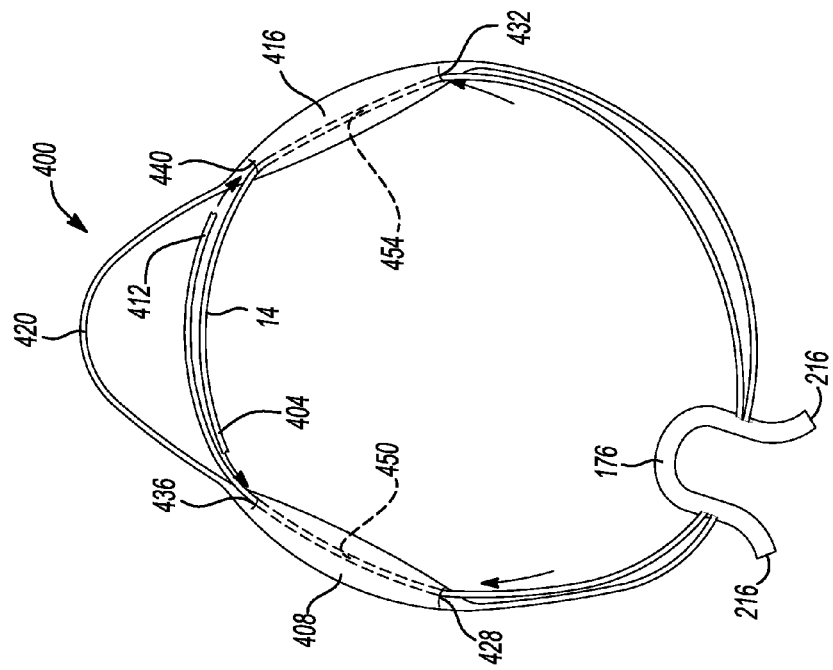
Figure 13:
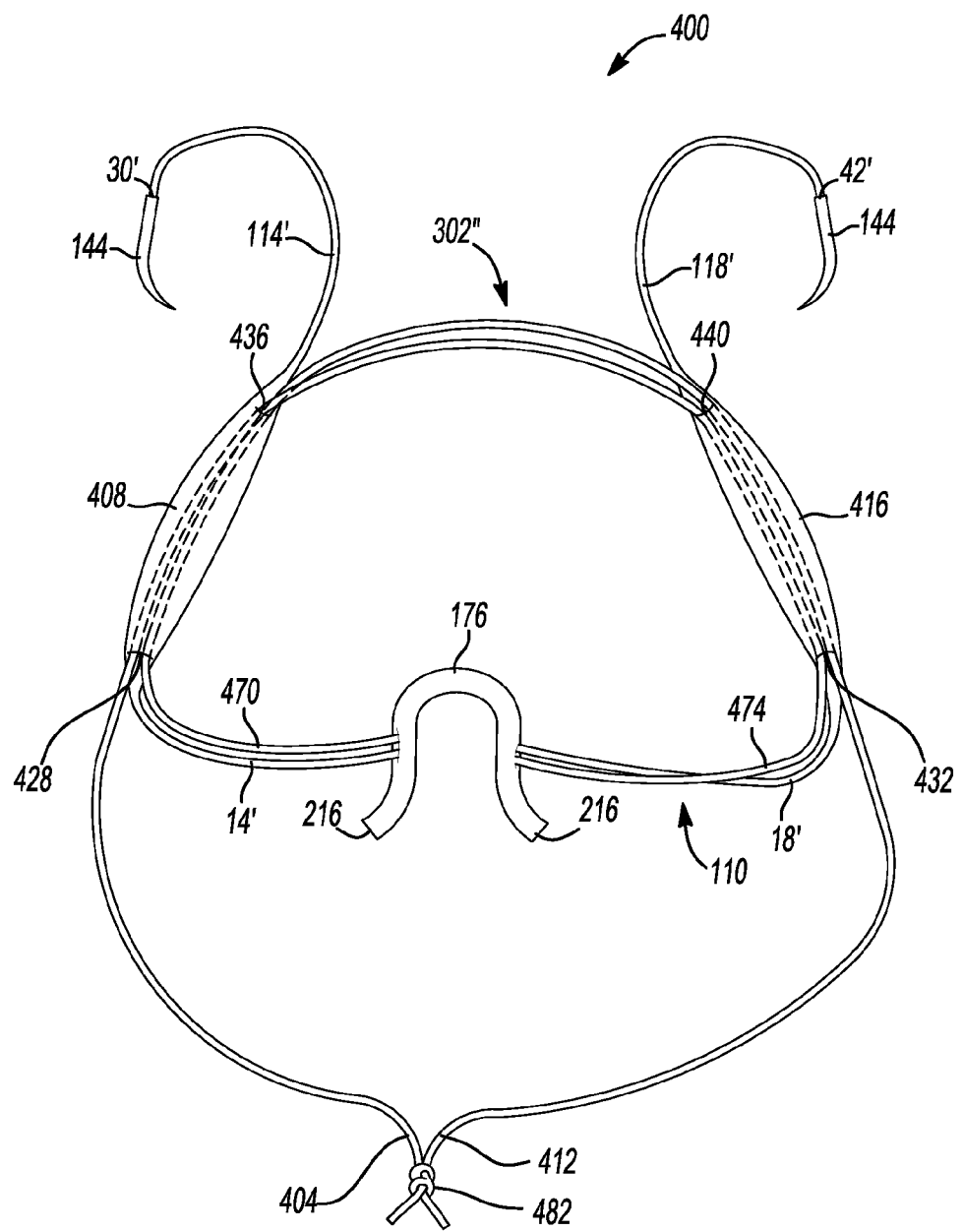
Figure 14:
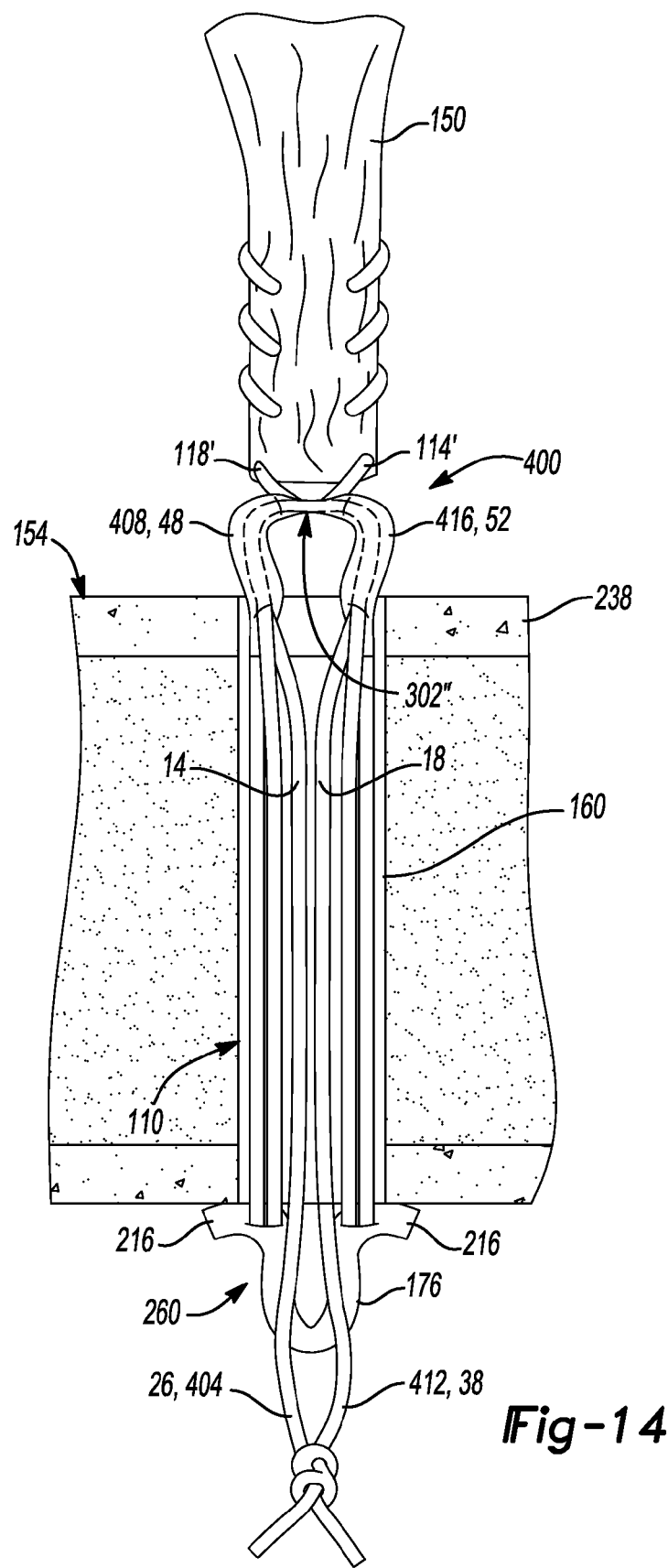
FIG. 14 depicts an exemplary technique for securing soft tissue to bone using the adjustable flexible member construct of FIG. 13 according to the present teachings.

With additional reference to FIGS. 10-14, an adjustable flexible member construct 400 is provided in accordance with the present teachings. FIGS. 10-13 illustrate an exemplary method of forming construct 400 and FIG. 14 illustrates an exemplary technique of securing soft tissue to bone using construct 400. The adjustable flexible member construct 400 can be fashioned from either a single flexible member, such as flexible member 14, or from two flexible members, such as by using adjustable flexible member construct 10 as a starting point.

Figure 10:
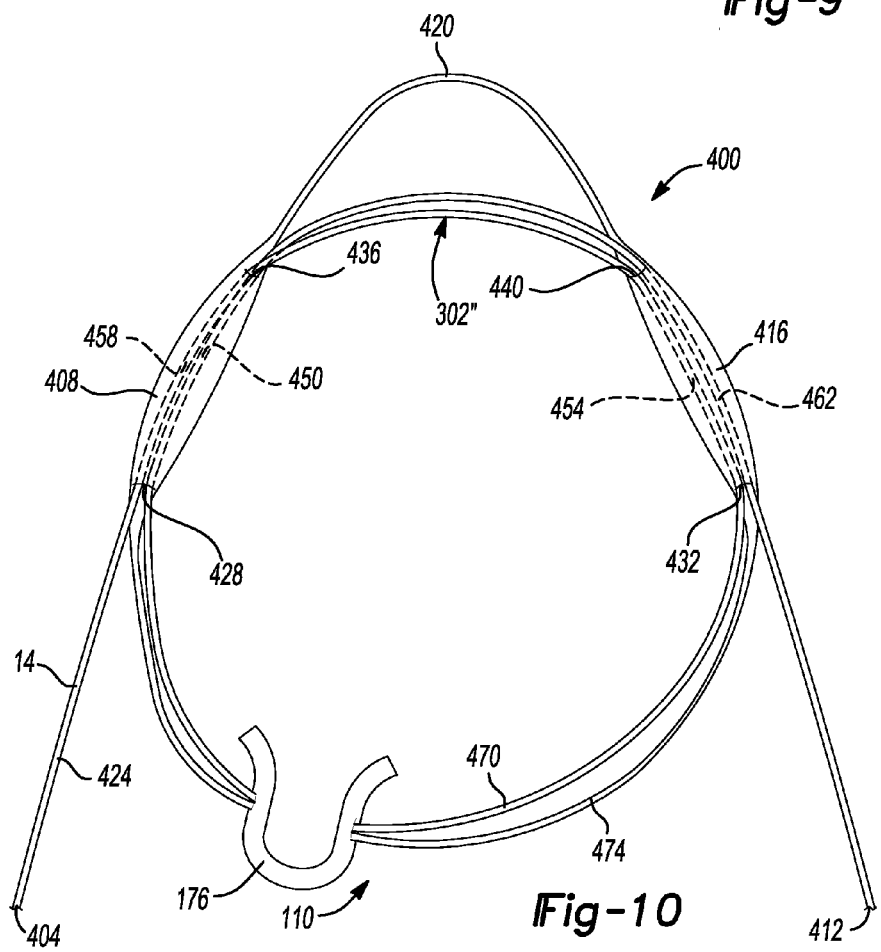
FIGS. 10-13 depict an exemplary adjustable flexible member construct and an exemplary technique for forming the same according to the present teachings.

Forming adjustable flexible member construct 400 from a single flexible member, such as flexible member 14, will now be discussed with particular reference to FIGS. 10-13. In this aspect, the adjustable flexible member construct 400 can include a first end 404, a first formed passage portion 408, a second end 412, a second formed passage portion 416, and a fixed length loop portion 420 (when formed from a single flexible member) connecting the first and second passage portions 408, 416, as shown in FIG. 10. In the exemplary configuration illustrated, flexible member construct 400 can include an elongated body 424 having an exterior surface and an interior surface defining an elongated passage between the first and second ends 404, 412. The body 424 can define the first and second passage portions 408, 416 and the fixed length portion 420 therebetween. Passage portions 408, 416 can each include first apertures 428, 432 positioned proximate one end thereof, and second apertures 436, 440 positioned proximate a second opposite end thereof. The passage portions 408, 416 can be formed to have a larger width or diameter than remaining portions of flexible member 14, as also shown in FIG. 10. Alternatively, the passage portions 408, 416 can be formed initially to have the same width or diameter as the remaining portions of flexible member 14, later expanding in diameter during the construction process. In various aspects, the first and second apertures 428, 432, 436, 440 can be formed during a braiding process of flexible member 14 as loose portions between pairs of fibers defining flexible member 14, or can be formed during the construction process. Alternatively, the first and second ends can be pushed between individual fibers of the braided flexible member 14.

Figure 11:
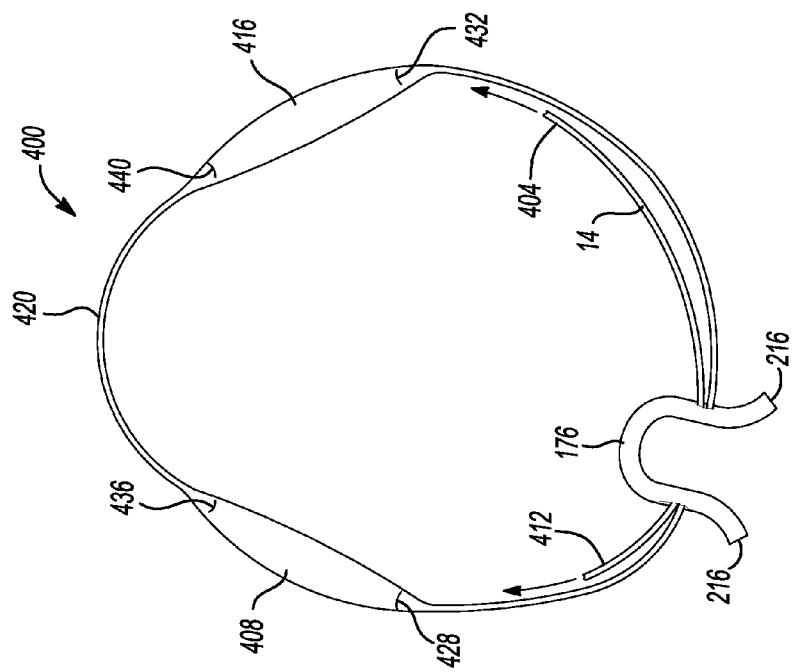

The first end 404 can be passed through second passage portion 416 via first and second apertures 432, 440, as generally shown in FIGS. 11 and 12. In a similar manner, second end 412 can be passed through the first passage portion 408 via the first and second apertures 428, 436, as also shown in FIGS. 11 and 12. Subsequently, as shown in FIG. 12 with reference to FIG. 10, first end 404 can be passed through the first passage portion 408 via second and first apertures 436, 428, respectively. First end 404 can follow a path that is opposite in direction to a path followed by a portion 450 of the flexible member 14 that has already passed through first passage portion 408 while following second end 412 through first and second apertures 428, 436.

Similarly, second end 412 can be passed through the second passage portion 416 via second and first apertures 440, 432, respectively. Second end 412 can follow a path that is opposite in direction to a path followed by a portion 454 of the flexible member 14 that has already passed through second passage portion 416 while following first end 404 through first and second apertures 432, 440. This results in portions 458, 462 of flexible member 14 being positioned parallel or substantially parallel to portions 450, 454 in passage portions 408, 416. Passing the first and second ends 404, 412 through passage portions 408, 416 as discussed above forms adjustable loops 470, 474, as shown in FIG. 10. The first and second ends 404, 412 can be passed through the same apertures in each passage portion 408, 416 or, alternatively, through separate apertures in each passage portion 408, 416.

The fixed portion 420 can then be cut, as shown in FIG. 13, to effectively form two flexible members 14' and 18' having fixed length portions 114', 118' with ends 30' and 42'. Needles 144 or other flexible member passing instruments can be coupled to ends 30', 42' and a flexible anchor 176 can be coupled to loops 470, 474 to form the construct 400, as illustrated in FIG. 13. Ends 404, 412 can also be tied in an optional knot 482.

The adjustable flexible member construct 400 can thus provide a double adjustable loop configuration via loops 470, 474 while also providing fixed portions 114', 118' extending from passage portions 408, 416. As will be discussed in greater detail herein, this configuration can be used, for example, to couple soft anchor 176 to loops 470, 474 and couple fixed length portions 114', 118' directly to soft tissue.

In another exemplary aspect, adjustable flexible member construct 400 can be formed starting with two separate flexible members, such as flexible members 14, 18. For example, and with reference to FIG. 13 and adjustable flexible member construct assembly 10A discussed above in FIG. 4, first end 26 of flexible member 14 can be passed into passage portion 48 via second aperture 62 and out via first aperture 58 thereby passing through passage portion 48 in an opposite direction as flexible member 18. In a similar manner, first end 38 of flexible member 18 can be passed into passage portion 52 via fourth aperture 78 and out via third aperture 74 thereby passing through passage portion 52 in an opposite direction as flexible member 14. This technique can thus also be used to form adjustable flexible member construct 400 having fixed length portions 114', 118' and two adjustable loops 470, 474 formed by adjustable portions 110 and 302" extending between passage portions 408, 416.

With particular reference to FIGS. 13 and 14, operation of adjustable flexible member construct 400 will now be discussed in greater detail in connection with an exemplary technique where construct 400 is used to attach soft tissue to bone. In one exemplary aspect, fixed portions 114', 118' can be coupled to soft tissue, such as the distal bicep tendon 150, using needles 144. In one exemplary configuration, fixed portions can be 114', 118' can be directly sutured to the soft issue, such as via the whip stitch shown in FIG. 14, and then the remaining fixed portions 114', 118' and needle 144 can be removed. The ends 404, 412 can be optionally tied together and passed through the bore 160 formed in the radius bone 154 along with the a portion of the loops 470, 474 such that flexible anchor 176 is positioned through bore 160.

Tension can then be applied to ends 404, 412 to reduce a size of loops 470, 474 and/or adjustment portions 110, 302" and draw the distal bicep tendon 150 toward radius bone 154 and into secure engagement therewith. Tensioning ends 404, 412 can place the bicep tendon 150 and associated muscle, as well as the flexible members 14', 18' of the adjustable construct 400 under a desired tension. Similar to the constructs discussed above, tension in flexible members 14, 18 can cause the passage portions 408, 416 to constrict and thereby automatically lock the adjustment portions 110, 302" to maintain the desired tension without the use of a knot.

With additional reference to FIGS. 15-29, an adjustable flexible member construct 500 and associated exemplary surgical technique will now be discussed in accordance with various aspects of the present teachings. As will be discussed in greater detail below, adjustable flexible member construct 500 can be formed from two separate flexible members and can facilitate coupling a fixed portion of the construct directly to soft tissue without requiring an intermediate coupling member.

Figure 15:
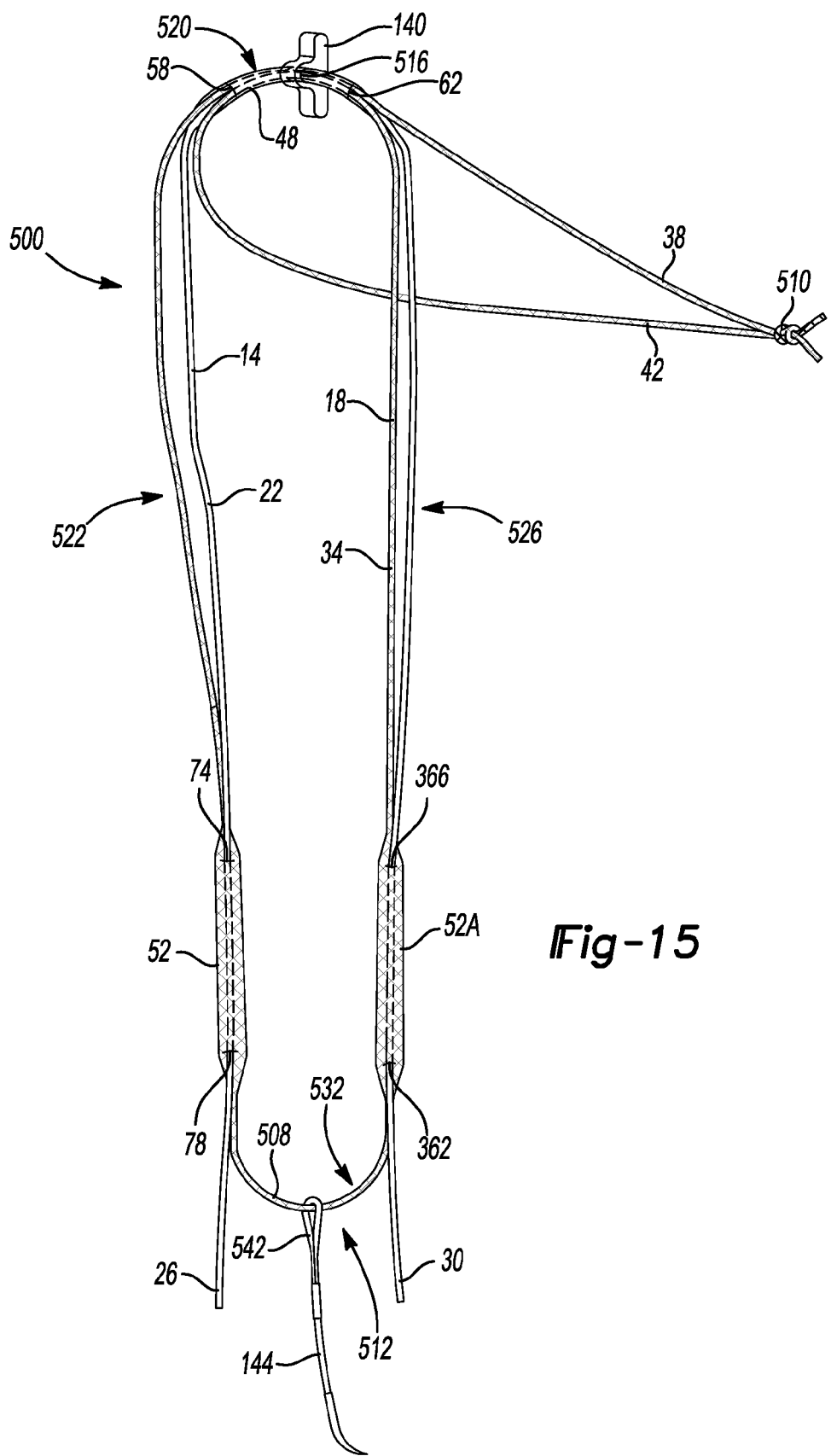
FIG. 15 depicts an exemplary adjustable flexible member construct according to the present teachings.
Figure 16:
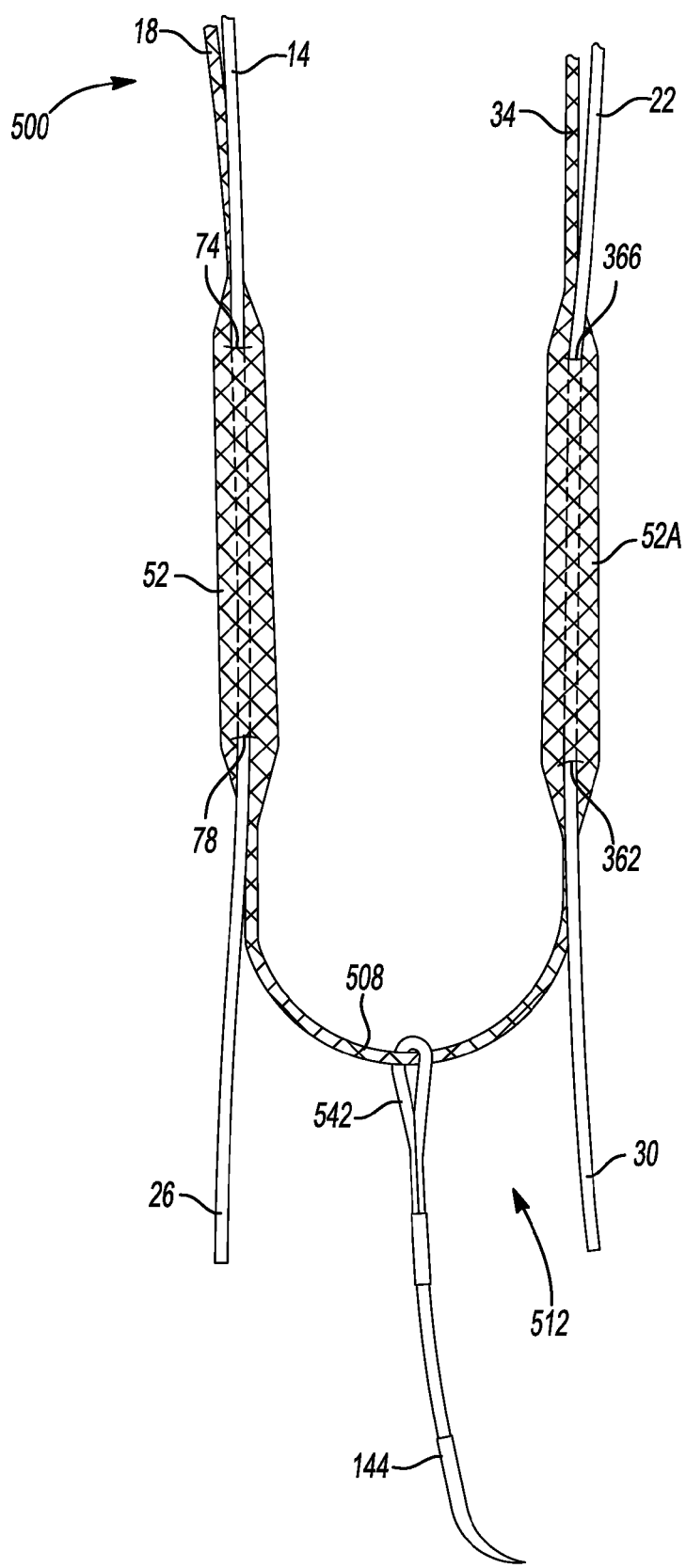
FIGS. 16-17 depict enlarged views of portions of the adjustable flexible member construct of FIG. 15 according to the present teachings.

The adjustable flexible member construct 500 can be fashioned from the first and second flexible members 14, 18 and, as will become apparent from the discussion below, can include features similar to aspects of adjustable flexible member construct 300 shown in FIG. 6 and adjustable flexible member construct 350 shown in FIG. 9. In this configuration, the body 22 of first flexible member 14 can define one passage portion 48 having first and second apertures 58, 62, as generally shown in FIG. 15 and the enlarged view of FIG. 17. Such a configuration of flexible member 14 is also shown in FIG. 6, with particular reference to a left hand side of construct 300. The body 34 of flexible member 18 can define two passage portions 52, 52A having respective apertures 74, 78 and 362, 366, as generally shown in FIG. 15 with reference to the enlarged view of FIG. 16. As can be seen, passage portions 52, 52A can be spaced apart from each other by a fixed portion 508 of flexible member 18. Such a configuration of flexible member 18 is also shown in FIG. 9, with particular reference to a left hand side of construct 350.

To form adjustable flexible member construct 500, the first end 26 of flexible member 14 can be passed into and through passage portion 52 via apertures 74, 78 and second end 30 can be passed into and through passage portion 52A via apertures 366, 362. The first end 38 of flexible member 18 can be passed into and through passage portion 48 via apertures 58, 62, and the second end 42 can be passed through passage portion 48 in an opposite direction as first end 38 via apertures 62, 58. It should be appreciated that first and second ends 38, 42 can be passed through passage portion 48 via the same or different apertures.

Figure 17:
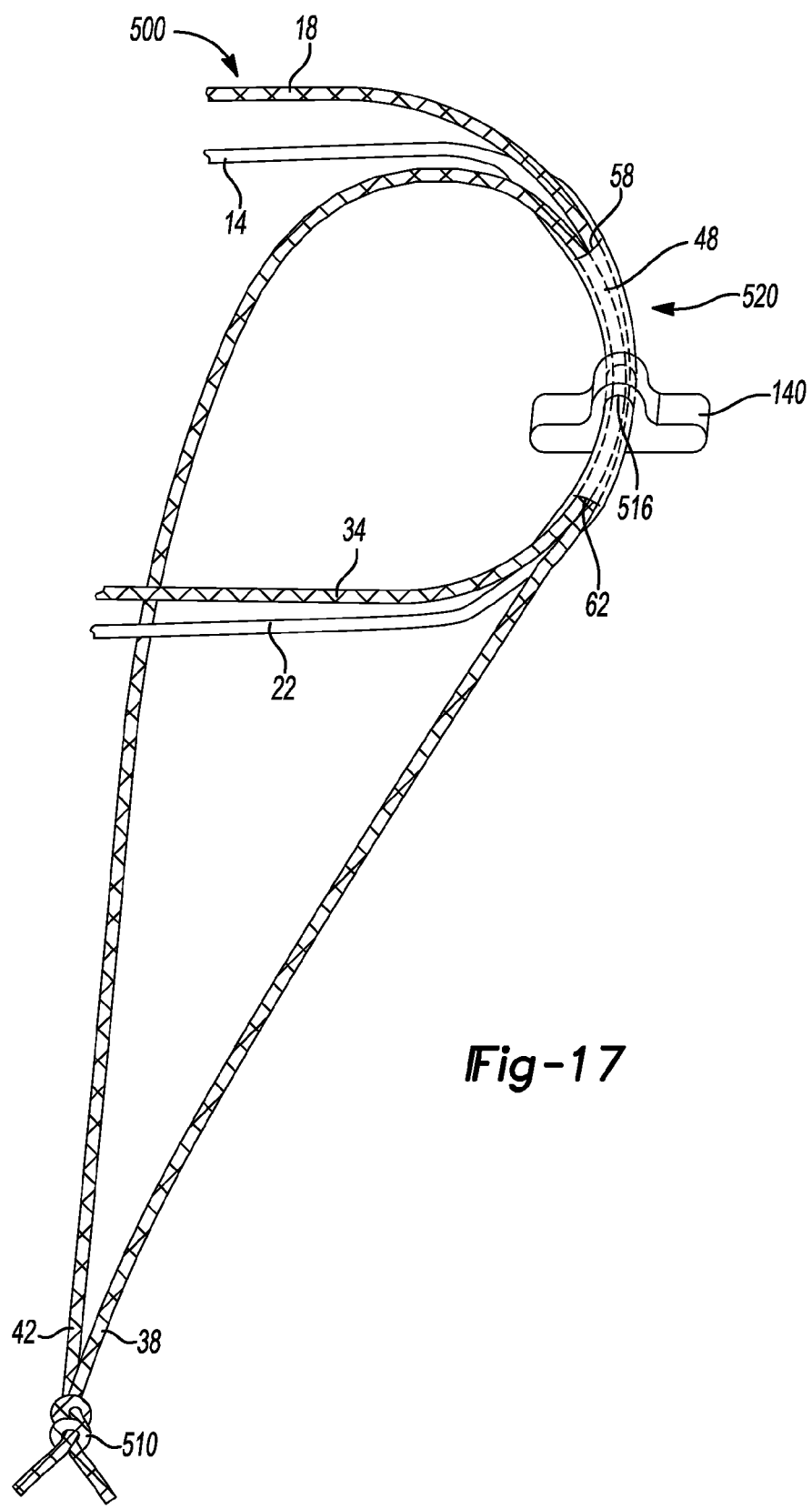

First and second ends 38, 42 can then optionally be tied in a knot 510 or otherwise coupled together, as shown in FIG. 15. In the exemplary configuration illustrated in FIGS. 15-29, adjustable flexible member construct 500 can include needle 144 slidably coupled to the fixed portion 508 at a first end 512 of construct 500, and anchor member 140 coupled to passage portion 48 via aperture 516 at a second opposite end 520 of construct 500. In this exemplary configuration, passage portion 48, as well as first and second ends 38, 42 of flexible member 18 extending therethrough are slidably positioned through aperture 516 of anchor member 140, as shown in FIG. 17. While adjustable flexible member construct 500 is shown and discussed in connection with needle 144 and anchor member 140, it should be appreciated that construct 500 can be used with or without needle 144 and anchor member 140 and/or with other suitable suture passing members and/or fixation members, such as flexible anchor 176.

This configuration of adjustable flexible member construct 500 can form first and second adjustment portions 522, 526 extending between passage portions 52, 52A of flexible member 18 and passage portion 48 of flexible member 14, as shown in FIG. 15. Further, the looped configuration of flexible member 18 in cooperation with passage portions 48, 52, 52A can also provide an adjustable loop 532. As will be discussed in greater detail below, tension can be applied to ends 26, 30 of flexible member 14 and ends 38, 42 of flexible member 18 to reduce a size of loop 532 and adjustment portions 522, 526. In this regard, adjustable flexible member construct 500 can be used to attach soft tissue to bone and automatically lock the suture construct 500 via passage portions 48, 52 and 52A at a desired size or tensile load without the use of a knot.

Figure 18:
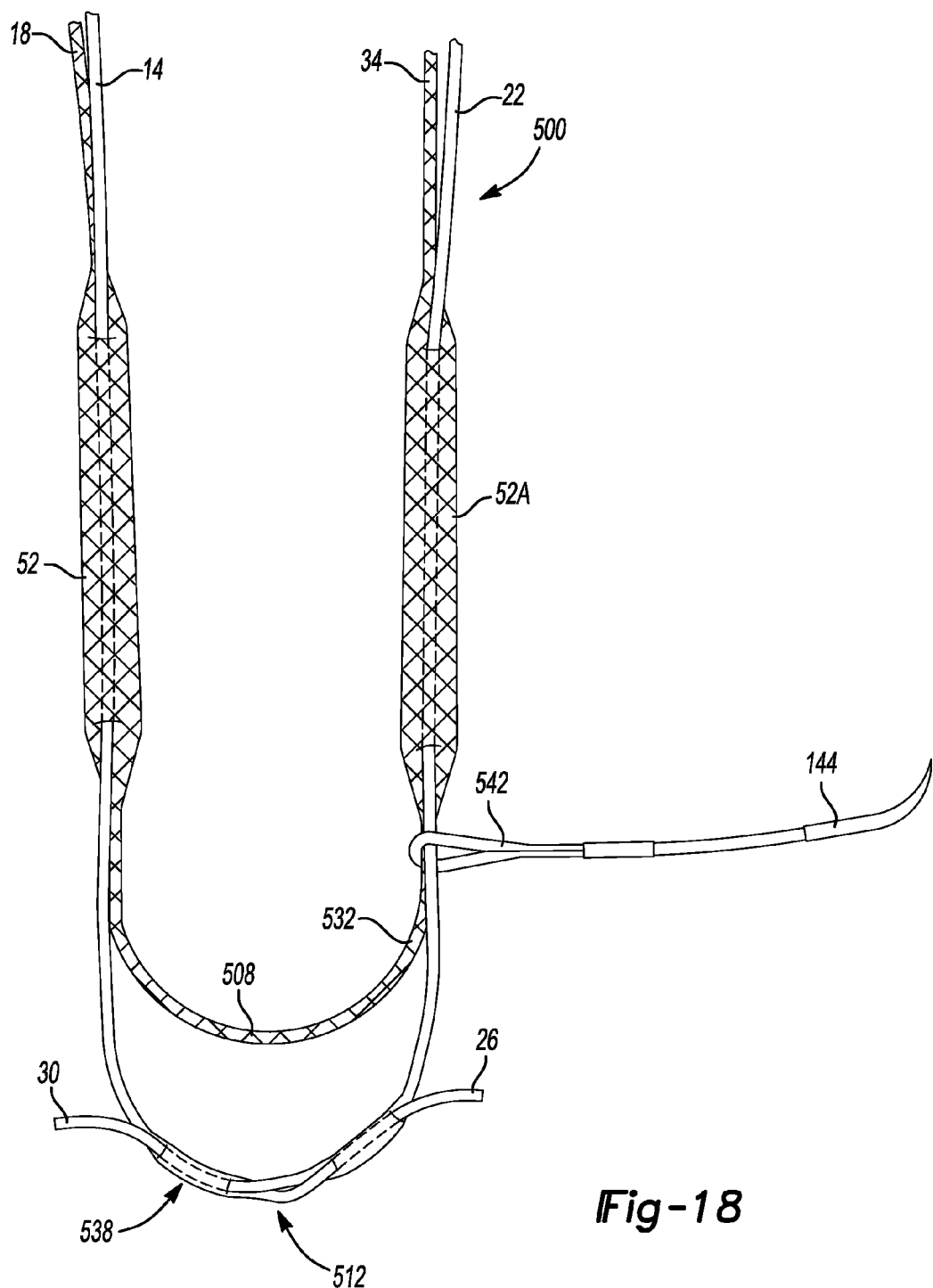

To facilitate coupling the first end 512 of adjustable flexible member construct 500 to soft tissue, free ends 26, 30 at the first end 512 can be optionally passed or tucked inside body 22 and can form a loop portion 538, as shown in FIG. 18. Any remaining portions of ends 26, 30 extending from body 22 can then be trimmed, as shown in FIG. 19. Before tucking the free ends 26, 30 into body 22, one of the free end 26 or 30 can be passed inside the coupling loop 542 such that needle 144 can then be passed around both fixed portion 508 and formed loop portion 538, as also shown in FIG. 19. A size of loop 532 can be optionally adjusted relative to passage portion 48 to substantially align fixed portion 508 with formed loop portion 538, as shown in FIG. 20. Having the fixed portion 508 align with formed loop portion 538 can facilitate easier passing of construct 500 through soft tissue, as will be discussed below.

Figure 21:
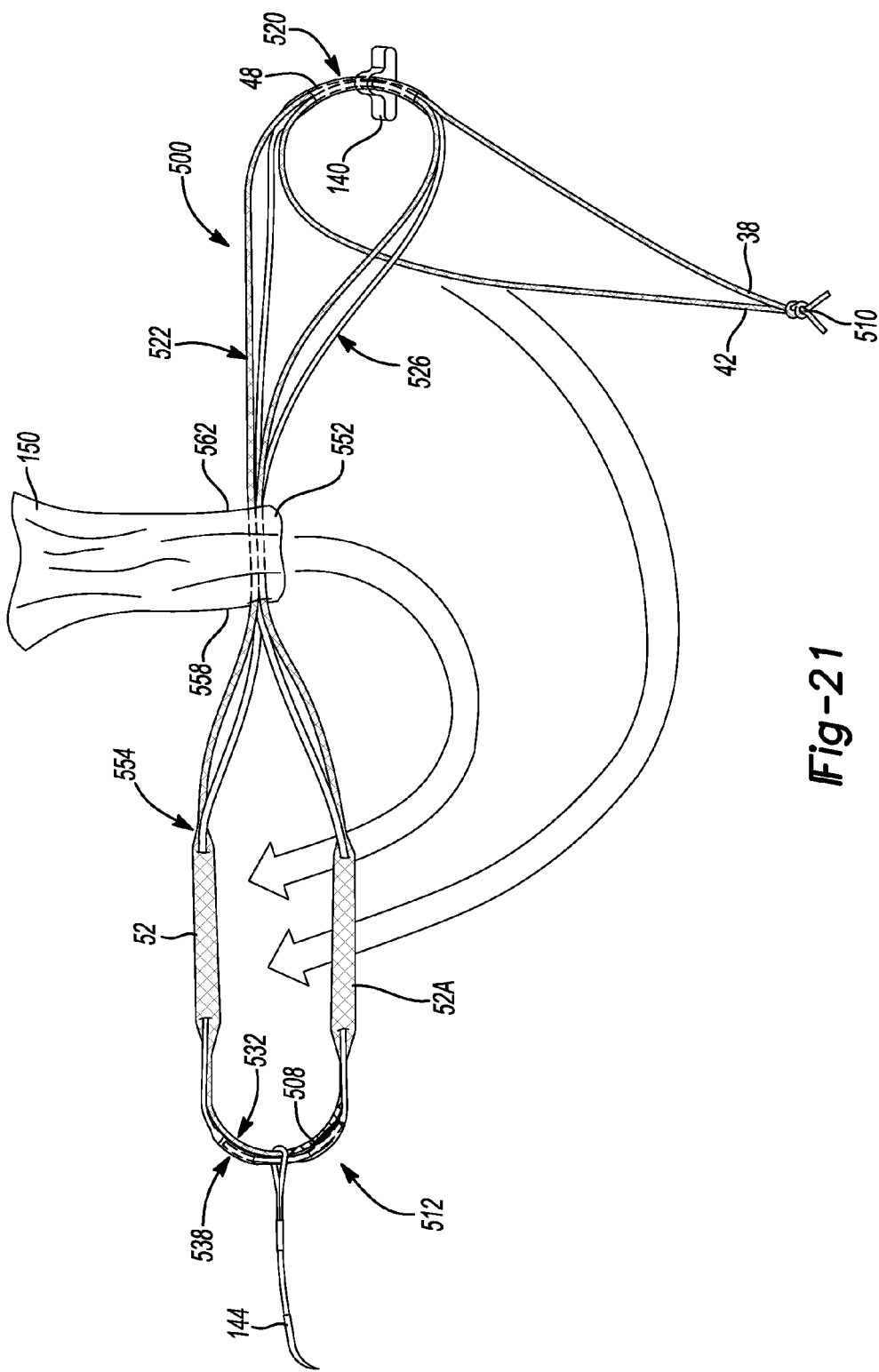
FIGS. 21-24 depict an exemplary technique for coupling the adjustable flexible member construct of FIG. 15 to soft tissue according to the present teachings.
Figure 22:
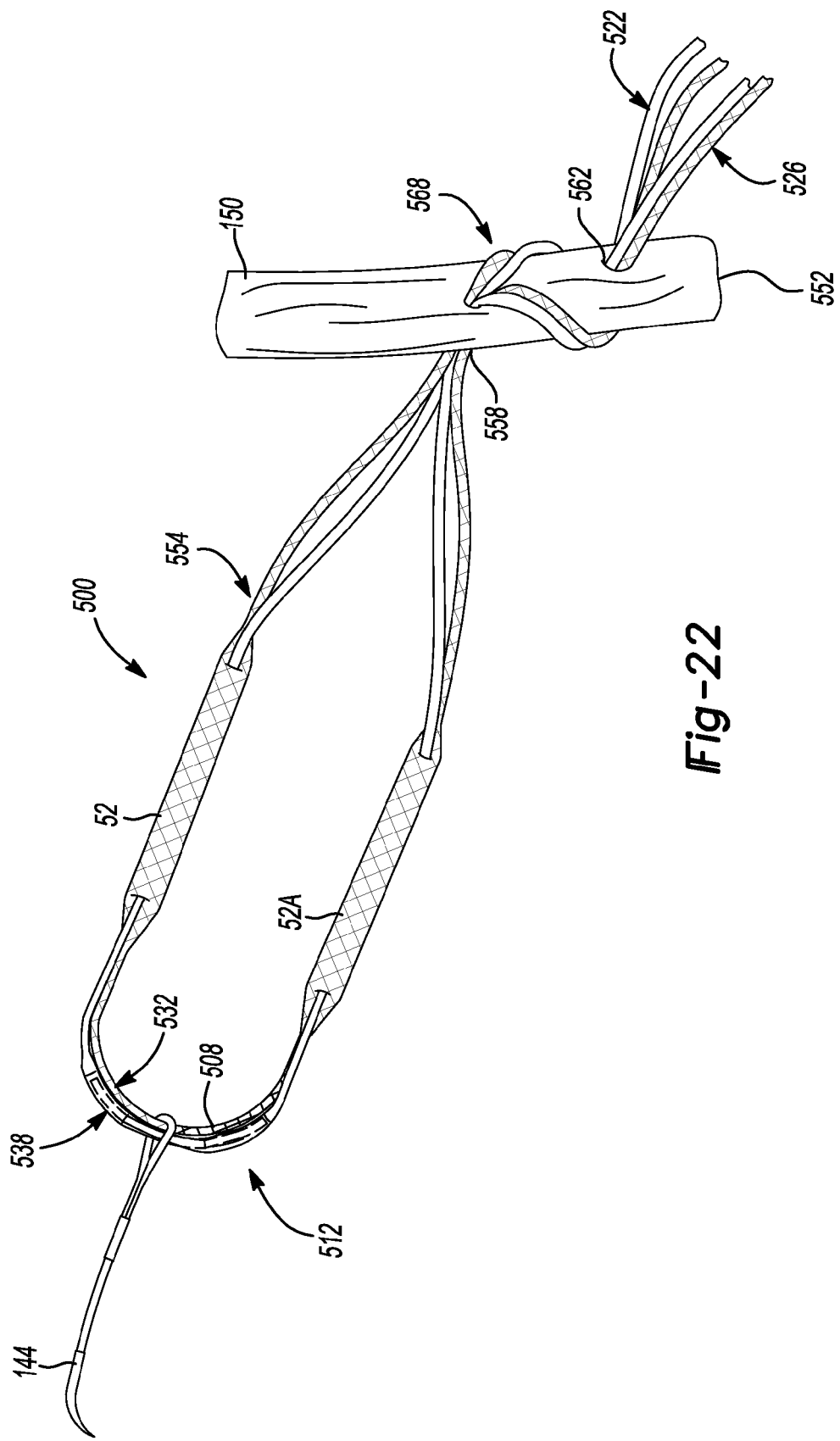
Figure 23:
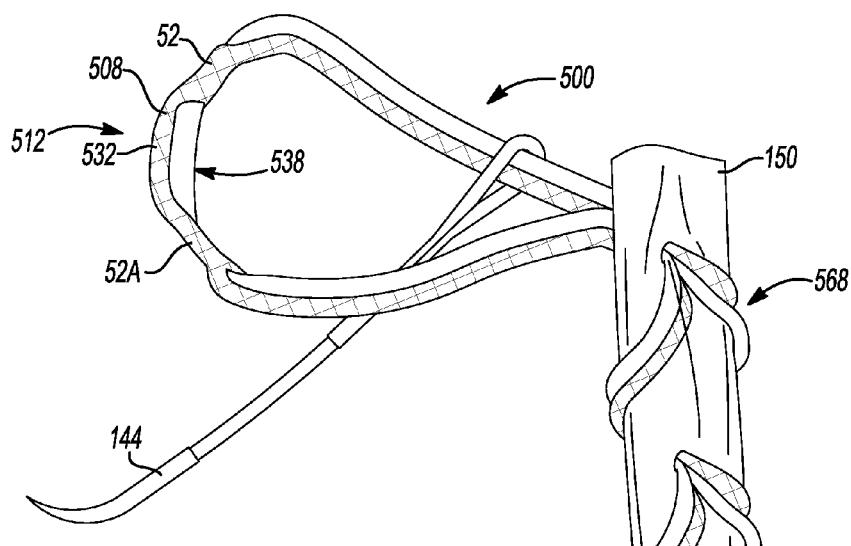
Figure 24:
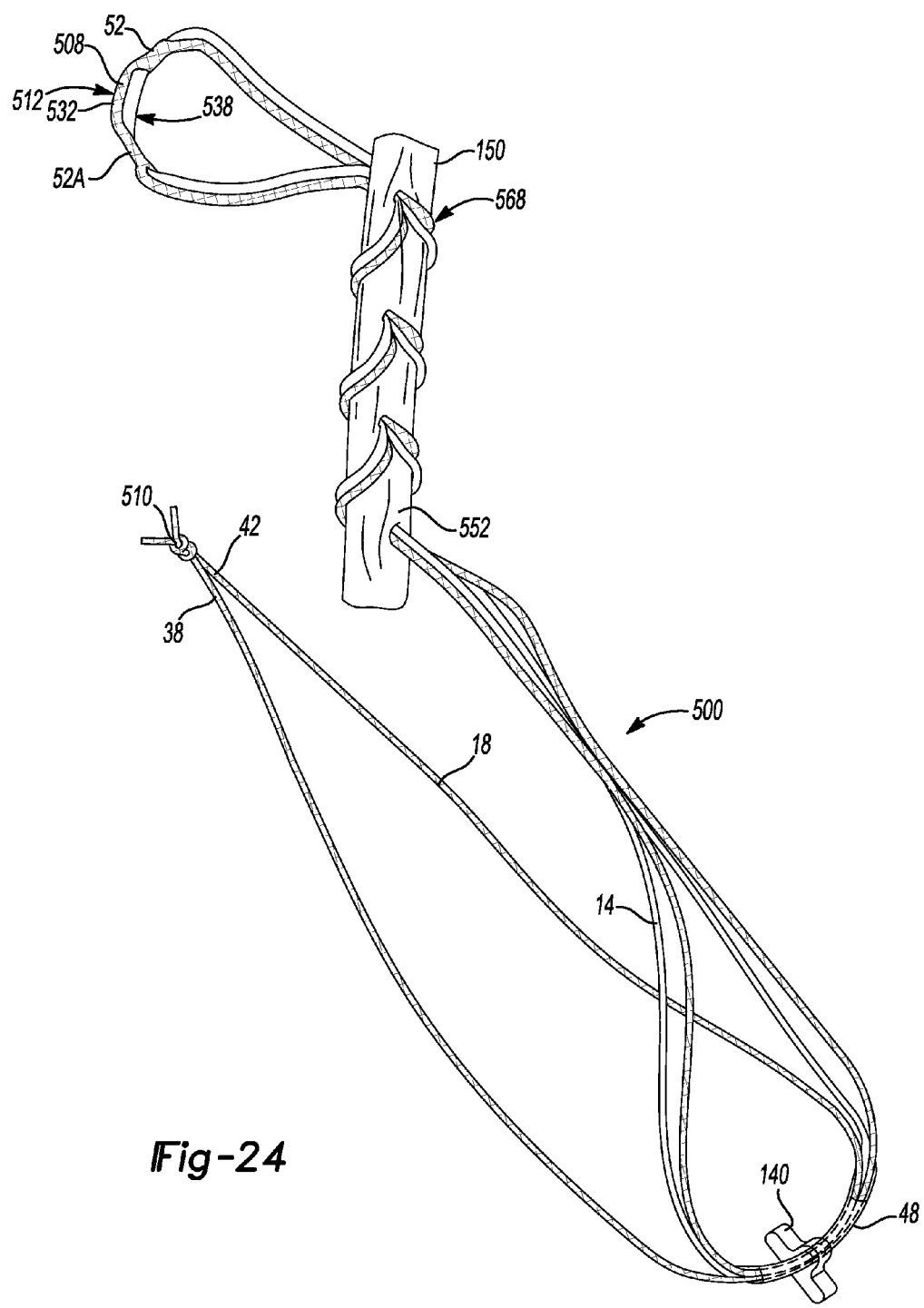

With particular reference to FIGS. 21-24, coupling adjustable flexible member construct 500 to soft tissue will now be discussed in greater detail. In the exemplary configuration illustrated, construct 500 is shown being coupled to distal bicep tendon 150. It should be appreciated, however, that construct 500 can be used in various techniques for coupling soft tissue to bone, such as in an ACL construction procedure, for example. Needle 144 can be used to pass first end 512 of construct 500 through distal bicep tendon 150 a first time, as shown in FIG. 21. The second end 520 of construct 500 along with an end 552 of distal bicep tendon 150 can be passed through a portion 554 of construct 500 extending between the first end 512 and an exit side 558 of distal bicep tendon 150 opposite an entrance side 562. Needle 144 along with first end 512 can then be passed through the entrance side 562 again and the process repeated to form a weave-like pattern 568 shown in FIG. 23. The needle 144 can then be removed from first end 512, as shown in FIG. 24. The pattern 568 can form a non-tortuous path for the suture so as to facilitate initial sliding of the distal bicep tendon 150 relative to flexible member 14, as will be discussed below.

Figure 25:
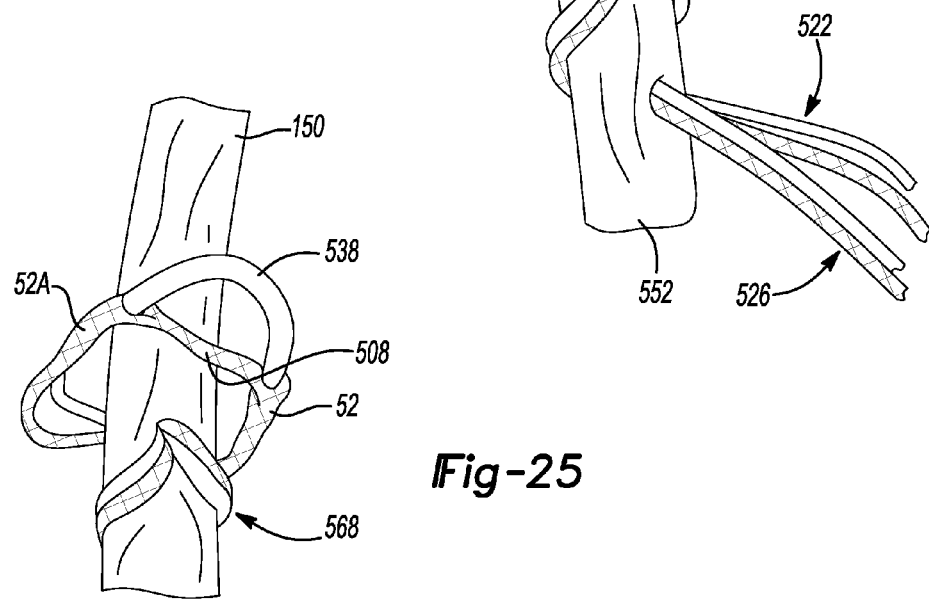
FIGS. 25-29 depict an exemplary technique for securing the soft tissue to bone using the adjustable flexible member construct of FIG. 15 according to the present teachings.
Figure 26:
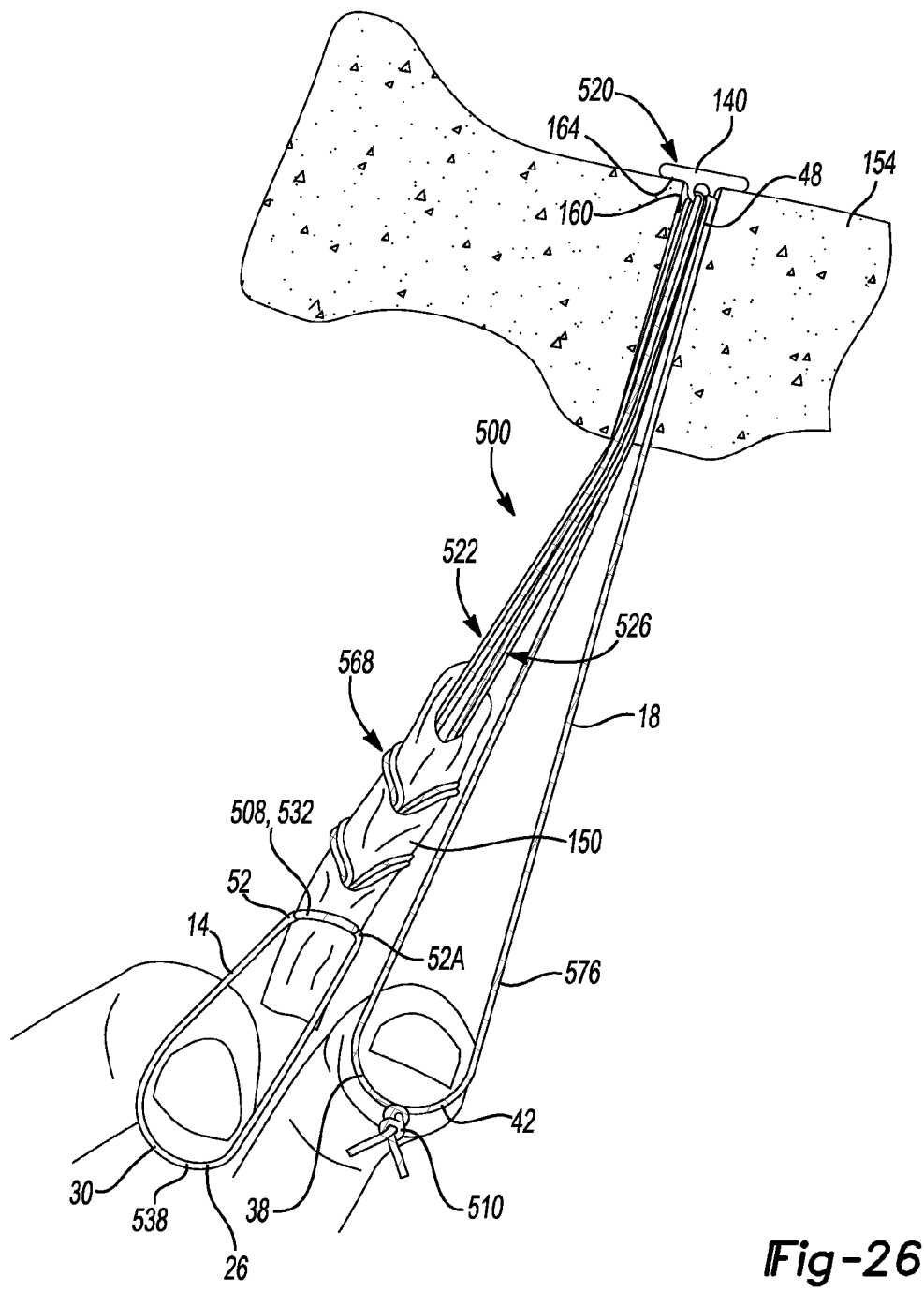

With additional reference to FIGS. 25-29, attaching the distal bicep tendon 150 to the radius bone 154 will now be discussed in greater detail. With particular reference to FIGS. 25 and 26, the second end 520 of construct 500 can be passed through bore 160 in radius bone 154. The formed loop portion 538 can be separated from alignment with the fixed portion 508, as shown in FIG. 25, and tension can be applied to the construct 500 via ends 26, 30 and ends 38, 42. In the exemplary configuration illustrated in FIG. 26, ends 26, 30 (FIG. 20) are in the form of optional loop 538 and ends 38, 42 are in the form of an optional loop 576 via knot 510. In this configuration, the loops 538 and 576 can be tensioned either by hand or with any appropriate instrument. Applying tension to construct 500 in this manner can seat anchor member 140 against outer surface 164 of radius bone 154 and facilitate drawing distal bicep tendon 150 toward and into secure engagement with radius bone 154, as will be discussed below.

Figure 27:
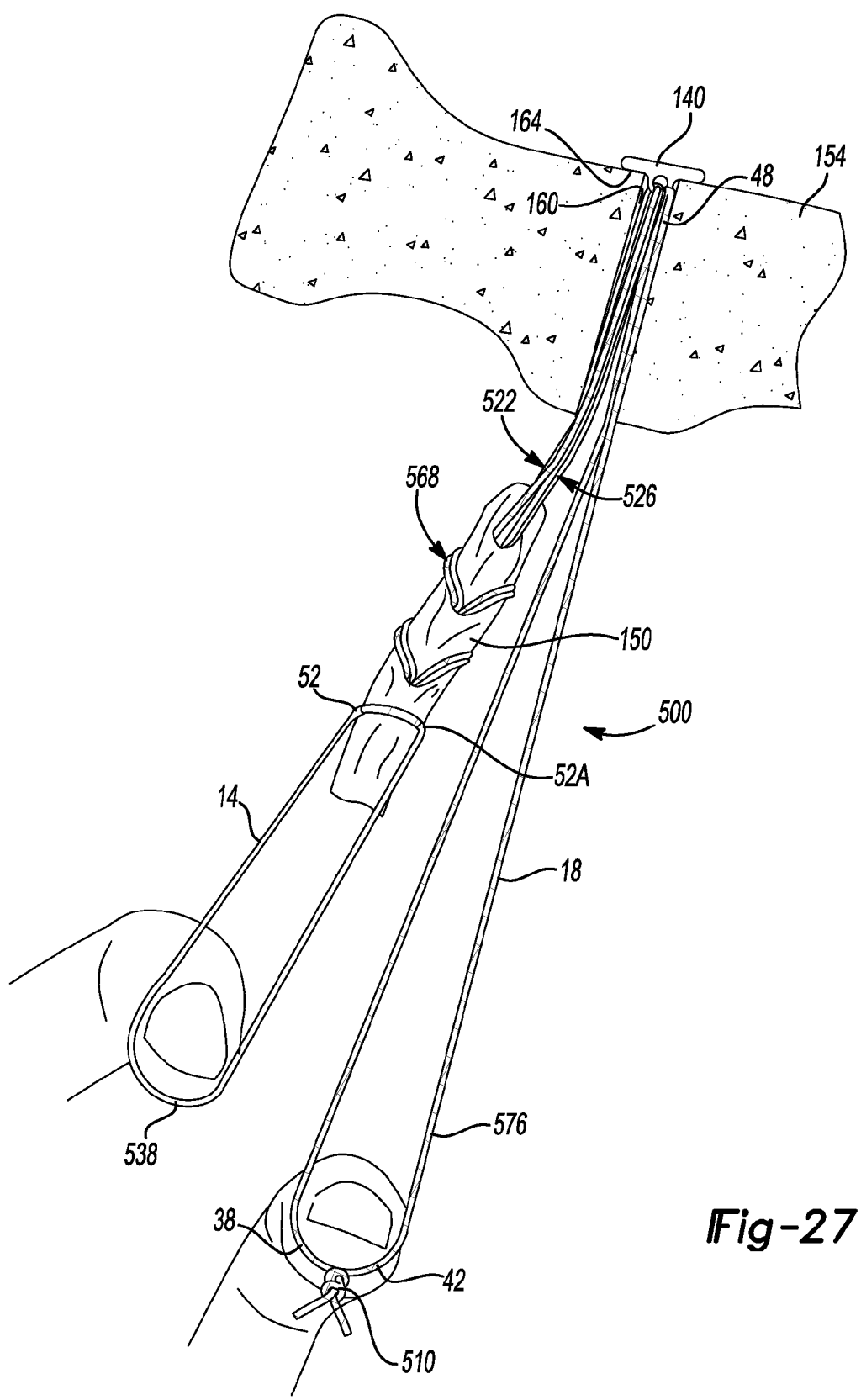
Figure 28:
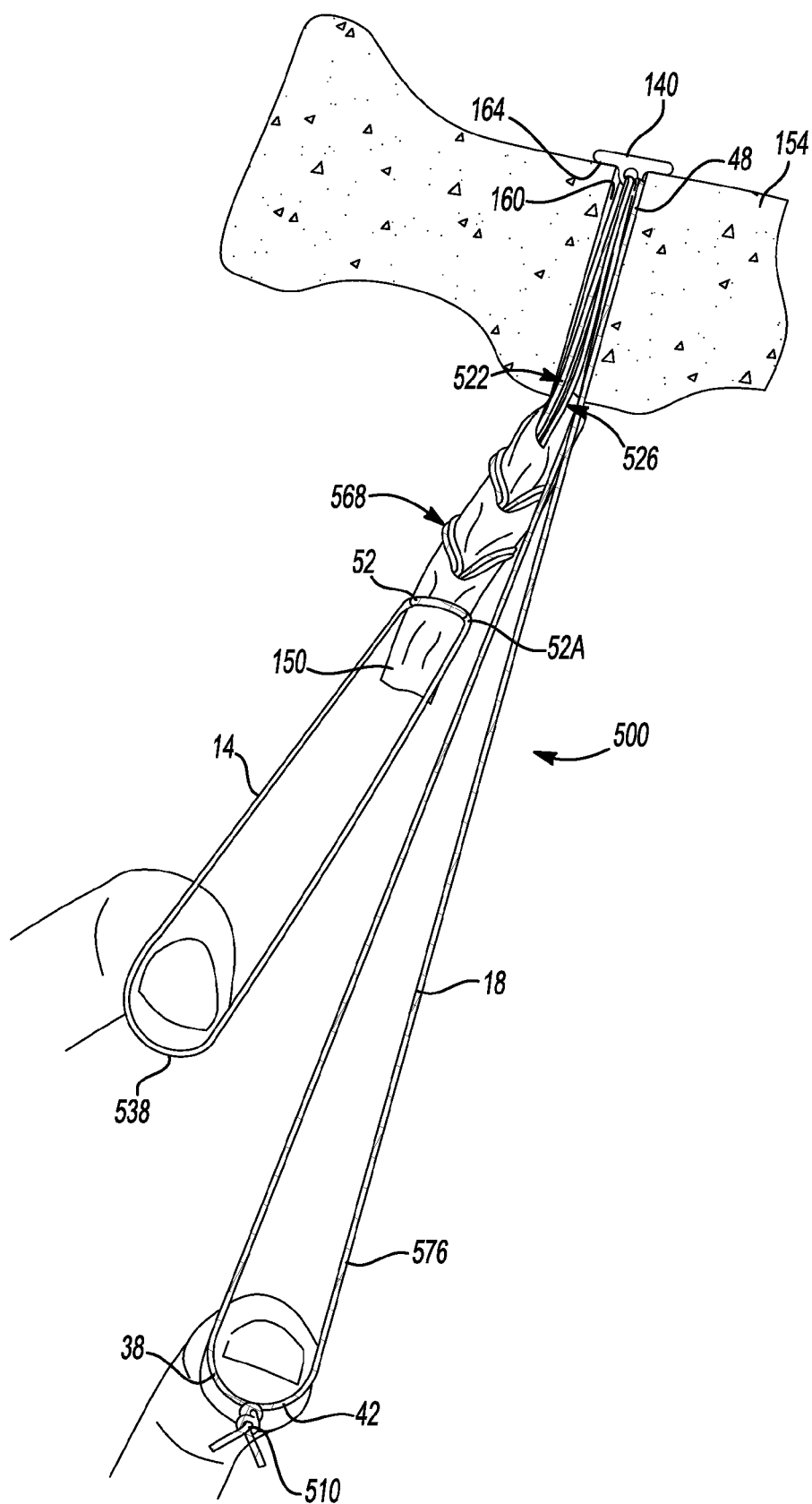

In particular, once anchor member 140 is seated against radius bone 154 with an initial amount of tension being applied to construct 500 to remove any slack from the construct, further tensioning of the flexible member 18 via loop 576 can draw fixed portion 508 against the distal bicep tendon 150 by moving the flexible member 18 relative to the flexible member 14 and the distal bicep tendon 150. In other words, flexible member 14, under tension, remains taut relative to anchor member 140 such that flexible member 14 can initially serve a function of a guidewire or guiding path for moving distal bicep tendon 150 toward radius bone 154. Further tension applied to loop 576 of flexible member 18 can shorten a length of loop 532 relative to passage portion 48 and thus draw distal bicep tendon 150 along flexible member 14 toward radius bone 154, as shown in FIGS. 27 and 28.

The adjustable flexible member construct 500 can provide support for holding the distal bicep tendon 150 and associated muscle to the radius bone 154 via the four flexible member strands extending between the passage portion 48 and the passage portions 52, 52A. In particular, although the flexible member 14 serves the initial function of a guidewire while drawing the distal bicep tendon 150 toward the radius bone 154, it also serves to hold the distal bicep tendon 150 at the desire tension/load via the portions of flexible member 18 that form the adjustment portions that extend between passage portion 48 at the anchor member 140 and passage portions 52, 52A at the distal bicep tendon 150. Similarly, the portions of flexible member 18 that form part of adjustment portions 522, 526 extending between the passage portions 52, 52A and passage portion 48 can also hold the bicep tendon 150 at the desired tension. In a similar manner to the constructs discussed above, the passage portions 48, 52, 52A can automatically lock the respective flexible members 18, 14 under the desired tension/load without the use of a knot.

Figure 29:
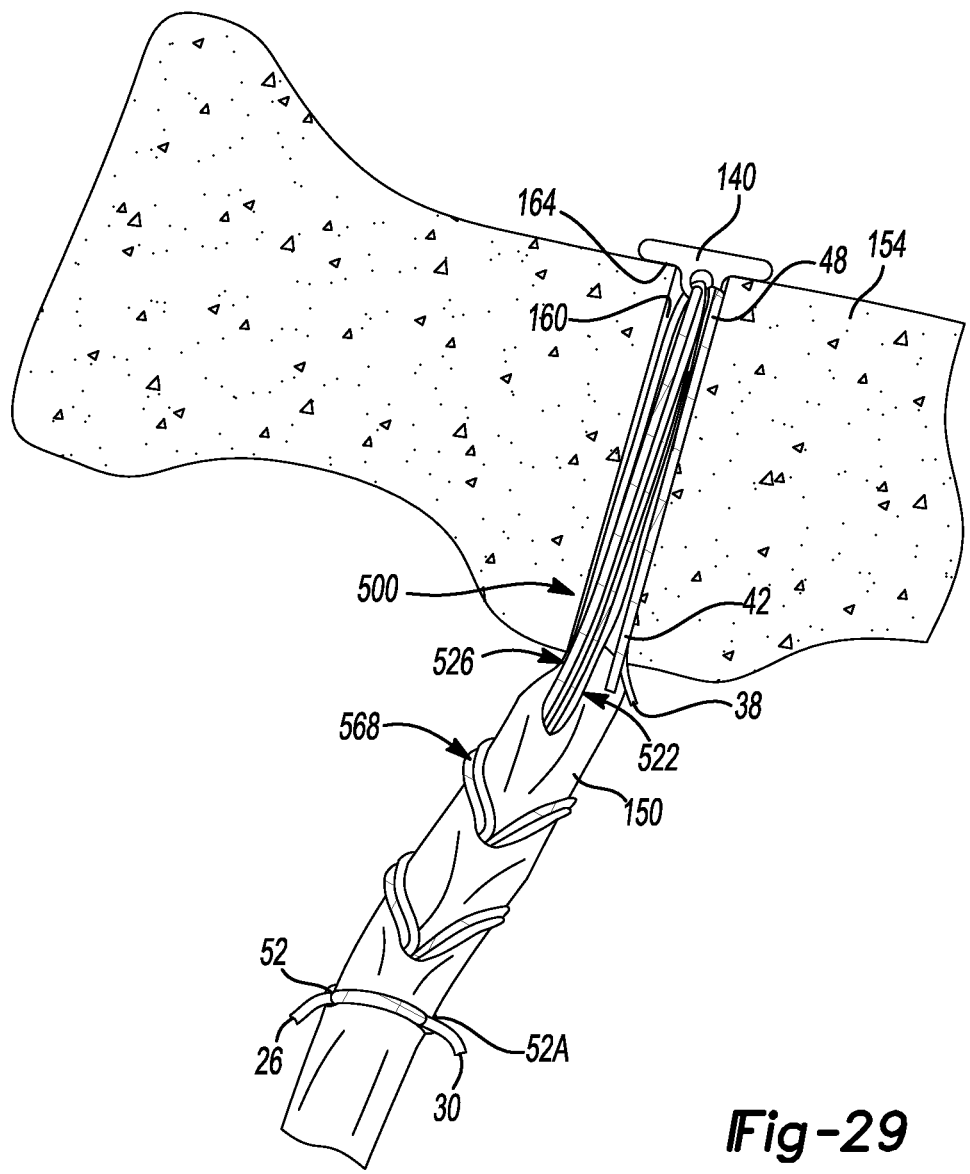

Upon tensioning flexible member 18 via loop 576 a sufficient amount to draw distal bicep tendon 150 into secure engagement with radius bone 154 under a desired tensile load, such as shown in FIG. 29, the ends 26, 30 of flexible member 14 extending from passage portions 52, 52A can be trimmed. The ends 38, 42 extending from passage portion 48 and bore 160 in radius bone 154 can also be trimmed.

While one or more specific examples have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

What is claimed is:

1. An apparatus for use in surgical implantation, comprising:
   a first flexible member having a first end, a second end and a first body extending therebetween, the first body having a first body longitudinal axis, a first body interior and a first body exterior, the first body interior defining a first passage portion along the first body longitudinal axis and spaced apart from the second end, the first body longitudinally extending from the first end to the second end along the first body longitudinal axis;
   a second flexible member having a first end, a second end and a second body extending therebetween, the second body having a second body longitudinal axis, a second body interior and a second body exterior, the second body interior defining a second passage portion along the second body longitudinal axis and spaced apart from the second end, the second body longitudinally extending from the first end to the second end along the second body longitudinal axis;
   the first end of the first flexible member passing into and through the second passage portion in a first direction such that the first end of the first flexible member extends outside of the second passage portion; and
   the first end of the second flexible member passing into and through the first passage portion in a second direction such that the first end of the second flexible member extends outside of the first passage portion to form a self-locking adjustable flexible member construct;
   wherein applying tension to the first ends of the first and second flexible members draws the first and second passage portions and corresponding second ends toward each other.

2. The apparatus of claim 1, wherein the second ends of the first and second flexible members are adapted to be coupled directly to soft tissue.

3. The apparatus of claim 2, further comprising needle members attached directly to the second ends of the first and second flexible members.

4. The apparatus of claim 1, wherein the adjustable flexible member construct comprises an adjustable length portion between the first and second passage portions, including:
   a first portion of the first flexible member extending between the first and second passage portions, and a second portion of the second flexible member extending between the first and second passage portions.

5. The apparatus of claim 4, wherein tensioning the first ends of the first and second flexible members reduces a length of the adjustable length portion, the adjustable flexible member construct configured to automatically maintain the reduced length of the adjustable length portion under tension in an absence of a knot.

6. The apparatus of claim 4, further comprising a flexible fixation member slidably coupled to the adjustable length portion.

7. The apparatus of claim 4, further comprising an anchor member coupled to the adjustable length portion.

8. The apparatus of claim 1, further comprising:
   the second end of the first flexible member passing into and through the second passage portion in a direction opposite the first direction of the first end of the first flexible member to form a first adjustable loop; and
   the second end of the second flexible member passing into and through the first passage portion in a direction opposite the second direction of the first end of the second flexible member to form a second adjustable loop;
   wherein applying tension to the first and second ends of the first and second flexible members reduces a size of the first and second adjustable loops.

9. The apparatus of claim 8, wherein the first and second passage portions are spaced apart from each other.

10. The apparatus of claim 8, wherein the first end of the second flexible member passes into the first passage portion at a first end thereof and out of the first passage portion at a second end thereof spaced apart from the first end, the second end of the second flexible member passes into the first passage portion at the second end thereof and out of the first passage portion at the first end thereof; and
    wherein the first end of the first flexible member passes into the second passage portion at a third end thereof and out of the second passage portion at a fourth end thereof spaced apart from the third end, the second end of the first flexible member passes into the second passage portion at the fourth end thereof and out of the second passage portion at the third end thereof.

11. The apparatus of claim 8, wherein the first and second passage portions have a larger width than remaining portions of the respective bodies of the first and second flexible members.

12. The apparatus of claim 8, wherein the first and second adjustable loops include first and second self-locking adjustable loops configured to self-lock under tension to maintain a reduced size of the first and second adjustable loops under tension in an absence of a knot.

13. The apparatus of claim 8, further comprising first and second flexible anchors coupled to the first and second adjustable loops of the adjustable flexible member construct.

14. The apparatus of claim 13, wherein the first flexible anchor is slidably coupled to the first passage portion and the second flexible anchor is slidably coupled to the second passage portion.

15. The apparatus of claim 13, wherein the adjustable flexible member construct passes though a portion of a passage defined by each flexible anchor spaced apart from respective ends of each of the first and second flexible anchors; and
    wherein the first and second flexible anchors are configured to be collapsible upon engagement with bone to form an anchoring mass having a locking profile.

16. The apparatus of claim 1, wherein the first and second flexible members each comprise a suture formed of a hollow braided or woven structure.

17. The apparatus of claim 1, wherein the first and second directions are opposite each other.

18. An apparatus for use in surgical implantation, comprising:
   a first suture having a first end, a second end and a first body extending therebetween, the first body defining a first passage portion;
   a second suture having a first end, a second end and a second body extending therebetween, the second body defining a second passage portion;
   the first end of the first suture passing into and through the second passage portion such that the first end of the first suture extends outside of the second passage portion, the second end of the first suture passing into and through the second passage portion in a direction opposite the first end of the first suture so as to form a first self-locking adjustable loop; and
   the first end of the second suture passing into and through the first passage portion such that the first end of the second suture extends outside of the first passage portion;
   wherein applying tension to the first and second ends of the first suture reduces a size of the first adjustable loop.

19. The apparatus of claim 18, wherein the second end of the second suture passes into and through the first passage portion in a direction opposite the first end of the second suture to form a second self-locking adjustable loop, and wherein applying tension to the first and second ends of the second suture reduces a size of the second adjustable loop.

20. The apparatus of claim 19, further comprising first and second flexible tubular anchors slidably coupled to the first and second adjustable loops;
   wherein each flexible tubular anchor is formed from woven or braided suture and includes first and second openings intermediate respective first and second ends thereof, the first and second adjustable loops being passed through the passage of the respective first and second flexible anchors via the respective first and second openings such that at least a portion of the first and second passage portions are positioned within the passage of the respective first and second flexible anchors; and
   wherein portions of the first and second flexible anchors between the first and second ends and the respective first and second openings define anchoring leg portions.

21. The apparatus of claim 19, wherein the first and second self-locking adjustable loops are configured to self-lock under tension via the first and second passage portions to maintain a reduced size of the first and second adjustable loops under tension in an absence of a knot.

* * * * *